United States Patent
Zhang et al.

(10) Patent No.: US 9,738,629 B2
(45) Date of Patent: *Aug. 22, 2017

(54) BRIDGED RING COMPOUNDS AS HEPATITIS C VIRUS INHIBITORS, PHARMACEUTICAL COMPOSITIONS AND USES THEREOF

(71) Applicant: SUNSHINE LAKE PHARMA CO., LTD., Dongguan, Guangdong (CN)

(72) Inventors: Yingjun Zhang, Dongguan (CN); Hongming Xie, Dongguan (CN); Jiancun Zhang, Dongguan (CN); Bailin Hu, Dongguan (CN); Qinghong Fang, Dongguan (CN); Qingyun Ren, Dongguan (CN)

(73) Assignee: SUNSHINE LAKE PHARMA CO., LTD., Dongguan, Guangdong (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/107,105

(22) PCT Filed: Jan. 22, 2015

(86) PCT No.: PCT/CN2015/071352
§ 371 (c)(1),
(2) Date: Jun. 22, 2016

(87) PCT Pub. No.: WO2015/110048
PCT Pub. Date: Jul. 30, 2015

(65) Prior Publication Data
US 2017/0044140 A1   Feb. 16, 2017

(30) Foreign Application Priority Data
Jan. 23, 2014 (CN) .......................... 2014 1 0032395

(51) Int. Cl.
| | | |
|---|---|---|
| A01N 47/28 | (2006.01) | |
| C07D 403/14 | (2006.01) | |
| C07D 405/14 | (2006.01) | |
| A61K 31/4178 | (2006.01) | |
| A61K 31/4184 | (2006.01) | |
| A61K 45/06 | (2006.01) | |

(52) U.S. Cl.
CPC ........ *C07D 403/14* (2013.01); *A61K 31/4178* (2013.01); *A61K 31/4184* (2013.01); *A61K 45/06* (2013.01); *C07D 405/14* (2013.01)

(58) Field of Classification Search
CPC C07D 403/14; C07D 405/14; A61K 31/4178; A61K 31/4184; A61K 45/06
See application file for complete search history.

(56) References Cited

U.S. PATENT DOCUMENTS

| | | |
|---|---|---|
| 7,659,270 B2 | 2/2010 | Bachand et al. |
| 7,704,992 B2 | 4/2010 | Bachand et al. |
| 8,008,263 B2 | 8/2011 | Britt et al. |
| 8,143,414 B2 | 3/2012 | Lavoie et al. |
| 8,221,737 B2 | 7/2012 | Or et al. |
| 8,273,341 B2 | 9/2012 | Guo et al. |
| 8,303,944 B2 | 11/2012 | Bachand et al. |
| 8,314,135 B2 | 11/2012 | Qiu et al. |
| 8,354,419 B2 | 1/2013 | Henderson et al. |

(Continued)

FOREIGN PATENT DOCUMENTS

| | | | |
|---|---|---|---|
| WO | WO2004002977 A1 | 1/2004 | |
| WO | WO2010138790 A1 | 12/2010 | |
| WO | WO2011079327 A1 | 6/2011 | |
| WO | WO2011087740 A1 | 7/2011 | |
| WO | WO2011119853 A1 | 9/2011 | |
| WO | WO2011119870 A1 | 9/2011 | |
| WO | WO 2011146401 A1 * | 11/2011 | ......... A61K 31/4025 |
| WO | WO2011149856 A1 | 12/2011 | |
| WO | WO2011156543 A2 | 12/2011 | |
| WO | WO2012003642 A1 | 1/2012 | |
| WO | WO2012013643 A1 | 2/2012 | |
| WO | WO2012018534 A2 | 2/2012 | |
| WO | WO2012040923 A1 | 4/2012 | |
| WO | WO2012040924 A1 | 4/2012 | |
| WO | WO2012041014 A1 | 4/2012 | |
| WO | WO2012041227 A1 | 4/2012 | |

(Continued)

OTHER PUBLICATIONS

International Search Report of PCT/CN2015/071352.
Written Opinion of PCT/CN2015/071352.

*Primary Examiner* — Jason Sims
*Assistant Examiner* — Ibrahim D Bori
(74) *Attorney, Agent, or Firm* — Kam W. Law; Squire Patton Boggs (US) LLP

(57) ABSTRACT

Provided herein is a bridged bring compound of formula (I) or a stereoisomer, a tautomer, an N-oxide, a hydrate, a solvate, a metabolite, a pharmaceutically acceptable salt or a prodrug thereof, which can be used for treating treat hepatitis C virus C(HCV) infection or hepatitis C disease. Furthermore provided herein are pharmaceutical compositions containing the compounds and the method of using the compounds or pharmaceutical compositions thereof in the treatment of HCV infection or hepatitis C.

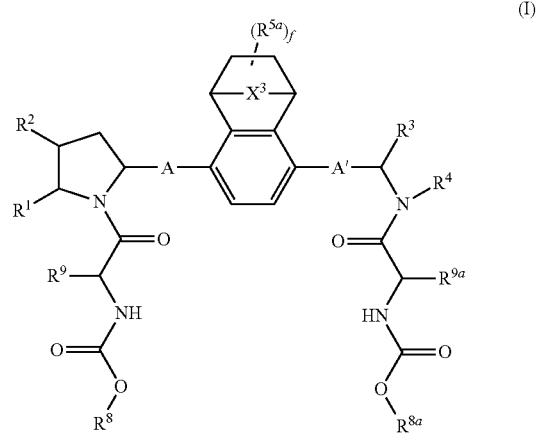

(I)

11 Claims, No Drawings

(56) References Cited

U.S. PATENT DOCUMENTS

| | | |
|---|---|---|
| 8,362,068 B2 | 1/2013 | Dousson et al. |
| 8,563,714 B2 | 10/2013 | Bur et al. |
| 8,637,561 B2 | 1/2014 | Qiu |
| 8,686,026 B2 | 4/2014 | Liepold et al. |
| 8,709,999 B2 | 4/2014 | Zhong et al. |
| 8,716,454 B2 | 5/2014 | Kullmann et al. |
| 8,865,756 B2 | 10/2014 | Li et al. |
| 8,871,759 B2 | 10/2014 | Coburn et al. |
| 8,921,369 B2 | 12/2014 | Zhong et al. |
| 9,079,887 B2 | 7/2015 | Bacon et al. |
| 9,139,569 B2 | 9/2015 | Rosenblum et al. |
| 9,150,554 B2 | 10/2015 | Li et al. |
| 9,303,061 B2 | 4/2016 | Zhang et al. |
| 9,309,231 B2 | 4/2016 | Zhang et al. |
| 9,334,291 B2 | 5/2016 | Zhan |
| 2011/0112100 A1 | 5/2011 | Milbank et al. |
| 2011/0274648 A1 | 11/2011 | Lavoie et al. |
| 2011/0312996 A1 | 12/2011 | Buckman et al. |
| 2012/0039847 A1 | 2/2012 | Zhao |
| 2012/0115918 A1 | 5/2012 | DeGoey et al. |
| 2012/0195857 A1 | 8/2012 | Belema et al. |
| 2012/0276047 A1 | 11/2012 | Rosenblum et al. |
| 2013/0072523 A1 | 3/2013 | Liu et al. |
| 2015/0232509 A1 | 8/2015 | Zhang et al. |
| 2015/0299215 A1 | 10/2015 | Zhang et al. |
| 2015/0307509 A1 | 10/2015 | Zhang et al. |

FOREIGN PATENT DOCUMENTS

| | | |
|---|---|---|
| WO | WO2012050848 A1 | 4/2012 |
| WO | WO2012050918 A2 | 4/2012 |
| WO | WO2012083048 A2 | 6/2012 |
| WO | WO2012083053 A2 | 6/2012 |
| WO | WO2012122716 A1 | 9/2012 |
| WO | WO2012125926 A2 | 9/2012 |
| WO | WO2013021337 A1 | 2/2013 |
| WO | WO2013022810 A1 | 2/2013 |
| WO | WO2014082381 A1 | 6/2014 |
| WO | WO2014131315 A1 | 9/2014 |
| WO | WO2015042375 A1 | 3/2015 |

* cited by examiner

BRIDGED RING COMPOUNDS AS HEPATITIS C VIRUS INHIBITORS, PHARMACEUTICAL COMPOSITIONS AND USES THEREOF

CROSS-REFERENCE TO RELATED APPLICATIONS

This is a U.S. national stage application of the International Patent Application No. PCT/CN2015/071352, filed Jan. 22, 2015, which claims priority to Chinese Patent Application No. 201410032395.3, filed Jan. 23, 2014, both of which are incorporated herein by reference in their entirety.

FIELD

The present disclosure relates to a field of medicine, and more particularly to compounds for treating Hepatitis C virus (HCV) infection, compositions comprising such compounds, uses of the compounds and the compositions thereof, and methods thereof. In particular, the invention relates to use of bridged compounds as NS5A protein inhibitors. More specifically, the invention relates to compounds which can inhibit the function of the NS5A protein encoded by Hepatitis C virus (HCV), pharmaceutical compositions comprising such compounds, and methods for inhibiting the function of the NS5A protein by the compounds and pharmaceutical compositions disclosed herein.

BACKGROUND

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. Chronic HCV infection is thus a major worldwide cause of liver-related premature mortality.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. The treatment has side effects in many patients, so they do not durably respond to treatment. Thus, new and effective methods of treating HCV infection are urgently needed.

HCV is a positive-stranded RNA virus. Based on a comparison of the deduced amino acid sequence and the extensive similarity in the 5'untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame (ORF).

Considerable heterogeneity is found within nucleotide and encoded amino acid sequence throughout the HCV genome. At least seven major genotypes have been characterized, and more than 50 subtypes have been described. In HCV infected cells, viral RNA is translated into a polyprotein that is cleaved into ten individual proteins. At the amino terminus are structural proteins, follows E1 and E2. Additionally, there are six non-structural proteins, NS2, NS3, NS4A, NS4B, NS5A and NS5B, which play a function role in the HCV lifecycle (see, for example, Lindenbach et al., *Nature*, 2005, 436, 933-938).

The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A and NS5B) is effected by two viral proteases. The first one is believed to be a metalloprotease and cleaves at the NS2-NS3 junction; the second one is a serine protease within the N-terminal region of NS3 (also referred herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, actin g as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to herein as HCV polymerase) is a RNA-dependent RNA polymerase that is involved in the replication of HCV.

Compounds which are use for treating HCV-infected patients are desired which selectively inhibit HCV viral replication. In particular, compounds which are effective to inhibit the function of the NS5A protein are desired. The HCV NS5A protein is described, for example, in Tan et al., *Virology*, 2001, 284, 1-12; and in Park et al., *J. Biol. Chem.*, 2003, 278, 30711-30718.

SUMMARY

Provided herein are novel bridged ring compounds and methods of their uses to treat HCV infection. Specifically, it has been found that the bridged ring compounds disclosed herein, and compositions thereof, are effective as inhibitors of HCV infection, especially the HCV NS5A protein.

In one aspect, provided herein are compounds having Formula (I), or a stereoisomer, a geometric isomer, a tautomer, an N-oxide, a hydrate, a solvate, a metabolite, a pharmaceutically acceptable salt or a prodrug thereof,

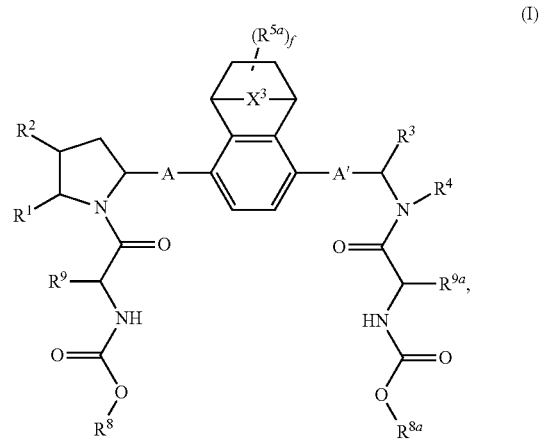

(I)

wherein $X^3$ is O, S, $NR^6$ or $(CR^7R^{7a})_e$;

e is 1, 2, 3 or 4;

each of A and A' is independently a bond, $C_{1-3}$ alkylene, $C_{2-4}$ alkenylene, $C_{3-8}$ cycloalkylene, $C_{2-10}$ heterocycloalkylene, or each of A and A' is independently

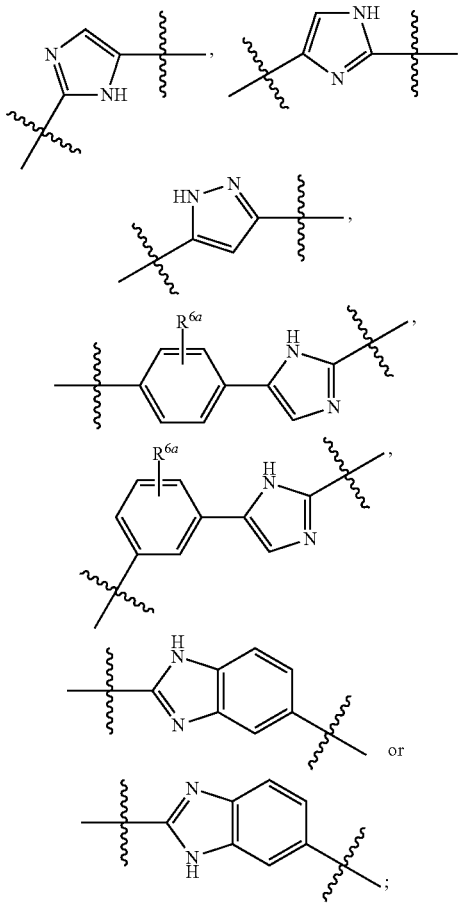

$R^1$ is $C_{1-4}$ alkyl, $C_{1-4}$ heteroalkyl or $C_{6-10}$ aryl;

$R^2$ is H, deuterium, $C_{1-4}$ alkyl, $C_{1-4}$ heteroalkyl or $C_{6-10}$ aryl;

each of $R^3$ and $R^4$ is independently H, deuterium, $C_{1-4}$ alkyl, $C_{1-4}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-4}$-alkyl, $C_{1-4}$ alkoxy, or $R^3$ and $R^4$, together with the N—CH to which they are attached, form a 3-8 membered heterocycle, a 3-8 membered carbocycle, a $C_{5-12}$ fused bicycle or a $C_{5-12}$ spiro bicycle; wherein each of the $C_{1-4}$ alkyl, $C_{1-4}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-4}$-alkyl, $C_{1-4}$ alkoxy, 3-8 membered heterocycle, 3-8 membered carbocycle, $C_{5-12}$ fused bicycle and $C_{5-12}$ spiro bicycle is optionally and independently substituted with one or more substituents independently selected from deuterium, hydroxy, amino, oxo (=O), F, Cl, Br, I, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{1-6}$ alkoxy, $C_{1-6}$ alkylamino, $C_{6-10}$ aryl, $C_{6-10}$ aryloxy, $C_{6-10}$ arylamino, $C_{1-9}$ heteroaryl, $C_{1-9}$ heteroaryloxy, $C_{2-6}$ alkenyl, $C_{3-10}$ cycloalkyl or $C_{2-10}$ heterocyclyl;

each $R^{5a}$ and $R^{6a}$ is independently H, deuterium, oxo (=O), hydroxy, amino, cyano, mercapto, nitro, F, Cl, Br, I, $C_{1-6}$ alkoxy, $C_{1-6}$ alkyl, $C_{6-10}$ aryl, —$CF_3$, —$OCF_3$, $C_{1-6}$ alkylamino, $C_{3-10}$ cycloalkyl or $C_{6-10}$ aryloxy;

$R^6$ is H, deuterium, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-8}$ carbocyclyl;

each $R^7$, $R^{7a}$, $R^9$ and $R^{9a}$ is independently H, deuterium, $C_{1-6}$ alkyl, $C_{1-6}$ alkoxy-$C_{1-6}$-alkyl, $C_{1-6}$ haloalkyl, $C_{1-6}$ hydroxyalkyl, $C_{1-6}$ heteroalkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-8}$ cycloalkyl-$C_{1-6}$-alkyl, $C_{6-10}$ aryl, $C_{1-9}$ heteroaryl, $C_{2-10}$ heterocyclyl or $C_{3-8}$ carbocyclyl;

each of $R^8$ and $R^{8a}$ is independently H, deuterium, $C_{1-6}$ alkyl, $C_{1-6}$ haloalkyl, $C_{1-6}$ hydroxyalkyl, $C_{1-6}$ heteroalkyl, $C_{6-10}$ aryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and f is 0, 1, 2, 3 or 4.

In some embodiments, wherein $X^3$ is $(CR^7R^{7a})_e$; and each $R^7$ and $R^{7a}$ is independently H, deuterium, $C_{1-3}$ alkyl, $C_{1-3}$ heteroalkyl, $C_{1-3}$ alkoxy-$C_{1-3}$-alkyl, $C_{1-3}$ alkylamino-$C_{1-3}$-alkyl, $C_{6-10}$ aryl-$C_{1-3}$-alkyl, $C_{2-10}$ heterocyclyl-$C_{1-3}$-alkyl, $C_{3-8}$ cycloalkyl or $C_{6-10}$ aryl.

In some embodiments, wherein $R^3$ and $R^4$, together with N—CH to which they are attached, form one of the following groups:

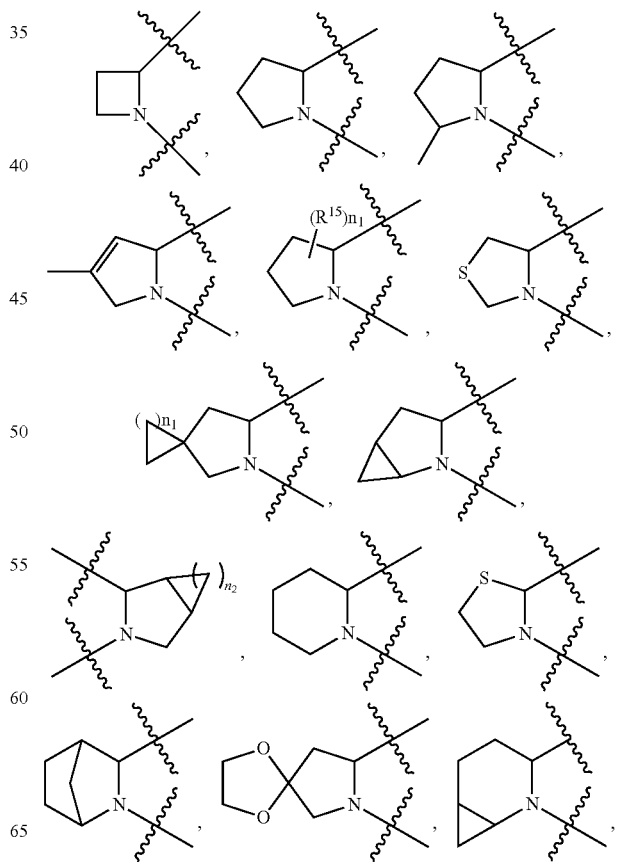

-continued

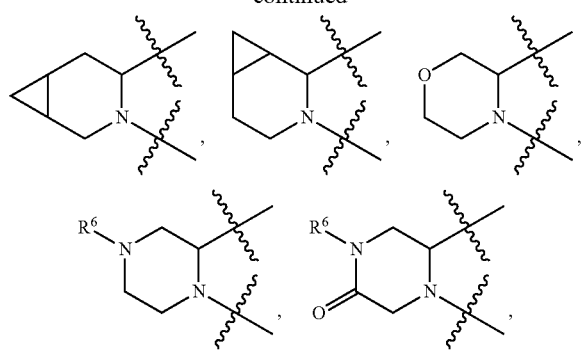

wherein each $R^{15}$ is independently H, deuterium, F, Cl, Br, I, cyano, hydroxy, oxo(=O), phenyl, $C_{1-4}$ alkyl, $C_{1-4}$ hydroxyalkyl, $C_{1-4}$ haloalkyl, $C_{1-4}$ alkoxy, $C_{1-4}$ alkoxy-$C_{1-4}$-alkyl, $C_{1-4}$ alkylamino, $C_{6-10}$ arylamino, $C_{6-10}$ aryloxy, $C_{1-9}$ heteroaryl, $C_{1-9}$ heteroaryloxy, $C_{2-6}$ alkenyl or $C_{2-10}$ heterocyclyl;

each $R^6$ is independently H, $C_{1-4}$ alkyl, $C_{1-4}$ haloalkyl, $C_{1-4}$ hydroxyalkyl, $C_{1-4}$ amnioalkyl, $C_{1-6}$ alkoxy-$C_{1-6}$ alkylamino-$C_{1-4}$-alkyl, $C_{6-10}$ aryl-$C_{1-4}$-alkyl, $C_{6-10}$ aryl, $C_{2-10}$ heterocylyl or $C_{3-8}$ cycloalkyl; and each $n_1$ and $n_2$ is independently 1, 2, 3 or 4.

In some embodiments, the compound having formula (II):

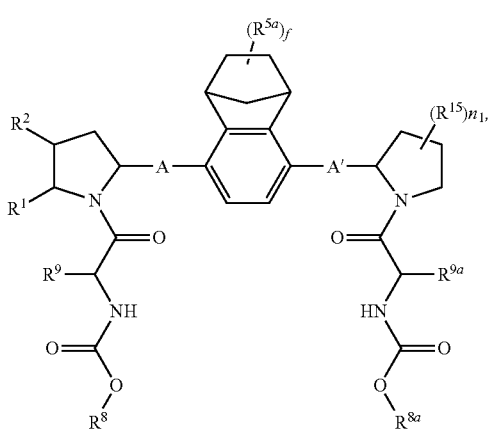

(II)

wherein each of A and A' is independently

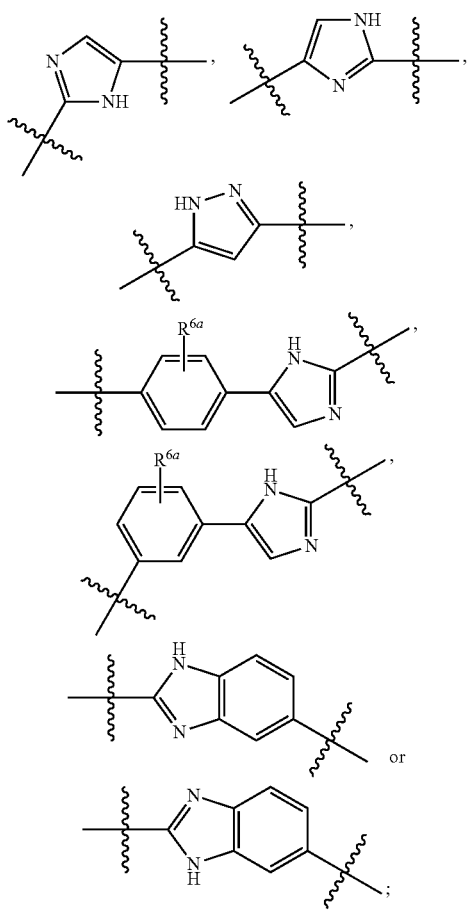

$R^1$ is methyl, ethyl, i-propyl, or phenyl;
$R^2$ is H, deuterium, methyl, ethyl, i-propyl, or phenyl;
each $R^{5a}$ is independently H, deuterium, oxo (=O), —$CF_3$, methyl, ethyl, phenyl, benzyl, F, Cl, Br or I;
each $R^{6a}$ is independently H, deuterium, oxo (=O), hydroxy, amino, F, Cl, Br, I, cyano, methyl, ethyl, i-propyl, cyclohexyl, phenyl, benzyl, —$CF_3$, —$OCF_3$, mercapto, nitro, $C_{1-3}$ alkylamino or $C_{3-8}$ cycloalkyl;
each of $R^8$ and $R^{8a}$ is independently H, deuterium, methyl, ethyl, phenyl, cyclohexyl, 1-methylpropyl, i-propyl or t-butyl;
each of $R^9$ and $R^{9a}$ is independently H, deuterium, methyl, ethyl, 1-methylpropyl, phenyl, i-propyl, tetrahydropyranyl, or t-butyl;
each $R^{15}$ is independently H, deuterium, F, Cl, Br, I, cyano, hydroxy, methyl, ethyl, methoxylmethyl, i-propyl, i-butyl or phenyl;
$n_1$ is 1, 2, 3 or 4; and
f is 0, 1, 2, 3 or 4.

In another aspect, the present disclosure provides a pharmaceutical composition comprising any one of the above compounds.

In some embodiments, the pharmaceutical composition also comprises a pharmaceutically acceptable carrier, excipient, diluent, adjuvant, vehicle or a combination thereof.

In some embodiments, the pharmaceutical composition disclosed herein further comprises an anti-HCV agent.

In other embodiments, the anti-HCV agent is interferon, ribavirin, IL-2, IL-6, IL-12, a compound that enhances the development of a type 1 helper T cell response, interfering RNA, anti-sense RNA, imiquimod, an inosine-5'-monophosphate dehydrogenase inhibitor, amantadine, rimantadine, bavituximab, a HCV neutralizing polyclonal antibody (CIVACIR®), boceprevir, telaprevir, erlotinib, daclatasvir, simeprevir, asunaprevir, vaniprevir, faldaprevir, paritaprevir, danoprevir, sovaprevir, grazoprevir, vedroprevir, BZF-961, GS-9256, narlaprevir, ANA-975, ombitasvir, EDP-239, PPI-668, velpatasvir, samatasvir, elbasvir, MK-8325, GSK-2336805, PPI-461, BI-2013335, ciluprevir, ACH-1095, VX-985, IDX-375, VX-500, VX-813, PHX-1766, PHX-2054, IDX-136, IDX-316, modithromycin, VBY-376, TMC-649128, mericitabine, sofosbuvir, INX-189, IDX-184, IDX102, R-1479, UNX-08189, PSI-6130, PSI-938, PSI-879, nesbuvir, HCV-371, VCH-916, lomibuvir, MK-3281, dasabuvir, ABT-072, filibuvir, deleobuvir, tegobuvir, A-837093, JKT-109, G1-59728, GL-60667, AZD-2795, TMC647055, MK-3682, GS-9669, odalasvir, furaprevir, setrobuvir, alisporivir, BIT-225, AV-4025, ACH-3422, MK-2748, MK-8325, JNJ-47910382, ABP-560, TD-6450, TVB-2640, ID-12, PPI-383, A-848837, RG-7795, BC-2125 or a combination thereof.

In other embodiments, the interferon is interferon α-2b, pegylated interferon α, interferon α-2a, pegylated interferon α-2a, consensus interferon-α, interferon γ or a combination thereof.

In other embodiments, the pharmaceutical composition disclosed herein further comprises at least one HCV inhibitor, other than the compound disclosed herein, for inhibiting the HCV replication process, a function of a HCV viral protein, or a combination thereof; the HCV replication process disclosed herein is a viral cycle comprises of HCV entry, HCV uncoating, HCV translation, HCV replication, HCV assembly and HCV egress. The HCV viral protein disclosed herein further is a metalloproteinase, non-structural protein NS2, NS3, NS4A, NS4B, NS5A or NS5B, or an internal ribosome entry site (IRES) or inosine-5'-monophosphate dehydrogenase (IMPDH) required in HCV viral replication.

In another aspect, use of the compound or the pharmaceutical composition in inhibiting the HCV replication process, a function of a HCV viral protein function, and a combination thereof; the HCV replication process disclosed herein further comprises HCV entry, HCV uncoating, HCV translation, HCV replication, HCV assembly and HCV egress. The HCV viral protein disclosed herein further is a metalloproteinase, non-structural protein NS2, NS3, NS4A, NS4B, NS5A or NS5B, or an internal ribosome entry site (IRES) or inosine-5'-monophosphate dehydrogenase (IMPDH) required in HCV viral replication.

In another aspect, use of the compound or the pharmaceutical composition disclosed herein for preventing, managing, treating or lessening the severity of HCV infection and a HCV disorder in a patient is provided, which comprises administering a therapeutically effective amount of the (a) compound or pharmaceutical composition disclosed herein to the patient.

In another aspect, a compound or the pharmaceutical composition disclosed herein for use in inhibiting the HCV replication process, a function of a HCV viral protein, or a combination thereof; the HCV replication process disclosed herein comprises HCV entry, HCV uncoating, HCV translation, HCV replication, HCV assembly and HCV egress; the HCV viral protein disclosed herein is metalloproteinase, non-structural protein NS2, NS3, NS4A, NS4B, NS5A or NS5B, or an internal ribosome entry site (IRES) or inosine-5'-monophosphate dehydrogenase (IMPDH) required in HCV viral replication.

In another aspect, a compound or the pharmaceutical composition disclosed herein for use in preventing, managing, treating or lessening the severity of HCV infection and a HCV disorder in a patient is provided, which comprises administering a therapeutically effective amount of the (a) compound or pharmaceutical composition disclosed herein to the patient.

In another aspect, a method of inhibiting the HCV replication process a function of a HCV viral protein or a combination thereof; the HCV replication process disclosed herein comprises HCV entry, HCV uncoating, HCV translation, HCV replication, HCV assembly and HCV egress; the HCV viral protein disclosed herein is a metalloproteinase, non-structural protein NS2, NS3, NS4A, NS4B, NS5A or NS5B, or an internal ribosome entry site (IRES) or inosine-5'-monophosphate dehydrogenase (IMPDH) required in HCV viral replication.

In another aspect, a method of preventing, managing, treating or lessening the severity of HCV infection and a HCV disorder with a compound or the pharmaceutical composition disclosed herein in a patient is provided, which comprises administering a therapeutically effective amount of the (a) compound or pharmaceutical composition disclosed herein to the patient.

In another aspect, provided herein include methods of preparing, methods of separating, and methods of purifying compounds of Formula (I) or (II).

The foregoing merely summarizes certain aspects disclosed herein and is not intended to be limiting in nature. These aspects and other aspects and embodiments are described more fully below.

DETAILED DESCRIPTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

It is further appreciated that certain features of the invention, which are, for clarity, described in the context of separate embodiments, can also be provide in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated. For purposes disclosed herein, the chemical elements are identified in accordance with the Periodic Table of the Elements, CAS version, and the *Handbook of Chemistry and Physics, 75th* Ed. 1994. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, New York: 2007, all of which are incorporated herein by reference in their entireties.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

The term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

The term "comprising" is meant to be open ended, including the indicated component but not excluding other elements.

"Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Chiral" refers to molecules which have the property of non-superimposability of the mirror image partner, while the term "achiral" refers to molecules which are superimposable on their mirror image partner.

"Enantiomers" refer to two stereoisomers of a compound which are non-superimposable mirror images of one another.

"Diastereomer" refers to a stereoisomer with two or more centers of chirality and whose molecules are not mirror images of one another. Diastereomers have different physical properties, e.g. melting points, boiling points, spectral properties or biological activities. Mixtures of diastereomers may separate under high resolution analytical procedures such as electrophoresis and chromatography such as HPLC.

Stereochemical definitions and conventions used herein generally follow Parker et al., McGraw-Hill Dictionary of Chemical Terms (1984) McGraw-Hill Book Company, New York and Eliel et al., "Stereochemistry of Organic Compounds", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); Principles of Asymmetric Synthesis ($2^{nd}$ Ed. Robert et al., Elsevier, Oxford, UK, 2012); Eliel et al., Stereochemistry of Carbon Compounds (McGraw-Hill, NY, 1962); and Wilen et al., Tables of Resolving Agents and Optical Resolutions p. 268 (E. L. Eliel, Ed., Univ. of Notre Dame Press, Notre Dame, Ind., 1972). Chiral Separation Techniques: A Practical Approach (Subramanian, G Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

As described herein, compounds disclosed herein may optionally be substituted with one or more substituents, such as those illustrated below, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

Furthermore, what need to be explained is that the phrases "each . . . and . . . is independently", "each of . . . and . . . is independently" are used interchangeably. It should be broadly understood that the specific options expressed by the same symbol are variable independently of each other in different groups; or the specific options expressed by the same symbol are variable independently of each other in same groups.

Unless otherwise defined herein, for a variable that occurs more than one time in any substituent or in the compound of the invention or any other formulae herein, its definition on each occurrence is independent of its definition at every other occurrence. Combinations of substituents are permissible only if such combinations result in stable compound. Stable compounds are compounds which can be isolated in a useful degree of purity from a reaction mixture.

At various places in the present specification, substituents of compounds disclosed herein are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon radical of 1 to 20 carbon atoms, wherein the alkyl radical may be optionally substituted independently with one or more substituents described below. Unless otherwise specified, the alkyl group contains 1-20 carbon atoms. In one embodiment, the alkyl group contains 1-12 carbon atoms. In another embodiment, the alkyl group contains 1-6 carbon atoms. In still another embodiment, the alkyl group contains 1-4 carbon atoms. In yet another embodiment, the alkyl group contains 1-3 carbon atoms.

Some non-limiting examples of the alkyl group include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, 1-heptyl, 1-octyl, and the like.

The term "alkylene" refers to a saturated divalent hydrocarbon group derived from a straight or branched saturated hydrocarbon chain by the removal of two hydrogen atoms. Unless otherwise specified, the alkylene group contains 1-12 carbon atoms. In one embodiment, the alkylene group contains 1-6 carbon atoms. In another embodiment, the alkylene group contains 1-4 carbon atoms. In still another embodiment, the alkylene group contains 1-3 carbon atoms. In yet another embodiment, the alkylene group contains 1-2 carbon atoms. The alkylene group is exemplified by methylene (—$CH_2$—), ethylene (—$CH_2CH_2$—), isopropylene (—CH($CH_3$)$CH_2$—), and the like.

The term "alkenyl" refers to a linear or branched-chain monovalent hydrocarbon radical of 2 to 12 carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. In one embodiment, the alkenyl group contains 2-8 carbon atoms. In another embodiment, the alkenyl group contains 2-6 carbon atoms. In still another embodiment, the alkenyl group contains 2-4 carbon atoms. Some non-limiting examples of the alkenyl group include ethylenyl or vinyl (—CH═$CH_2$), allyl (—$CH_2$CH═$CH_2$), and the like.

The term "alkynyl" refers to a linear or branched-chain monovalent hydrocarbon radical of 2 to 12 carbon atoms with at least one site of unsaturation, i.e., a carbon-carbon, sp triple bond, wherein the alkynyl radical may be optionally substituted independently with one or more substituents described herein. In one embodiment, the alkynyl group contains 2-8 carbon atoms. In another embodiment, the alkynyl group contains 2-6 carbon atoms. In still another embodiment, the alkynyl group contains 2-4 carbon atoms. Some non-limiting examples of the alkynyl group include ethynyl (—C≡CH), propargyl (—$CH_2$C≡CH), propynyl (—C≡C—$CH_3$), and the like.

The term "heteroalkyl" refers to alkyl chain inserted into one or more heteroatoms, wherein, alkyl and heteroatom are as defined herein. Unless otherwise specified, the heteroalkyl group contains 2-20 carbon atoms. In one embodiment, the heteroalkyl group contains 2-8 carbon atoms. In other embodiment, the heteroalkyl group contains 2-6 carbon atoms. In still another embodiment, the heteroalkyl group contains 2-4 carbon atoms. In yet another embodiment, the heteroalkyl group contains 2-3 carbon atoms. Some non-limiting examples of the heteroalkyl group include $CH_3OCH_2$—, $CH_3CH_2OCH_2$—, $CH_3SCH_2$—, ($CH_3$)$_2NCH_2$—, ($CH_3$)$_2CH_2OCH_2$—, $CH_3OCH_2CH_2$—, $CH_3CH_2OCH_2CH_2$—, and the like.

The term "alkenylene" refers to an unsaturated divalent hydrocarbon group derived from a straight or branched-chain unsaturated hydrocarbon alkene by the removal of two hydrogen atoms. The alkenylene group is optionally substituted with one or more substituents. The substituents include, but are not limited to, deuterium, hydroxy, amino, halo, cyano, aryl, heteroaryl, alkoxy, alkyl, alkenyl, alkynyl, heterocyclyl, mercapto, nitro, or aryloxy. Some non-limiting examples of the alkenylene group include ethenylene (—CH═CH—), isopropenylene (—C(CH₃)═CH—), 3-methoxy-1,1-propenylidene, 2-methyl-1,1-butenylidene, etc.

The term "carbocyclylene" or "cycloalkylene" refers to a saturated divalent hydrocarbon ring derived from a monocyclic ring having 3 to 12 carbon atoms or a bicyclic ring having 7 to 12 carbon atoms by the removal of two hydrogen atoms, wherein the carbocyclyl group or the cycloalkyl group is as defined herein. Some non-limiting examples of the cycloalkylene group include cyclopropylene, cyclobutylene, cyclopentylene, cyclohexylene, 1-cyclopent-1-enylene, 1-cyclopent-2-enylene, etc.

The term "heterocyclylene" refers to a non-aromatic monocyclic, bicyclic, or tricyclic ring system in which one or more ring members are an independently selected heteroatom and that is completely saturated or that contains one or more units of unsaturation that has two points of attachment to the rest of the molecule, wherein the heterocyclyl group is as defined herein. Some non-limiting examples of the heterocyclylene group include piperidin-1,4-ylene, piperazin-1,4-ylene, tetrahydrofuran-2,4-ylene, tetrahydrofuran-3,4-ylene, azetidin-1,3-ylene, pyrrolidin-1,3-ylene, etc.

The term "alkoxy" refers to an alkyl group, as previously defined, attached to the principal carbon atom through an oxygen atom. Unless otherwise specified, the alkoxy group contains 1-12 carbon atoms. In one embodiment, the alkoxy group contains 1-6 carbon atoms. In another embodiment, the alkoxy group contains 1-4 carbon atoms. In still another embodiment, the alkoxy group contains 1-3 carbon atoms. The alkoxy radical may be optionally substituted with one or more substituents described herein.

Some non-limiting examples of alkoxy groups include methoxy (MeO, —OCH₃), ethoxy (EtO, —OCH₂CH₃), 1-propoxy (n-PrO, n-propoxy, —OCH₂CH₂CH₃), 2-propoxy (i-PrO, i-propoxy, —OCH(CH₃)₂), 1-butoxy (n-BuO, n-butoxy, —OCH₂CH₂CH₂CH₃), 2-methyl-1-propoxy (i-BuO, i-butoxy, —OCH₂CH(CH₃)₂), 2-butoxy (s-BuO, s-butoxy, —OCH(CH₃)CH₂CH₃), 2-methyl-2-propoxy (t-BuO, t-butoxy, —OC(CH₃)₃), 1-pentoxy (n-pentoxy, —OCH₂CH₂CH₂CH₂CH₃), 2-pentoxy (—OCH(CH₃)CH₂CH₂CH₃), 3-pentoxy (—OCH(CH₂CH₃)₂), 2-methyl-2-butoxy (—OC(CH₃)₂CH₂CH₃), 3-methyl-2-butoxy (—OCH(CH₃)CH(CH₃)₂), 3-methyl-1-butoxy (—OCH₂CH₂CH(CH₃)₂), 2-methyl-1-butoxy (—OCH₂CH(CH₃)CH₂CH₃), and the like.

The term "haloalkyl", "haloalkenyl" or "haloalkoxy" refers to alkyl, alkenyl, or alkoxy, as the case may be, substituted with one or more halogen atoms. Some non-limiting examples of "haloalkyl", "haloalkenyl" or "haloalkoxy" groups include trifluoromethyl, trifluoromethoxy, etc.

The term "hydroxyalkyl" or "hydroxy-substituted alkyl" refers to an alkyl group substituted with one or more hydroxy groups, wherein the alkyl group is as defined herein. Some non-limiting examples of the hydroxyalkyl group include hydroxymethyl, hydroxyethyl, 1,2-dyhydroxyethyl, etc.

The term "carbocycle", "carbocyclyl" or "carbocyclic ring" refers to a monovalent or multivalent non-aromatic, saturated or partially unsaturated ring having 3 to 12 carbon atoms as a monocyclic, bicyclic or tricyclic ring system. A carbobicyclyl system includes a spiro carbobicyclyl and a fused carbobicyclyl. Suitable carbocyclyl groups include, but are not limited to, cycloalkyl, cycloalkenyl, and cycloalkynyl. Further non-limiting examples of carbocyclyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cyclohendecyl, cyclododecyl, and the like.

The term "cycloalkyl" refers to a monovalent or multivalent saturated ring having 3 to 12 carbon atoms as a monocyclic, bicyclic, or tricyclic ring system. In one embodiment, the cycloalkyl contains 3-12 carbon atoms. In another embodiment, the cycloalkyl contains 3-8 carbon atoms. In still another embodiment, the cycloalkyl contains 3-6 carbon atoms. The cycloalkyl radical may be optionally substituted with one or more substituents described herein.

The term "heterocycle", "heterocyclyl", or "heterocyclic ring" as used interchangeably herein refers to a saturated or partially unsaturated monocyclic, bicyclic or tricyclic ring containing 3-12 ring atoms of which at least one ring atom is selected from nitrogen, sulfur and oxygen, and which may, unless otherwise specified, be carbon or nitrogen linked, and of which a —CH₂— group can optionally be replaced by a —C(═O)— group. Ring sulfur atoms may be optionally oxidized to form S-oxides. Ring nitrogen atoms maybe optionally oxidized to form N-oxides. Examples of heterocyclyl include, but are not limited to, oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, indolinyl, 1,2,3,4-tetrahydroisoquinolinyl, 1,3-benzodioxolyl, 2-oxa-5-azabicyclo[2.2.1]hept-5-yl. Some non-limited examples of heterocyclyl wherein —CH₂— group is replaced by —C(═O)— moiety are 2-oxopyrrolidinyl, oxo-1,3-thiazolidinyl, 2-piperidinonyl, 3,5-dioxopiperidinyl and pyrimidinedionyl. Some non-limited examples of heterocyclyl wherein the ring sulfur atom is oxidized are sulfolanyl, 1,1-dioxo-thiomorpholinyl. The heterocyclyl group may be optionally substituted with one or more substituents described herein.

In one embodiment, heterocyclyl may be a 4-7 membered heterocyclyl, which refers to a saturated or partially unsaturated monocyclic ring containing 4-7 ring atoms, of which at least one ring atom is selected from nitrogen, sulfur and oxygen, and of which may, unless otherwise specified, be carbon or nitrogen linked, and of which a —CH₂— group can optionally be replaced by a —C(═O)— group. Ring sulfur atoms may be optionally oxidized to form S-oxides. Ring nitrogen atoms maybe optionally oxidized to form N-oxides. Examples of 4-7 membered heterocyclyl include, but are not limited to, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl. Some non-limited examples of heterocyclyl wherein —CH₂— group is replaced by —C(═O)— moiety are 2-oxopyrrolidinyl, oxo-1,3-thiazolidinyl, 2-piperidinonyl, 3,5-dioxopiperidinyl and pyrimidinedionyl. Some non-limited examples of heterocyclyl wherein the ring sulfur atom is oxidized are sulfolanyl, 1,1-dioxo-thiomorpholinyl. The 4-7 membered heterocyclyl group may be optionally substituted with one or more substituents described herein.

In another embodiment, heterocyclyl may be a 4 membered heterocyclyl, which refers to a saturated or partially unsaturated monocyclic ring containing 4 ring atoms, of which at least one ring atom is selected from nitrogen, sulfur and oxygen, and of which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Examples of 4 membered heterocyclyl group include, but are not limited to, azetidinyl, oxetanyl, thietanyl, and the like. The 4 membered heterocyclyl group may be optionally substituted with one or more substituents described herein.

In yet another embodiment, heterocyclyl refers to a 5 membered heterocyclyl, which refers to a saturated or partially unsaturated monocyclic ring containing 5 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Examples of 5 membered heterocyclyl include, but are not limited to, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl. Some non-limited examples of heterocyclyl wherein —CH$_2$— group is replaced by —C(=O)— moiety are 2-oxopyrrolidinyl, oxo-1,3-thiazolidinyl. Some non-limited examples of heterocyclyl wherein the ring sulfur atom is oxidized is sulfolanyl. The 5 membered heterocyclyl group may be optionally substituted with one or more substituents described herein.

In another embodiment, heterocyclyl refers to a 6 membered heterocyclyl, which refers to a saturated or partially unsaturated monocyclic ring containing 6 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Examples of 6 membered heterocyclyl include, but are not limited to, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl. Some non-limited examples of heterocyclyl wherein —CH$_2$— group is replaced by —C(=O)— moiety are 2-piperidinonyl, 3,5-dioxopiperidinyl and pyrimidinedionyl. Some non-limited examples of heterocyclyl wherein the ring sulfur atom is oxidized is 1,1-dioxothiomorpholinyl. The 6 membered heterocyclyl group may be optionally substituted with one or more substituents described herein.

In yet another embodiment, heterocyclyl refers to a 7-12 membered heterocyclyl, which refers to a saturated or partially unsaturated spiro or fused heterobicyclyl ring containing 7-12 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Examples of 7-12 membered heterocyclyl include, but are not limited to, indolinyl, 1,2,3,4-tetrahydroisoquinolinyl, 1,3-benzodioxolyl, 2-oxa-5-azabicyclo[2.2.1]hept-5-yl. The 7-12 membered heterocyclyl group may be optionally substituted with one or more substituents described herein.

The terms "fused bicyclic ring", "fused cyclic", "fused bicyclyl" and "fused cyclyl" are used interchangeably refer to a monovalent or multivalent saturated or partially unsaturated bridged ring system, but not aromatic bicyclic ring system, and such that two rings share one common bond. Such a system may contain isolated or conjugated unsaturation, but not aromatic or heteroaromatic rings in its core structure (but may have aromatic substitution thereon).

The terms "spirocyclyl", "spirocyclic", "spiro bicyclyl" and "spiro bicyclic" are used interchangeably and refer to a monovalent or multivalent, saturated or partially unsaturated, but not aromatic ring system wherein a ring originating from a particular annular carbon of another ring. For example, as depicted below in Figure a, a saturated ring system (ring B and B') is termed as "fused bicyclyl", whereas ring A and ring B share an atom between the two saturated ring system, which terms as a "spirocyclyl" or "spiro bicyclyl". Each ring in the fused bicyclyl or the spiro bicyclyl can be either a carbocyclyl or a heterocyclyl, and each ring is optionally substituted independently with one or more substituents described herein.

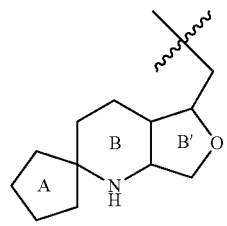

Figure a

The term "heterocycloalkyl" refers to a monovalent or multivalent saturated ring having 3 to 12 ring atoms as a monocyclic, bicyclic, or tricyclic ring system in which at least one ring atom is selected from nitrogen, sulfur and oxygen.

The term "n membered" where n is an integer typically describes the number of ring-forming atoms in a moiety where the number of ring-forming atoms is n. For example, piperidinyl is an example of a 6 membered heterocycloalkyl and 1,2,3,4-tetrahydro-naphthalene is an example of a 10 membered cycloalkyl group.

The term "unsaturated" refers to a moiety having one or more units of unsaturation.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" refers to Fluoro (F), Chloro (Cl), Bromo (Br), or Iodo (I).

The term "aryl" refers to monocyclic, bicyclic, and tricyclic carbocyclic ring systems having a total of 6 to 14 ring members, preferably, 6 to 12 ring members, and more preferably 6 to 10 ring members, wherein at least one ring in the system is aromatic, wherein each ring in the system contains 3 to 7 ring members and that has one or more points of attachment to the rest of the molecule. The term "aryl" may be used interchangeably with the term "aryl ring" or "aromatic ring". Some non-limiting examples of the aryl group would include phenyl, naphthyl, and anthracene. The aryl radical is optionally substituted independently with one or more substituents described herein.

The term "heteroaryl" or "heteroaromatic ring" refers to monocyclic, bicyclic, and tricyclic ring systems having a total of 5 to 12 ring members, preferably, 5 to 10 ring members, and more preferably 5 to 6 ring members, wherein at least one ring in the system is aromatic, at least one ring in the system contains one or more heteroatoms, wherein each ring in the system contains 5 to 7 ring members and that has one or more points of attachment to the rest of the molecule. The term "heteroaryl" may be used interchangeably with the term "heteroaryl ring" or the term "heteroaromatic ring". The heteroaryl radicals are optionally substituted independently with one or more substituents described herein. In one embodiment, a 5-10 membered heteroaryl comprises 1, 2, 3 or 4 heteroatoms independently selected from O, S and N. The heteroaryl radical is optionally substituted independently with one or more substituents described herein.

Some non-limiting examples of the heteroaryl group include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl and [1,2,4]triazolo[1,5-a]pyridyl, and the like.

The term "carboxy" or "carboxyl", whether used alone or with other terms, such as "carboxyalkyl", refers to —CO$_2$H. The term "carbonyl", whether used alone or with other terms, such as "aminocarbonyl" or "carbonyloxy", refers to —(C=O)—.

The term "alkylamino" embraces "N-alkylamino" and "N,N-dialkylamino" where amino groups are independently substituted with one alkyl radical or with two alkyl radicals, respectively. Some non-limiting examples of alkylamino radicals are "lower alkylamino" radicals having one or two alkyl radicals of one to six carbon atoms, attached to a nitrogen atom. Some other non-limiting examples of alkylamino radicals are"lower alkylamino" radicals of one to three carbon atoms, attached to a nitrogen atom. Suitable alkylamino radicals may be mono or dialkylamino such as N-methylamino, N-ethylamino, N,N-dimethylamino, N,N-diethylamino and the like.

The term "arylamino" refers to amino groups, which have been substituted with one or two aryl radicals. Examples of arylamino include, but are not limited to N-phenylamino. The arylamino radicals may be further substituted on the aryl ring portion of the radical.

The term "aminoalkyl" refers to linear or branched alkyl radicals having one to about ten carbon atoms any one of which may be substituted with one or more amino radicals. More preferred aminoalkyl radicals are "lower aminoalkyl" radicals having 1-6 carbon atoms and one or more amino radicals. Examples of such radicals include aminomethyl, aminoethyl, aminopropyl, aminobutyl and aminohexyl.

As described herein, a bond drawn from a substituent to the center of one ring within a ring system (as shown below (a)) represents substitution of the substituent $(R^{5a})_f$ at any substitutable position on the rings (W, W$_1$ and W$_2$) to which it is attached. For example, Formula (a) represents possible substitution in any of the positions on the W$_1$, W$_2$, and W ring.

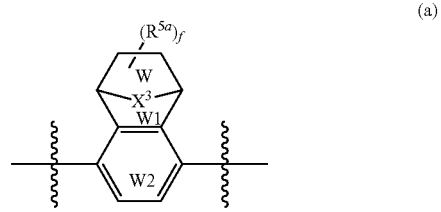

(a)

As described herein, two attaching points either E or E', within a ring system (as shown in Formula (b)), attach to the rest of the molecule, e.g., E and E' may be used interchangeably with each other.

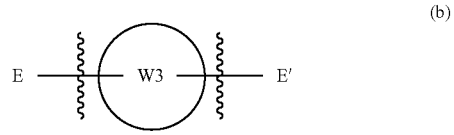

(b)

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (BOC, Boc), benzyloxycarbonyl (CBZ, Cbz) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of common carboxy-protecting group include —CH$_2$CH$_2$SO$_2$Ph, cyanoethyl, 2-(trimethylsilyl)ethyl, 2-(trimethylsilyl) ethoxymethyl, 2-(p-toluenesulfonyl)ethyl, 2-(p-nitrophenylsulfonyl)ethyl, 2-(diphenyl phosphino)-ethyl, nitroethyl, etc. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

The term "prodrug" refers to a compound that is transformed in vivo into a compound of Formula (I). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi et al., *Pro-drugs as Novel Delivery Systems*, Vol. 14, A.C.S. Symposium Series; Roche, et al. ed., *Bioreversible Carriers in Drug Design*, American Pharmaceutical Association and Pergamon Press, 1987; Rautio et al., Prodrugs: Design and Clinical Applications, *Nat. Rev. Drug Discovery*, 2008, 7, 255-270, and Hecker et al, Prodrugs of Phosphates and Phosphonates, *J. Med. Chem.*, 2008, 51, 2328-2345, all of which are incorporated herein by reference.

A "metabolite" is a product produced through metabolism in the body of a specified compound or salt thereof. The metabolites of a compound may be identified using routine techniques known in the art and their activities determined using tests such as those described herein. Such products may result for example from the oxidation, reduction, hydrolysis, amidation, deamidation, esterification, deesterification, enzyme cleavage, etc, of the administered compound. Accordingly, the invention includes metabolites of compounds disclosed herein, including compounds produced by a process comprising contacting a compound disclosed herein with a mammal for a period of time sufficient to yield a metabolic product thereof.

A "pharmaceutically acceptable salt" refers to organic or inorganic salts of a compound disclosed herein. The pharmaceutically acceptable salts are well known in the art. For example, Berge et al., describe pharmaceutically acceptable salts in detail in *J. Pharmacol Sci*, 1977, 66: 1-19, which is incorporated herein by reference. Some non-limiting examples of the pharmaceutically salt include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, sodium malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, etc. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersible products may be obtained by such quaternization. Representative alkali or alkaline earth metal salts include sodium, lithium, potassium, calcium, magnesium, etc. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Some non-limiting examples of the solvent that form the solvate include water, isopropanol, ethanol, methanol, DMSO, ethyl acetate, acetic acid, and ethanolamine. The term "hydrate" refers to the complex where the solvent molecule is water.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable bases addition salts can be formed with inorganic bases and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002)

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$ (deuterium, D), $^3H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$, $^{125}I$ respectively.

In another aspect, the compounds of the invention include isotopically enriched compounds as defined herein, for example those into which radioactive isotopes, such as $^3H$, $^{14}C$ and $^{18}F$, or those into which non-radioactive isotopes, such as $^2H$ and 13C are present. Such isotopically enriched compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, d6-acetone, DMSO-$d_6$.

In another aspect, provided herein include intermediate of compounds of Formula (I).

In another aspect, provided herein include methods of preparing, methods of separating, and methods of purifying compounds of Formula (I).

In another aspect, provided herein is a pharmaceutical composition comprising the compound disclosed herein, and a pharmaceutically acceptable carrier, excipient, diluents, adjuvant, menstruum or a combination thereof. In some embodiments, the composition is a liquid, solid, semi-solid, gel, or an aerosol form.

By "combination", there is meant either a fixed combination in one dosage unit form, or a kit of parts for the combined administration where a compound disclosed herein and a combination partner may be administered independently at the same time or separately within time intervals that especially allow that the combination partners show a cooperative, e.g., synergistic, effect or any combination thereof. The terms "coadministration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a combination partner, are both administered to a patient simultaneously in the form of a single entity or dosage. The term "non-fixed combination" means that the active ingredients, e.g. a compound disclosed herein and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

It should be noted that the term of "inhibiting HCV viral protein" should be broadly understood, which comprises inhibiting the expression level of HCV viral protein, inhibiting activity level of HCV viral protein, viral assembly and egress level. The expression level of HCV protein includes but not limited to translation level of the viral protein, posttranslational modification level of the viral protein, replication level of genetic material in offsprings and so on.

Description of Compounds of the Invention

Provided herein are bridged ring compounds, and pharmaceutical formulations thereof, that are useful in inhibiting HCV infection, especially inhibiting the activity of the non-structural 5A ("NS5A") protein In one aspect, provided herein are compounds having Formula (I), or a stereoisomer, a geometry, a tautomer, an N-oxide, a hydrate, a solvate, a metabolite, a pharmaceutically acceptable salt or a prodrug thereof:

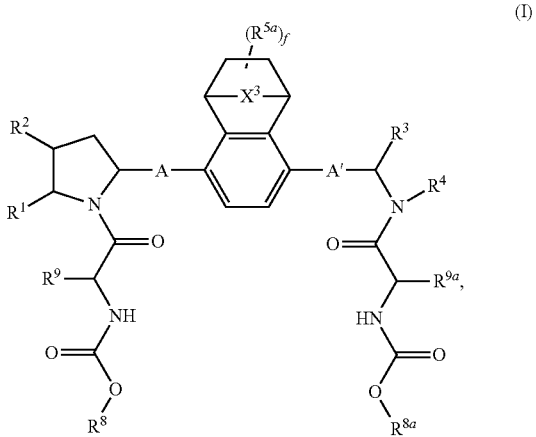

wherein $X^3$ is O, S, $NR^6$ or $(CR^7R^{7a})_e$;
e is 1, 2, 3 or 4;
each of A and A' is independently a bond, $C_{1-3}$ alkylene, $C_{2-4}$ alkenylene, $C_{3-8}$ cycloalkylene, $C_{2-10}$ heterocycloalkylene, or each of A and A' is independently

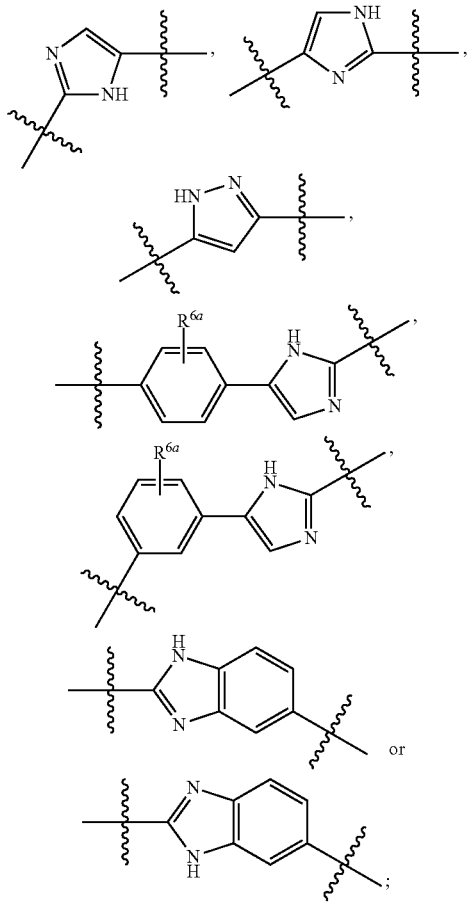

$R^1$ is $C_{1-4}$ alkyl, $C_{1-4}$ heteroalkyl or $C_{6-10}$ aryl;
$R^2$ is H, deuterium, $C_{1-4}$ alkyl, $C_{1-4}$ heteroalkyl or $C_{6-10}$ aryl;
each of $R^3$ and $R^4$ is independently H, deuterium, $C_{1-4}$ alkyl, $C_{1-4}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-4}$-alkyl, $C_{1-4}$ alkoxy, or $R^3$ and $R^4$, together with the N—CH to which they are attached, form a 3-8 membered heterocycle, a 3-8 membered carbocycle, a $C_{5-12}$ fused bicycle or a $C_{5-12}$ spiro bicycle; wherein each of the $C_{1-4}$ alkyl, $C_{1-4}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-4}$-alkyl, $C_{1-4}$ alkoxy, 3-8 membered heterocycle, 3-8 membered carbocycle, $C_{5-12}$ fused bicycle and $C_{5-12}$ spiro bicycle is optionally and independently substituted with one or more substituents independently selected from deuterium, hydroxy, amino, oxo (=O), F, Cl, Br, I, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{1-6}$ alkoxy, $C_{1-6}$ alkylamino, $C_{6-10}$ aryl, $C_{6-10}$ aryloxy, $C_{6-10}$ arylamino, $C_{1-9}$ heteroaryl, $C_{1-9}$ heteroaryloxy, $C_{2-6}$ alkenyl, $C_{3-10}$ cycloalkyl or $C_{2-10}$ heterocyclyl;
each $R^{5a}$ and $R^{6a}$ is independently H, deuterium, oxo (=O), hydroxy, amino, F, Cl, Br, I, cyano, mercapto, nitro, $C_{1-6}$ alkoxy, $C_{1-6}$ alkyl, $C_{6-10}$ aryl, —$CF_3$, —$OCF_3$, $C_{1-6}$ alkylamino, $C_{3-10}$ cycloalkyl or $C_{6-10}$ aryloxy;
$R^6$ is H, deuterium, $C_{1-6}$ alkyl, $C_{1-6}$ alkoxy-$C_{1-6}$-alkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryl, $C_{1-9}$ heteroaryl, $C_{2-10}$ heterocyclyl or $C_{3-8}$ carbocyclyl;
each $R^7$, $R^{7a}$, $R^9$ and $R^{9a}$ is independently H, deuterium, $C_{1-6}$ alkyl, $C_{1-6}$ alkoxy-$C_{1-6}$-alkyl, $C_{1-6}$ haloalkyl, $C_{1-6}$ hydroxyalkyl, $C_{1-6}$ heteroalkyl, $C_{1-6}$ alkylamino-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-8}$ cycloalkyl-$C_{1-6}$-alkyl, $C_{6-10}$ aryl, $C_{1-9}$ heteroaryl, $C_{2-10}$ heterocyclyl or $C_{3-8}$ carbocyclyl;
each of $R^8$ and $R^{8a}$ is independently H, deuterium, $C_{1-6}$ alkyl, $C_{1-6}$ haloalkyl, $C_{1-6}$ hydroxyalkyl, $C_{1-6}$ heteroalkyl, $C_{6-10}$ aryl, $C_{2-10}$ heterocyclyl, cycloalkyl, $C_{6-10}$ aryl-$C_{1-6}$-alkyl, heteroaryl-$C_{1-6}$-alkyl, $C_{2-10}$ heterocyclyl-$C_{1-6}$-alkyl or $C_{3-8}$ cycloalkyl-$C_{1-6}$-alkyl; and
f is 0, 1, 2, 3 or 4.
In some embodiments, wherein
$X^3$ is $(CR^7R^{7a})_e$; and
each $R^7$ and $R^{7a}$ is independently H, deuterium, $C_{1-3}$ alkyl, $C_{1-3}$ heteroalkyl, $C_{1-3}$ alkoxy-$C_{1-3}$-alkyl, $C_{1-3}$ alkylamino-$C_{1-3}$-alkyl, $C_{6-10}$ aryl-$C_{1-3}$-alkyl, $C_{2-10}$ heterocyclyl-$C_{1-3}$-alkyl, $C_{3-8}$ cycloalkyl or $C_{6-10}$ aryl. In some embodiments, wherein $R^3$ and $R^4$, together with N—CH to which they are attached, form one of the following groups:

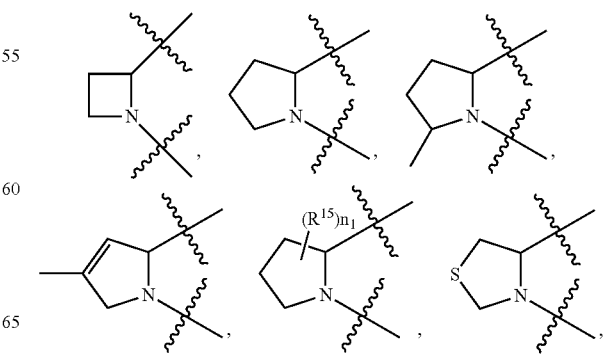

-continued

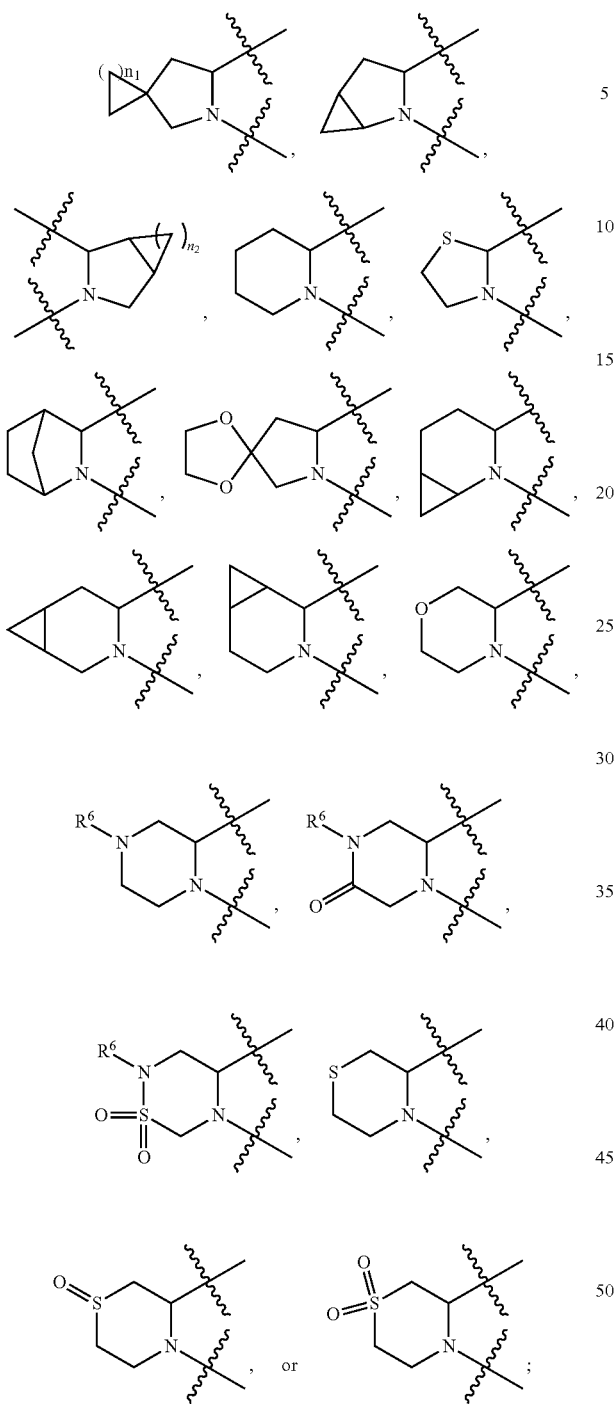

wherein each $R^{15}$ is independently H, deuterium, F, Cl, Br, I, cyano, hydroxy, phenyl, oxo(=O), $C_{1-4}$ alkyl, hydroxyalkyl, $C_{1-4}$ haloalkyl, alkoxy, $C_{1-4}$ alkoxy-$C_{1-4}$-alkyl, $C_{1-4}$ alkylamino, $C_{6-10}$ arylamino, $C_{6-10}$ aryloxy, $C_{1-6}$ heteroaryl, heteroaryloxy, $C_{2-6}$ alkenyl or $C_{2-10}$ heterocyclyl;

each $R^6$ is independently H, $C_{1-4}$ alkyl, $C_{1-4}$ haloalkyl, hydroxyalkyl, amnioalkyl, alkoxy-$C_{1-4}$-alkyl, alkylamino-$C_{1-4}$-alkyl, $C_{6-10}$ aryl-$C_{1-4}$-alkyl, $C_{6-10}$ aryl, $C_{2-10}$ heterocyclyl or $C_{3-8}$ cycloalkyl; and each $n_1$ and $n_2$ is independently 1, 2, 3 or 4.

In some embodiments, the compound having formula (II):

(II)

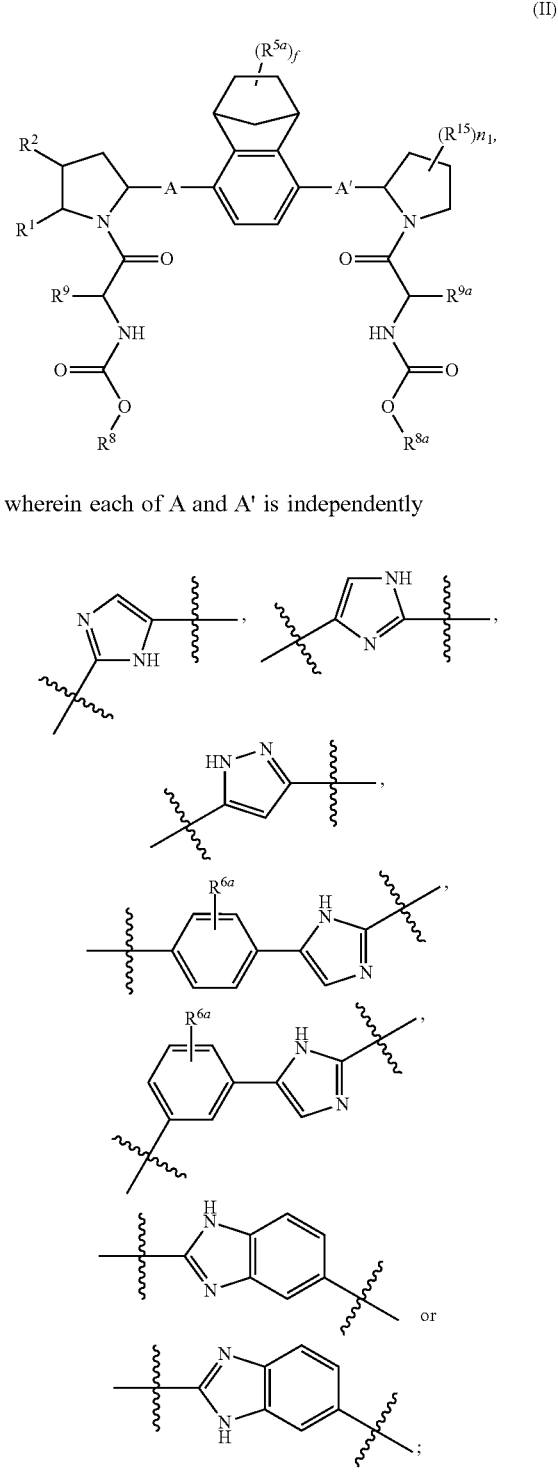

wherein each of A and A' is independently $R^1$ is methyl, ethyl, i-propyl, or phenyl;
$R^2$ is H, deuterium, methyl, ethyl, i-propyl, or phenyl;
each $R^{5a}$ is independently H, deuterium, oxo (=O), —$CF_3$, methyl, ethyl, phenyl, benzyl, F, Cl, Br or I;
each $R^{6a}$ is independently H, deuterium, oxo (=O), hydroxy, amino, F, Cl, Br, I, cyano, methyl, ethyl, i-propyl, cyclohexyl, phenyl, benzyl, —$CF_3$, —$OCF_3$, mercapto, nitro, $C_{1-3}$ alkylamino or $C_{3-8}$ cycloalkyl;

each of $R^8$ and $R^{8a}$ is independently H, deuterium, methyl, ethyl, phenyl, cyclohexyl, 1-methylpropyl, i-propyl or t-butyl;

each of $R^9$ and $R^{9a}$ is independently H, deuterium, methyl, ethyl, 1-methylpropyl, phenyl, i-propyl, tetrahydropyranyl, or t-butyl;

each $R^{15}$ is independently H, deuterium, F, Cl, Br, I, cyano, hydroxy, methyl, ethyl, methoxylmethyl, i-propyl, i-butyl or phenyl;

$n_1$ is 1, 2, 3 or 4; and f is 0, 1, 2, 3 or 4.

In some embodiments, non-limiting examples of compounds disclosed herein, or a stereoisomer, a geometric isomer, a tautomer, an N-oxide, a hydrate, a solvate, or a pharmaceutically acceptable salt thereof, are shown in the following:

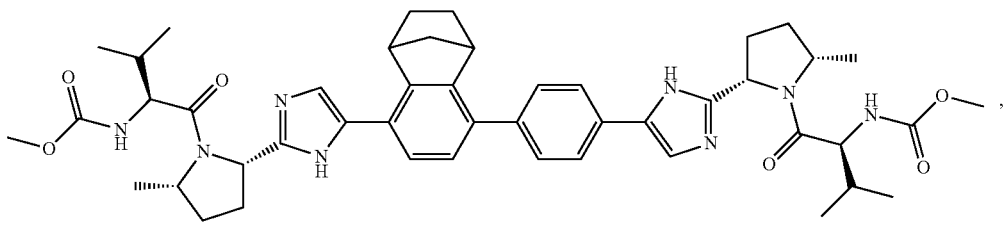

(1)

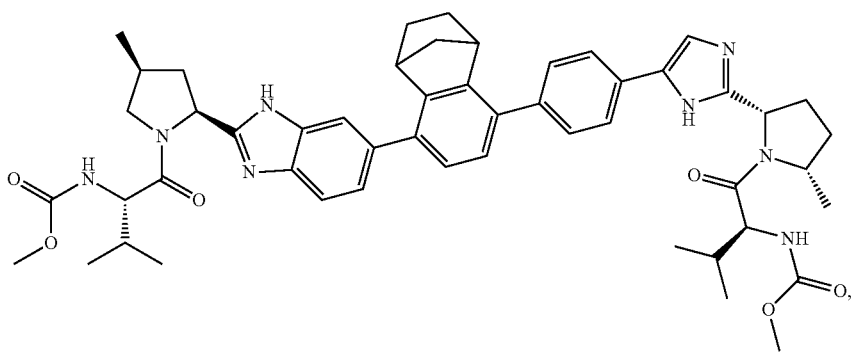

(2)

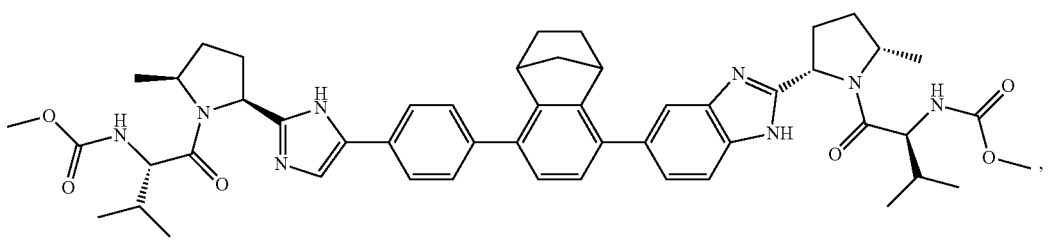

(3)

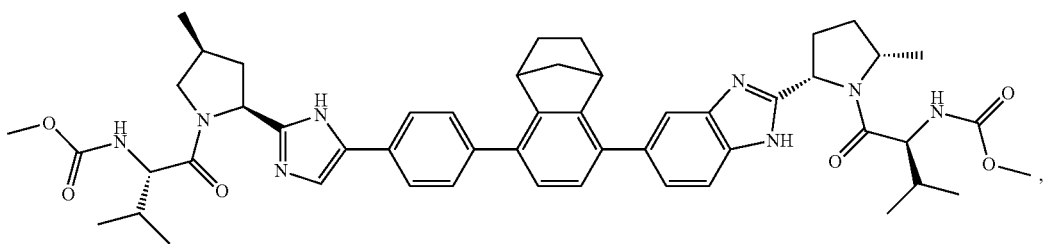

(4)

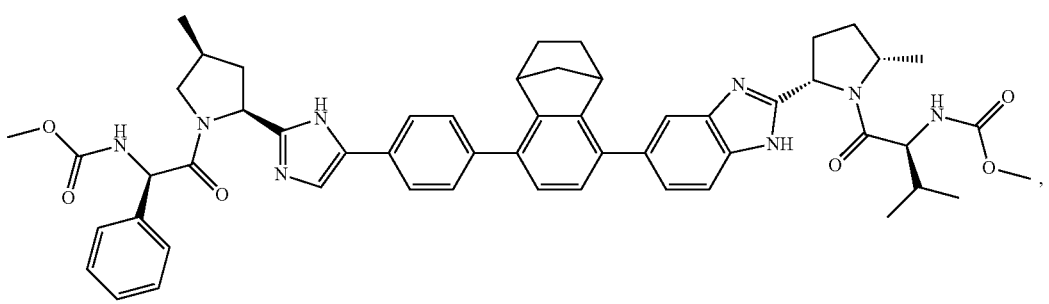

(5)

(6)
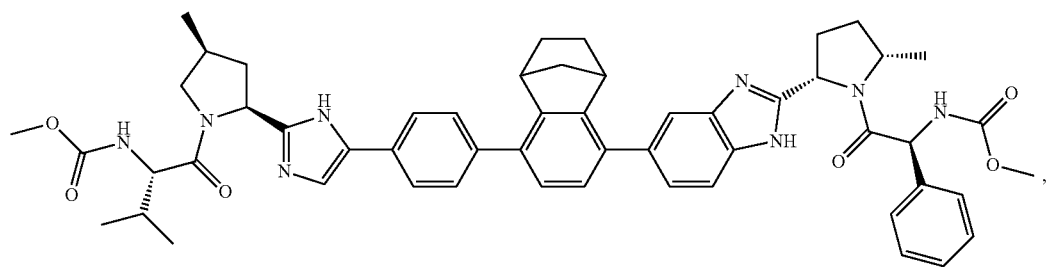
(7)
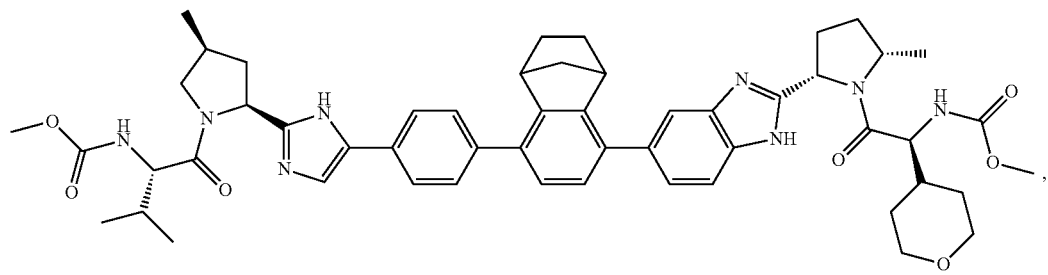
(8)
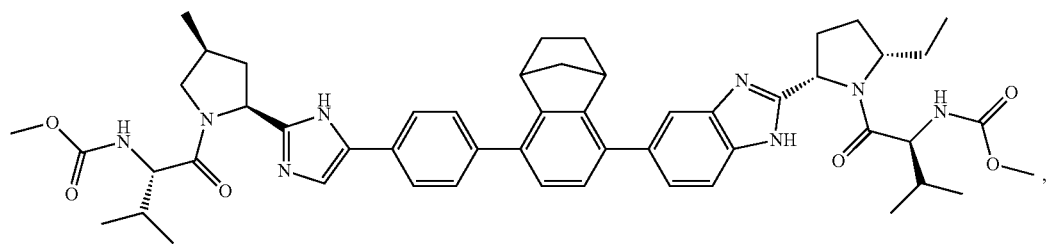
(9)
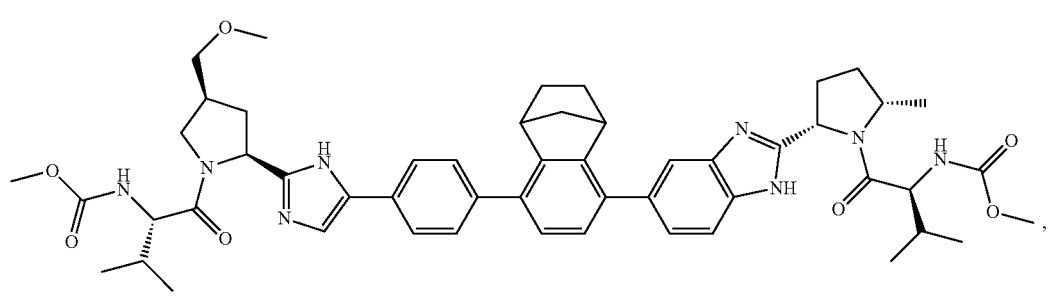
(10)
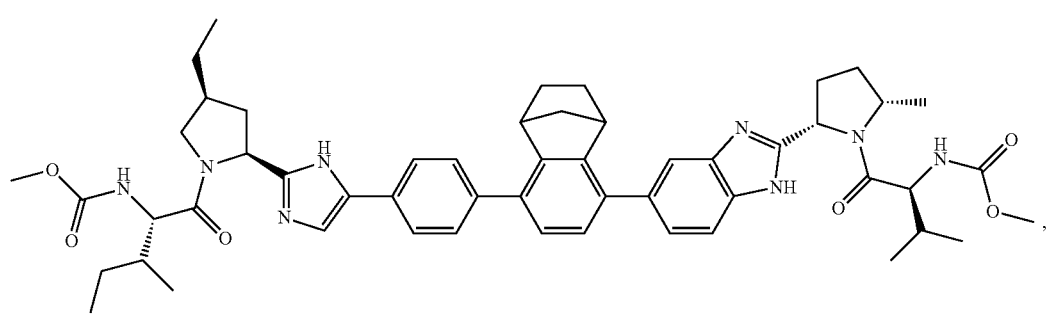

-continued
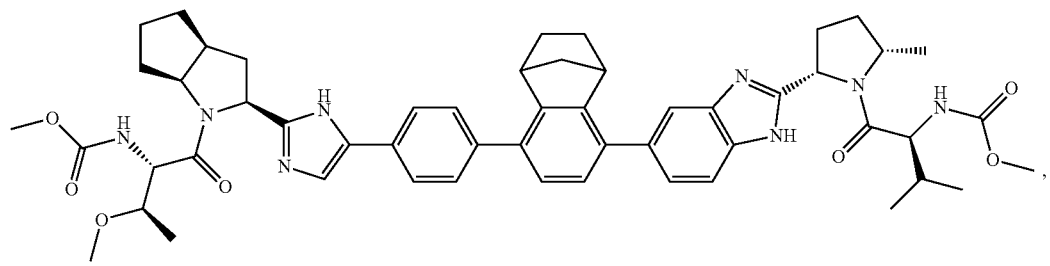
(11)
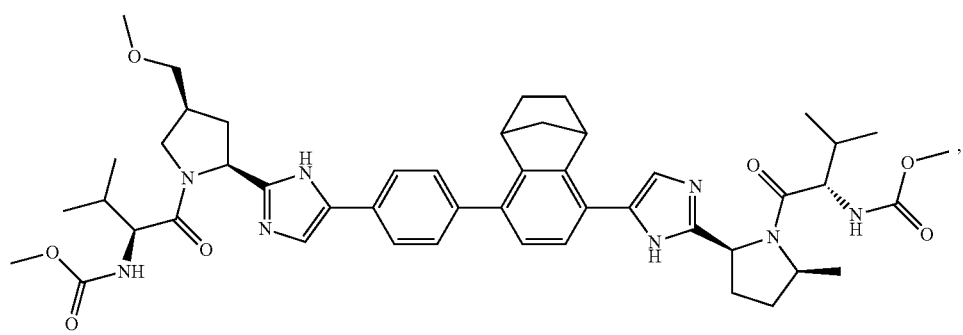
(12)
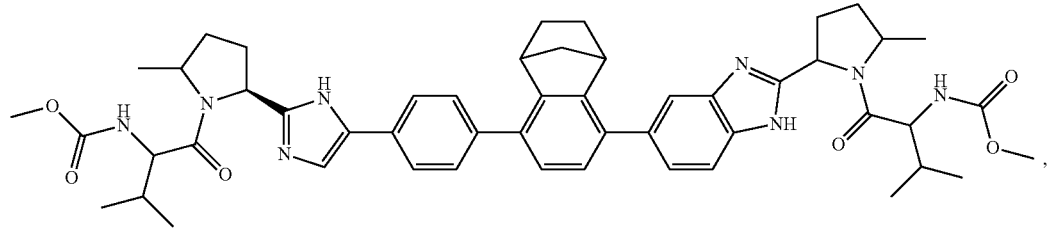
(13)
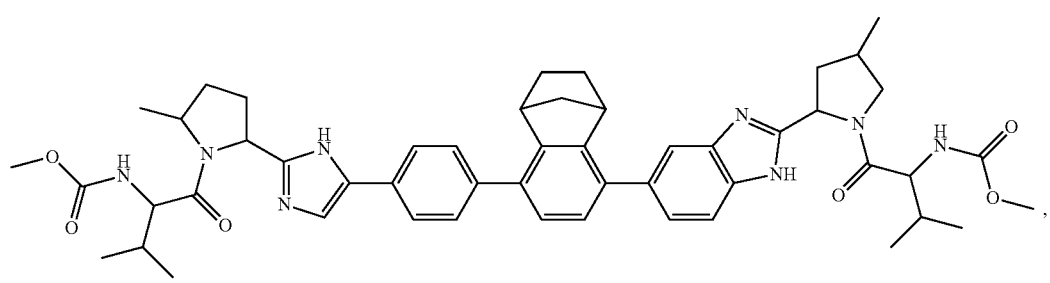
(14)
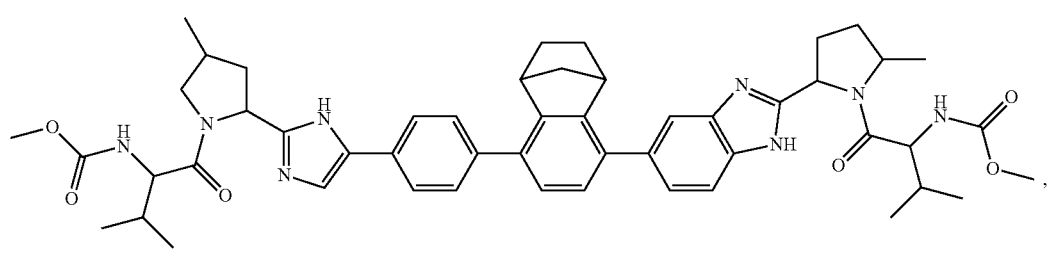
(15)
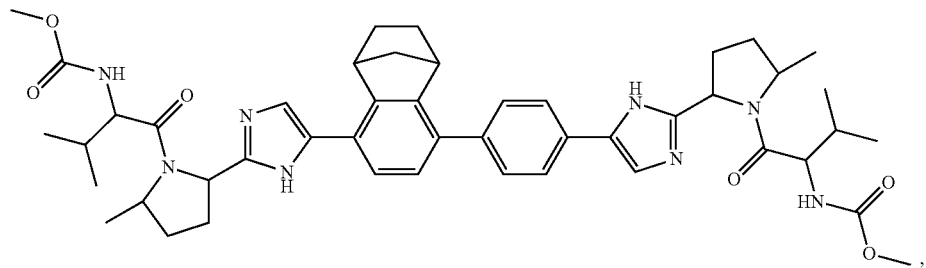
(16)

(17)

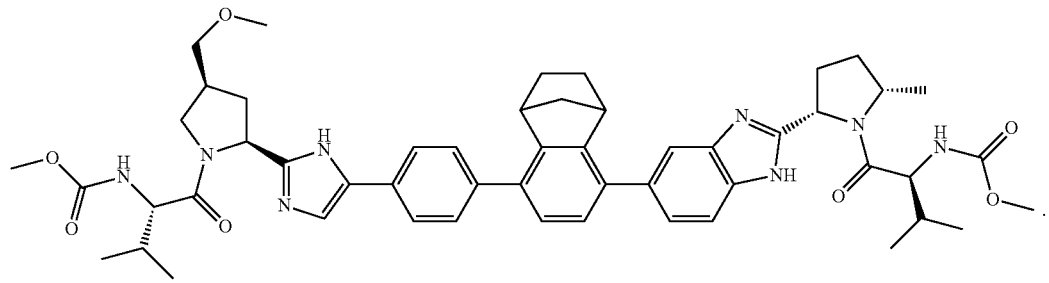

Provided herein includes the use of a compound disclosed herein (In present disclosure, "a compound disclosed herein" comprises a compound of formula (I), a stereoisomer, a geometric isomer, a tautomer, an N-oxide, a hydrate, a solvate and a pharmaceutically acceptable salt thereof), in the manufacture of a medicament for the treatment either acutely or chronically of HCV infection in a patient, including those described herein. Provided herein is use of the compound in the manufacture of an anti-HCV medicament. Provided herein is the use of the compound disclosed herein, in the manufacture of a medicament to attenuate, prevent, manage or treat disorders through inhibition of HCV, especially HCV's NS5A protein. The compounds disclosed herein are use for pharmaceutical composition active ingredients. Also provided herein is a pharmaceutical composition comprising a therapeutically effective amount of a compound of Formula (I) in association with at least one pharmaceutically acceptable carrier, adjuvant or diluent.

In certain embodiments, the salt is a pharmaceutically acceptable salt. The phrase "pharmaceutically acceptable" refers to that the substance or composition must be compatible chemically and/or toxicologically, with the other ingredients comprising a Formulation, and/or the mammal being treated therewith. The skills in the art could choose "pharmaceutically acceptable" substance or composition base on the other ingredients and the objects for treatment such as human.

The compounds disclosed herein also include salts of such compounds which are not necessarily pharmaceutically acceptable salts, and which may be useful as intermediates for preparing and/or purifying compounds of Formula (I) and/or for separating enantiomers of compounds of Formula (I).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, etc. Or with an organic acid, such as acetic acid, maleic acid, succinic acid, mandelic acid, fumaric acid, malonic acid, pyruvic acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid, a sulfonic acid, such as p-toluenesulfonic acid or ethanesulfonic acid, etc.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, etc. Some non-limiting examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, lithium, etc.

Composition, Formulations and Administration of Compounds of the Invention

The pharmaceutical composition disclosed herein comprises any one of the compounds. The pharmaceutical composition further comprises a pharmaceutically acceptable carrier, excipient, diluent, adjuvant, vehicle or a combination thereof. The pharmaceutical composition can be used for treating HCV infection or a HCV disorder, especially, it is great for inhibiting HCV NS5A protein.

The pharmaceutical composition disclosed herein further comprises anti-HCV agents. The anti-HCV agent may be any other known anti-HCV agent except the compound described herein, such as interferon, ribavirin, IL-2, IL-6, IL-12, a compound that enhances the development of a type 1 helper T cell response, an interfering RNA, an anti-sense RNA, imiquimod, an inosine-5'-monophosphate dehydrogenase inhibitor, amantadine, rimantadine, bavituximab, a HCV neutralizing polyclonal antibody (CIVACIR®), boceprevir, telaprevir, erlotinib, daclatasvir, simeprevir, asunaprevir, vaniprevir, faldaprevir, paritaprevir, danoprevir, sovaprevir, grazoprevir, vedroprevir, BZF-961, GS-9256, narlaprevir, ANA-975, ombitasvir, EDP-239, PPI-668, velpatasvir, samatasvir, elbasvir, MK-8325, GSK-2336805, PPI-461, BI-2013335, ciluprevir, ACH-1095, VX-985, IDX-375, VX-500, VX-813, PHX-1766, PHX-2054, IDX-136, IDX-316, modithromycin, VBY-376, TMC-649128, mericitabine, sofosbuvir, INX-189, IDX-184, IDX102, R-1479, UNX-08189, PSI-6130, PSI-938, PSI-879, nesbuvir, HCV-371, VCH-916, lomibuvir, MK-3281, dasabuvir, ABT-072, filibuvir, deleobuvir, tegobuvir, A-837093, JKT-109, G1-59728, GL-60667, AZD-2795, TMC647055, MK-3682, GS-9669, odalasvir, furaprevir, setrobuvir, alisporivir, BIT-225, AV-4025, ACH-3422, MK-2748, MK-8325, JNJ-47910382, ABP-560, TD-6450, TVB-2640, ID-12, PPI-383, A-848837, RG-7795, BC-2125 or a combination thereof. The interferon is interferon α-2b, pegylated interferon α, interferon α-2a, pegylated interferon α-2a, consensus interferon-α, interferon γ or a combination thereof. The pharmaceutical composition disclosed herein further comprises at least one HCV inhibitor. In some embodiments, the HCV inhibitor inhibits HCV replication process, a function of HCV viral protein or a combination thereof. The HCV replication process disclosed herein comprises of HCV entry, HCV uncoating, HCV translation, HCV replication, HCV assembly and HCV egress. The HCV viral protein disclosed herein is or comprises a metalloproteinase, non-structural protein NS2, NS3, NS4A, NS4B, NS5A or NS5B, or an internal ribosome entry site (IRES) or inosine-5'-monophosphate dehydrogenase (IMPDH) required in HCV viral replication.

When it is possible that, for use in therapy, therapeutically effective amounts of a compound of formula (I), as well as pharmaceutically acceptable salts thereof, may be administered as the raw chemical, it is possible to present the active ingredient as a pharmaceutical compositions, which include therapeutically effective amounts of compounds of formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit (e.g., a reduction in viral load). When applied to individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluents(s), or excipient(s) must be acceptable in the sense of being compatible with the other ingredients of the formulation and not deleterious to recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, composition, and/or dosage forms which are, within the scope of sound medical judgment, suitable for use in contact with the tissues of patients without excessive toxicity, irritation, allergic response, or other problem complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen. Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intraarticular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration of administration by injection is preferred.

Pharmaceutical formulations adapted for oral administration may be presented as discrete units such as capsules of tablets; powders or granules; solution or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, etc. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or β-lactose, natural paraguttas such as acacia, tragacanth or sodium alginate, carboxymethylcellulose, polyethylene glycol, etc. Lubricants used in these dosage forms include sodium oleate, sodium chloride, etc. Disintegrators include, without limitation, starch, methyl cellulose, agar, betonite, xanthan gum, etc. Tablets are formulated, for example, by preparing a powder mixture, granulating or slugging, adding a lubricant and disintegrant, and pressing into tablets. A powder mixture is prepared by mixing the compound, suitable comminuted, with a diluents or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solution of cellulosic or polymeric materials and forcing through a screen. As an alternative to granulation, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, etc can also be added.

Where appropriate, dosage unit formulations for oral administration can be microencapsulated. The formulation can also be prepared to prolong or sustain the release as for example by coating of embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carrier to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, poly(ϵ-caprolactone), polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmacol. Res.,* 1986, 3(6), 318.

Pharmaceutical formulations adapted for topical administration may be formulated as ointments, creams, suspensions, lotions, powders, solutions, pastes, gels, sprays, aerosols, oils or transdermal patch.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain antioxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to ingredients particularly mentioned above, the formulations may include other agents conventional in the art having regard to the type of formulation in question, for example those suitable for oral administration may include flavoring agents.

Uses of the Compounds and Compositions of the Invention

Provided herein is use of the compound or the pharmaceutical composition in the manufacture of a medicament for inhibiting HCV replication process, a function of a HCV viral protein function, or a combination thereof. In some embodiments, the HCV replication process comprises of HCV entry, HCV uncoating, HCV translation, HCV replication, HCV assembly and HCV egress. In some embodiments, the HCV viral protein is non-structural protein or an internal ribosome entry site (IRES) or inosine-5′-monophosphate dehydrogenase (IMPDH) required in HCV viral replication. And any one of the compounds or the pharmaceutical compositions disclosed herein can be used for treating HCV infection or a HCV disorder, especially it is effective as inhibitor of the non-structural 5A (NS5A) protein of HCV.

Also provided herein is a method, which comprises administering the compound or the pharmaceutical composition disclosed herein, further comprising administering to the patient additional anti-HCV agents (combination therapy), wherein the anti-HCV agent is an interferon, ribavirin, IL-2, IL-6, IL-12, a compound that enhances the development of a type 1 helper T cell response, an interfering RNA, an anti-sense RNA, imiquimod, an inosine-5′-monophosphate dehydrogenase inhibitor, amantadine, rimantadine, bavituximab, a HCV neutralizing polyclonal antibody (CIVACIR®), boceprevir, telaprevir, erlotinib, daclatasvir, simeprevir, asunaprevir, vaniprevir, faldaprevir, paritaprevir, danoprevir, sovaprevir, grazoprevir, vedroprevir, BZF-961, GS-9256, narlaprevir, ANA-975, ombitasvir, EDP-239, PPI-668, velpatasvir, samatasvir, elbasvir, MK-8325, GSK-2336805, PPI-461, BI-2013335, ciluprevir, ACH-1095, VX-985, IDX-375, VX-500, VX-813, PHX-1766, PHX-2054, IDX-136, IDX-316, modithromycin, VBY-376, TMC-649128, mericitabine, sofosbuvir, INX-189, IDX-184, IDX102, R-1479, UNX-08189, PSI-6130, PSI-938, PSI-879, nesbuvir, HCV-371, VCH-916, lomibuvir, MK-3281, dasabuvir, ABT-072, filibuvir, deleobuvir, tegobuvir, A-837093, JKT-109, G1-59728, GL-60667, AZD-2795, TMC647055, MK-3682, GS-9669, odalasvir, furaprevir, setrobuvir, alisporivir, BIT-225, AV-4025, ACH-3422, MK-2748, MK-8325, JNJ-47910382, ABP-560, TD-6450, TVB-2640, ID-12, PPI-383, A-848837, RG-7795, BC-2125 or a combination thereof. Wherein the interferon is interferon α-2b, pegylated interferon α, interferon α-2a, pegylated interferon α-2a, consensus interferon-α, interferon γ or a combination thereof.

The treatment method that includes administering a compound or composition disclosed herein can further include administering to the patient an additional anti-HCV agent, wherein the additional anti-HCV drug is administered together with a compound or composition disclosed herein as a single dosage form or separately from the compound or composition as part of a multiple dosage form. The additional anti-HCV agent may be administered at the same time as a compound disclosed herein or at a different time. In the latter case, administration may be staggered by, for example, 6 hours, 12 hours, 1 day, 2 days, 3 days, 1 week, 2 weeks, 3 weeks, 1 month, or 2 months.

In certain embodiments disclosed herein, an "effective amount" or "effective dose" of the compound or pharmaceutically acceptable composition is that amount effective for treating or lessening the severity of one or more of the aforementioned disorders. The compounds and compositions, according to the method disclosed herein, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, etc. A compound or composition can also be administered with one or more other therapeutic agents, as discussed above.

General Synthetic Procedures

Generally, the compounds disclosed herein may be prepared by methods described herein, wherein the substituents are as defined for Formula (I), above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous tetrahydrofuran, dioxane, toluene, and ether were obtained by refluxing the solvent with sodium. Anhydrous dichloromethane and chloroform were obtained by refluxing the solvent with calcium hydride. ethyl acetate, petroleum ether, hexane, N,N-dimethylacetamide and N,N-dimethylformamide were treated with anhydrous sodium sulfate prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were recorded with a Bruker 400 MHz spectrometer at ambient temperature. $^1$H NMR spectra were obtained as $CDCl_3$, $d_6$-DMSO, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were also determined on an Agilent 6320 series LC-MS spectrometer equipped with G1312A binary pumps, a G1316A TCC (Temperature Control of Column, maintained at 30° C.), a G1329A autosampler and a G1315B DAD detector were used in the analysis. An ESI source was used on the LC-MS spectrometer.

Low-resolution mass spectral (MS) data were also determined on an Agilent 6120 series LC-MS spectrometer equipped with G1311A Quaternary pump, a G1316A TCC (Temperature Control of Column, maintained at 30° C.), a G1329A autosampler and a G1315D DAD detector were used in the analysis. An ESI source was used on the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient condition is shown in Table 1:

TABLE 1

| Time (min) | A ($CH_3CN$, 0.1% HCOOH) | B ($H_2O$, 0.1% HCOOH) |
| --- | --- | --- |
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micorn, 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:
HOAc acetic acid
MeCN, $CH_3CN$ acetonitrile
$NH_3$ ammonia
$NH_4Cl$ ammonium chloride
$BBr_3$ boron tribromide
BSA bovine serum albumin
$Br_2$ bromine
BOC, Boc tert-butyloxycarbonyl
$Cs_2CO_3$ cesium carbonate
$CHCl_3$ chloroform CDCl$_3$ chloroform deuterated
Cu copper
CuI copper (I) iodide
Et$_2$O diethyl ether
DMF dimethylformamide
DMAP 4-dimethylaminopyridine
DMSO dimethylsulfoxide
EDC, EDCI 1-(3-dimethylaminopropyl)-3-ethylcarbodiimide hydrochloride
Dppa diphenylphosphoryl azide
EtOAc ethyl acetate
EA ethyl acetate
g gram
HBr hydrobromic acid
HCl hydrochloric acid
HI hydroiodic acid
HOAt, HOAT 1-hydroxy-7-azabenzotriazole
HOBT 1-hydroxybenzotriazole
H$_2$ hydrogen
H$_2$O$_2$ hydrogen peroxide
Fe iron
LDA lithium diisopropylamide
MCPBA meta-chloroperbenzoic acid
MgSO$_4$ magnesium sulfate
MeOH, CH$_3$OH methanol
MeI methyl iodide
CH$_2$Cl$_2$, DCM methylene chloride
NMP N-methylpyrrolidinone
mL, ml milliliter
N$_2$ nitrogen
Pd/C palladium on activated carbon
PE petroleum ether (60-90° C.)
PBS phosphate buffered saline
POCl$_3$ phosphorous oxychloride
Pd(PPh$_3$)$_4$ palladium tetrakis triphenylphosphine
Pd(dppf)Cl$_2$ 1,1'-bis(diphenylphosphino)ferrocene dichloropalladium(II)
K$_2$CO$_3$ potassium carbonate
KOH potassium hydroxide
RT, rt room temperature
Rt retention time
NaHCO$_3$ sodium bicarbonate
NaBH$_4$ sodium borohydride
NaBH$_3$CN sodium cyanoborohydride
NaOtBu sodium tert-butoxide
NaOH sodium hydroxide
NaClO$_2$ sodium chlorite
NaCl sodium chloride
NaH$_2$PO$_4$ sodium dihydric phosphate
NaH sodium hydride
NaI sodium iodide
Na$_2$SO$_4$ sodium sulfate
TBTU O-benzotriazol-1-yl-N,N,N',N'-tetramethyluronium tetrafluoroborate
THF tetrahydrofuran
Et$_3$N, TEA triethylamine
TFA trifluoroacetic acid
P(t-bu)$_3$ tri(tert-butyl)phosphine
NBS N-bromosuccinimide
TBAI tetrabutylammonium iodide
H$_2$O water
TEAF triethylamine formic acid
PPA polyphosphoric acid
TEA triethylamine
Tf$_2$O trifluoromethanesulfonic anhydride
TfOH trifluoromethanesulfonic acid
HCl.EA a solution of HCl in ethyl acetate
DIPEA N,N-diisopropylethylamine
DME 1,2-dimethoxyethane
HATU 2-(7-aza-1H-benzotriazole-1-yl)-1,1,3,3-tetramethyluronium hexafluorophosphate
NIS N-iodosuccinimide
TFAA trifluoroaceticanhydride
SEMCl 2-(Trimethylsilyl)ethoxymethyl chloride
Dess-Martin(Dess-Martin periodinane) (1,1,1-Triacetoxy)-1,1-dihydro-1,2-benziodoxol-3(1H)-one
TsOH p-toluenesulfonic acid
TMSA trimethyl silyl acetylene
Meldrum's acid 2,2-dimethyl-1,3-dioxane-4,6-dione
BAST bis(2-methoxyethyl)aminosulphurtrifluoride Deoxofluor
SbCl$_3$ antimony trichloride
SmCl$_3$ samarium chloride
LiHMDS lithium hexamethyldisilazide
TMSCl trimethyl chlorosilane
PhNTf$_2$ N,N-bis(trifluoromethylsulfonyl)aniline
TBDMSOTf trifluoromethanesulfonic acid tert-butyldimethylsilyl ester
Et$_2$NSF$_3$ diethylaminosulfur trifluoride
MTBE methyl tert-butyl ether
LiN(SiMe$_3$)$_2$ lithium bis(trimethylsilyl)amide
PPh$_3$MeBr methyltriphenylphosphonium bromide
Lawesson's Reagent 2,4-bis(4-methoxyphenyl)-1,3-dithia-2,4-diphosphetane 2,4-disulfide
TEBAC benzyltriethylammonium chloride
I$_2$ iodine
DAST diethylaminosulfur trifluoride
IPA isopropanol
TCCA trichloroisocyanuric acid
TEMPO 2,2,6,6-tetramethylpiperidinooxy
IMPDH inosine monophosphate dehydrogenase
IRES internal ribosome entry site Scheme

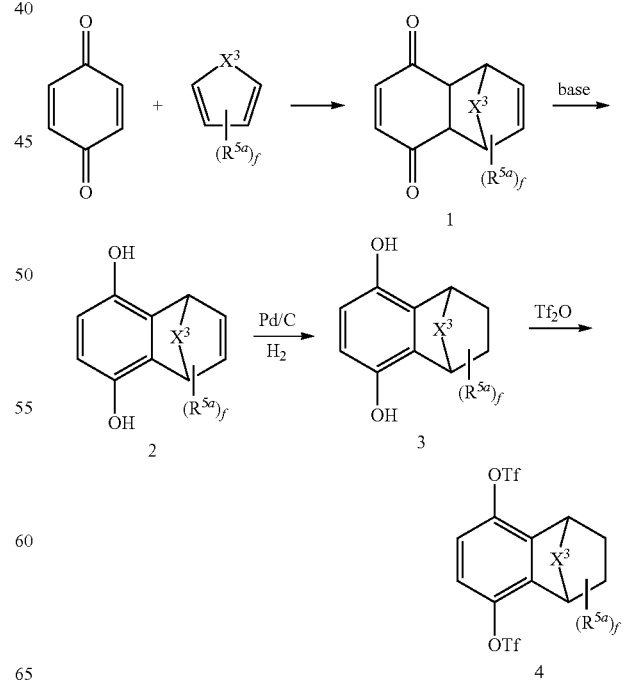

Scheme 1

Compound 4 can be prepared by a general synthetic procedure illustrated in Scheme 1, wherein each $R^{5a}$, $X^3$ and f is as defined herein. Benzoquinone can react with conjugated dienes to afford compound 1 via Diels-Alder reaction. By the reaction of rearrangement, compound 1 can be converted to compound 2 in the presence of base. Compound 2 can be reduced to afford compound 3 in the presence of Pd/C under $H_2$, and compound 3 can be converted to target compound 4 in the presence of base and trifluoromethanesulfonic anhydride.

Scheme 2

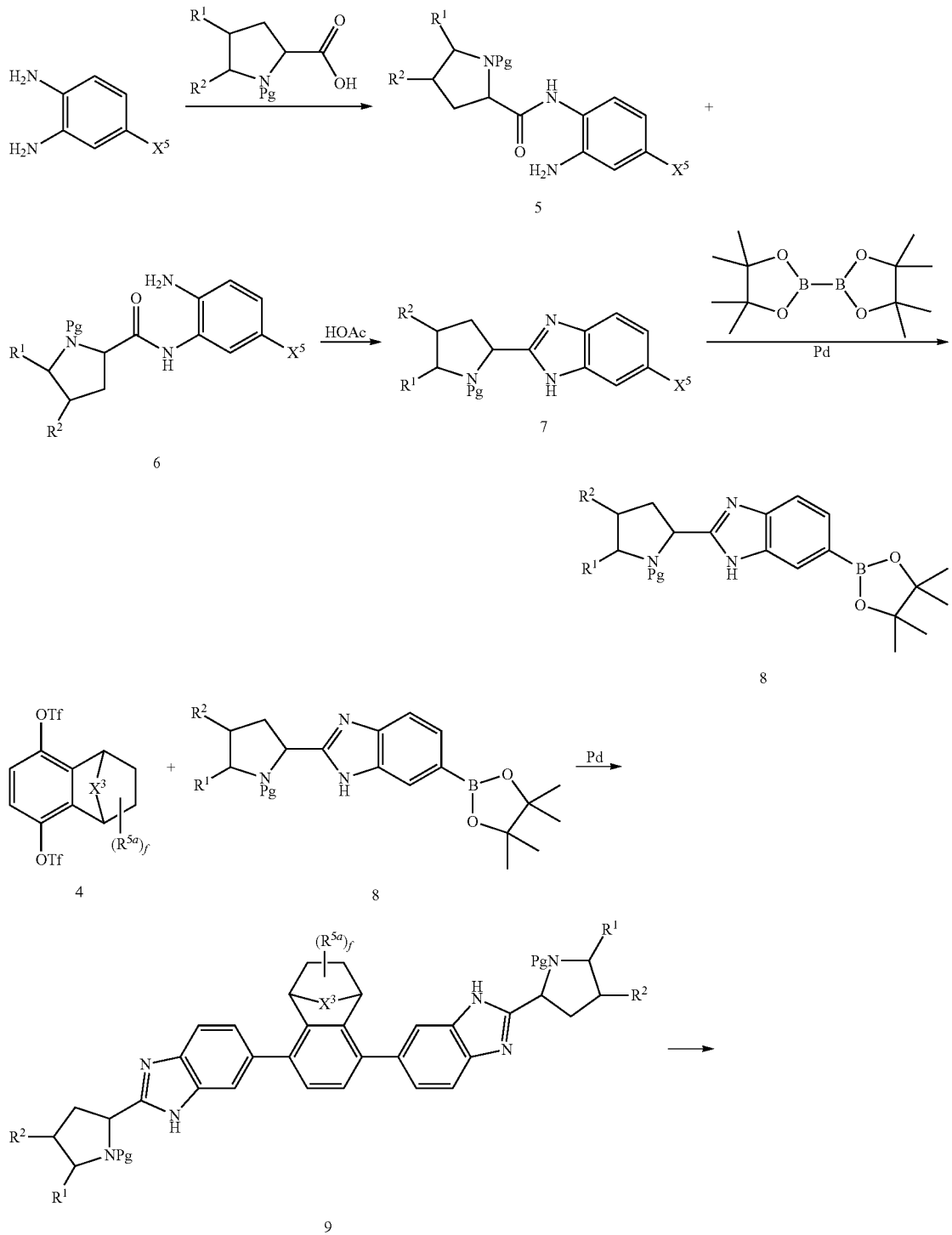

-continued

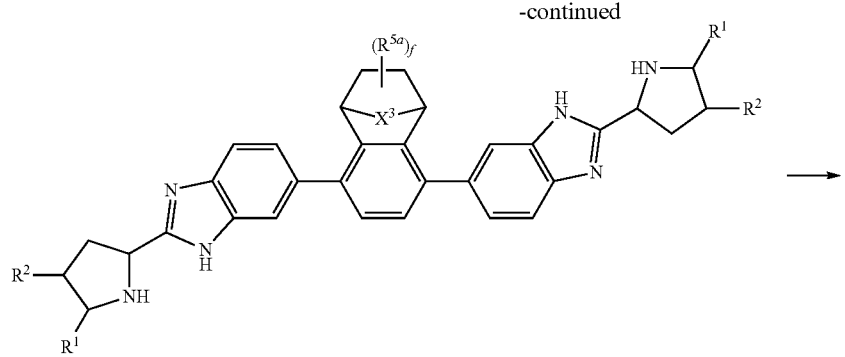

10

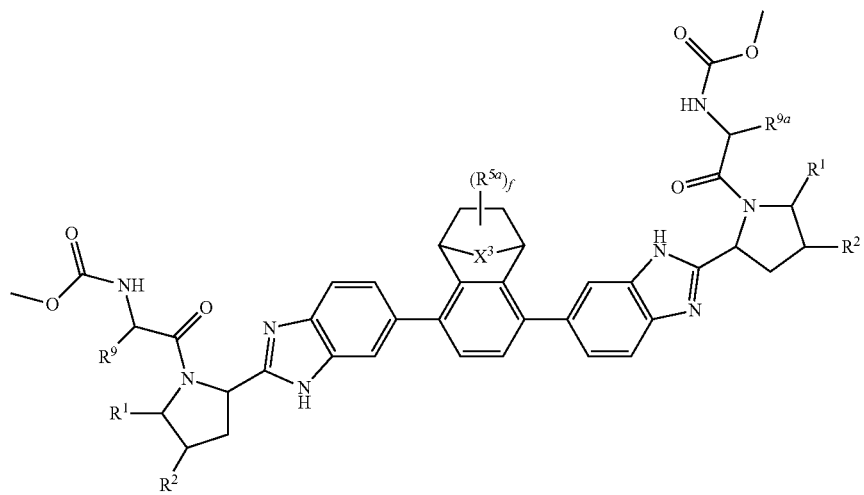

11

The target compound 11 can be prepared by a general synthetic procedure illustrated in Scheme 2, wherein each $X^5$ is leaving group of F, Cl, Br, I, and so on; each $R^{5a}$, $X^3$, $R^1$, $R^2$, $R^9$ and $R^{9a}$ is as defined herein; and Pg is an amino-protecting group such as Boc, Fmoc or Cbz, and so on. O-phenylenediamine can be condensed with protected proline to obtain the mixture of compound 5 and compound 6. By the reaction of cyclization, compound 5 and compound 6 can be converted to compound 7 in the presence of acetic acid under heating. By a catalyst Pd, and compound 7 can react with 4,4,4',4',5,5,5',5'-octamethyl-2,2'-bi(1,3,2-dioxaborolane) to give compound 8 in the presence of a catalyst Pd. Coupling reaction of compound 8 with compound 4 affords compound 9 in the presence of a catalyst Pd, then deprotection of compound 9 affords compound 10 which can afford compound 11 by the condensation reaction.

Scheme 3

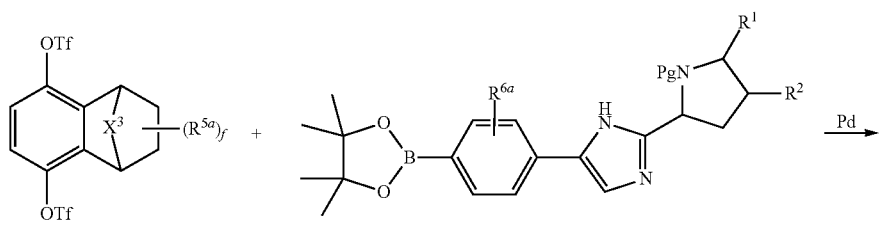

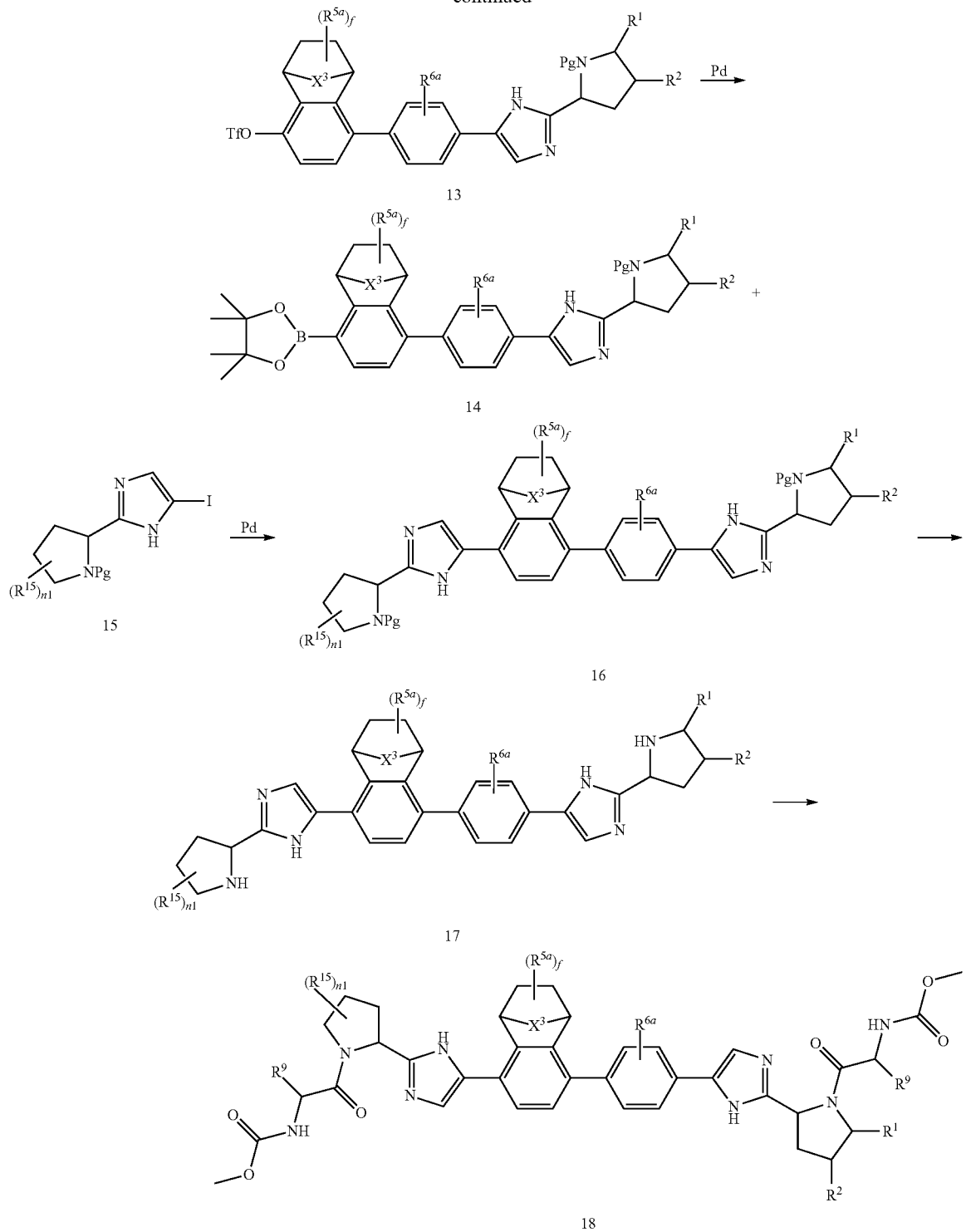

Compound 18 can be prepared by a general synthetic procedure illustrated in Scheme 3, wherein each $R^{5a}$, $R^{6a}$, $X^3$, $R^1$, $R^2$, $R^9$, $R^{15}$, $n_1$, f and $R^{9a}$ is as defined herein. Pg is an amino-protecting group such as Boc, Fmoc or Cbz, and so on. Coupling reaction of compound 4 with compound 12 affords a mixture of compound 13 in the presence of a catalyst Pd, and compound 13 can react with 4,4,4',4',5,5, 5',5'-octamethyl-2,2'-bi(1,3,2-dioxaborolane) to give compound 14 in the presence of a catalyst Pd. Coupling reaction of compound 14 with compound 15 affords a mixture of compound 16 in the presence of a catalyst Pd. The protecting group Pg of compound 16 can be removed to afford compound 17, and compound 17 can afford the target compound 18 by the condensation reaction.

Scheme 4

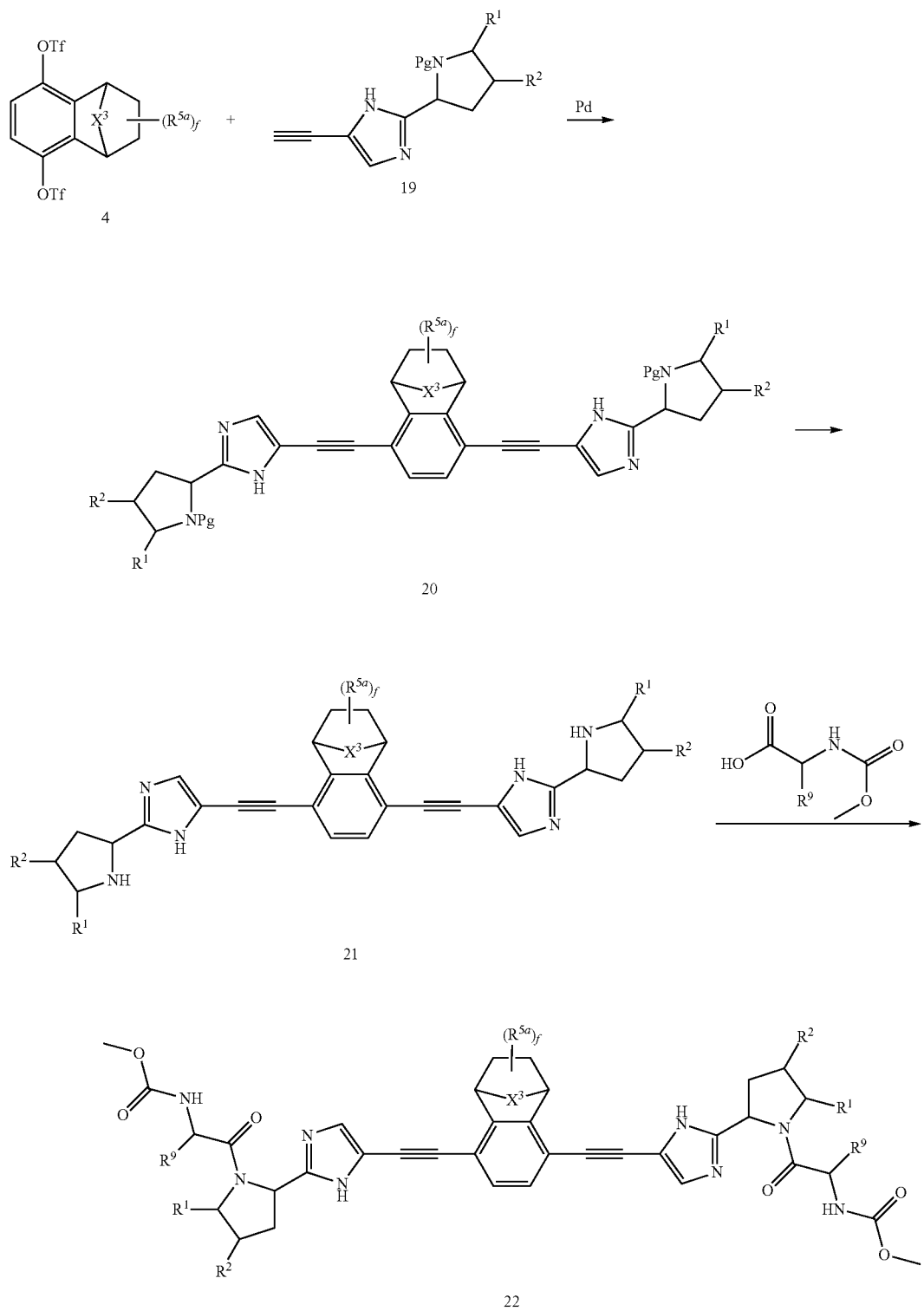

Compound 22 can be prepared by a general synthetic procedure illustrated in Scheme 4, wherein each $R^{5a}$, $X^3$, $R^1$, $R^2$, $R^9$ and f is as defined herein. Pg is an amino-protecting group such as Boc, Fmoc or Cbz, and so on. Coupling reaction of compound 4 with compound 19 affords a mixture of compound 20 in the presence of a catalyst Pd. The protecting group Pg of compound 20 can be removed to afford compound 21, and compound 21 can afford the target compound 22 by the condensation reaction.

Scheme 5

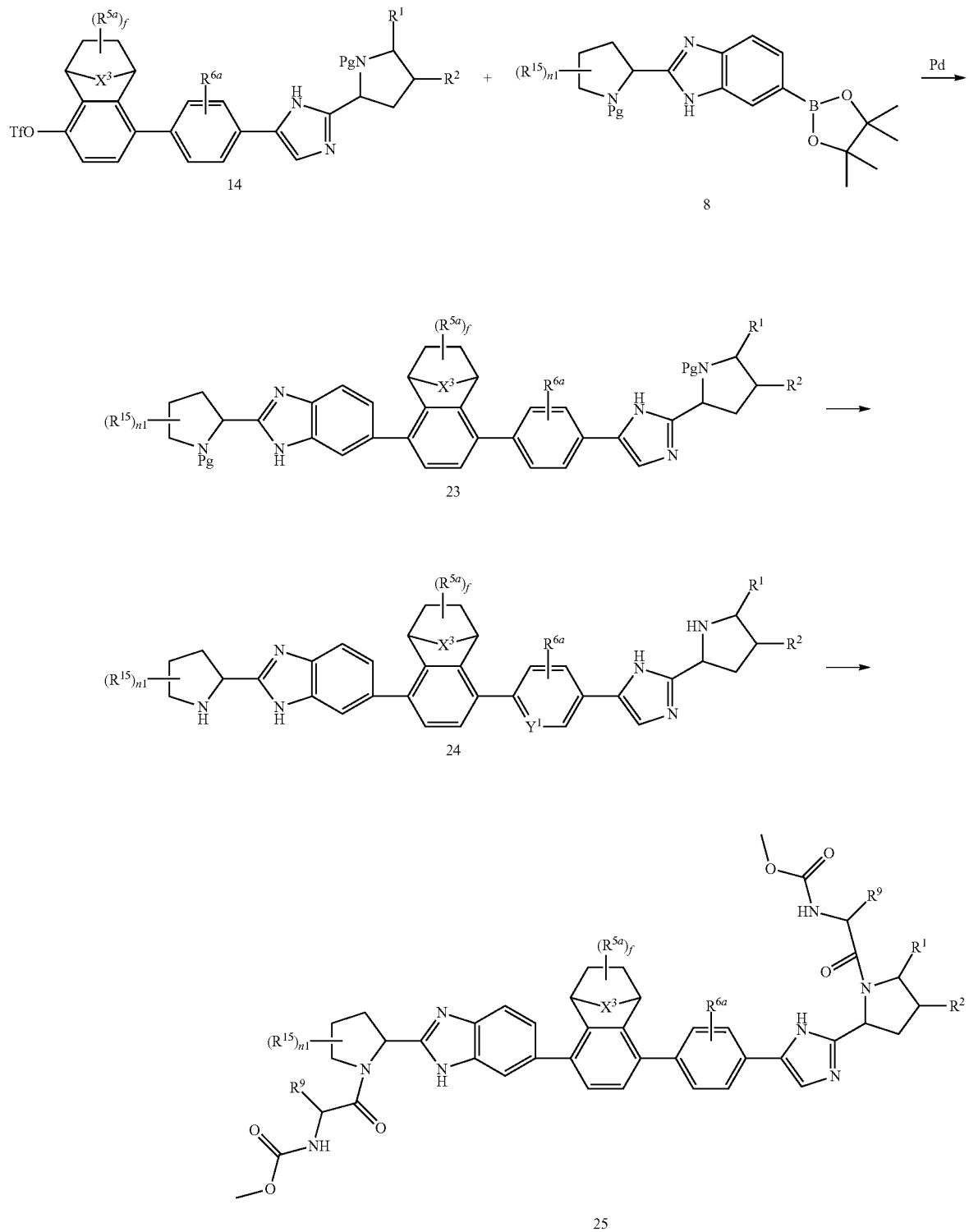

Compound 25 can be prepared by a general synthetic procedure illustrated in Scheme 5, wherein each $R^{5a}$, $R^{6a}$, $X^3$, $R^1$, $R^2$, $R^{15}$, $n_1$, $R^9$ and f is as defined herein. Pg is an amino-protecting group such as Boc, Fmoc or Cbz, and so on. Coupling reaction of compound 14 with compound 8 affords compound 23 in the presence of a catalyst Pd. The protecting group Pg of compound 23 can be removed to afford compound 24, and compound 24 can afford the target compound 25 by the condensation reaction.

EXAMPLE
Example 1
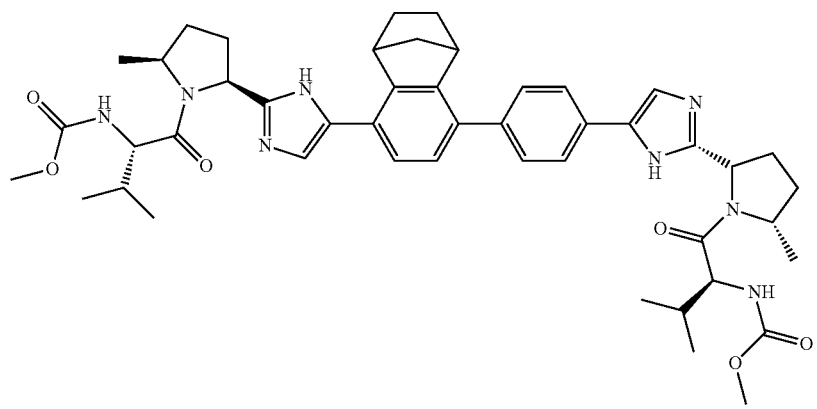
Synthetic Route:
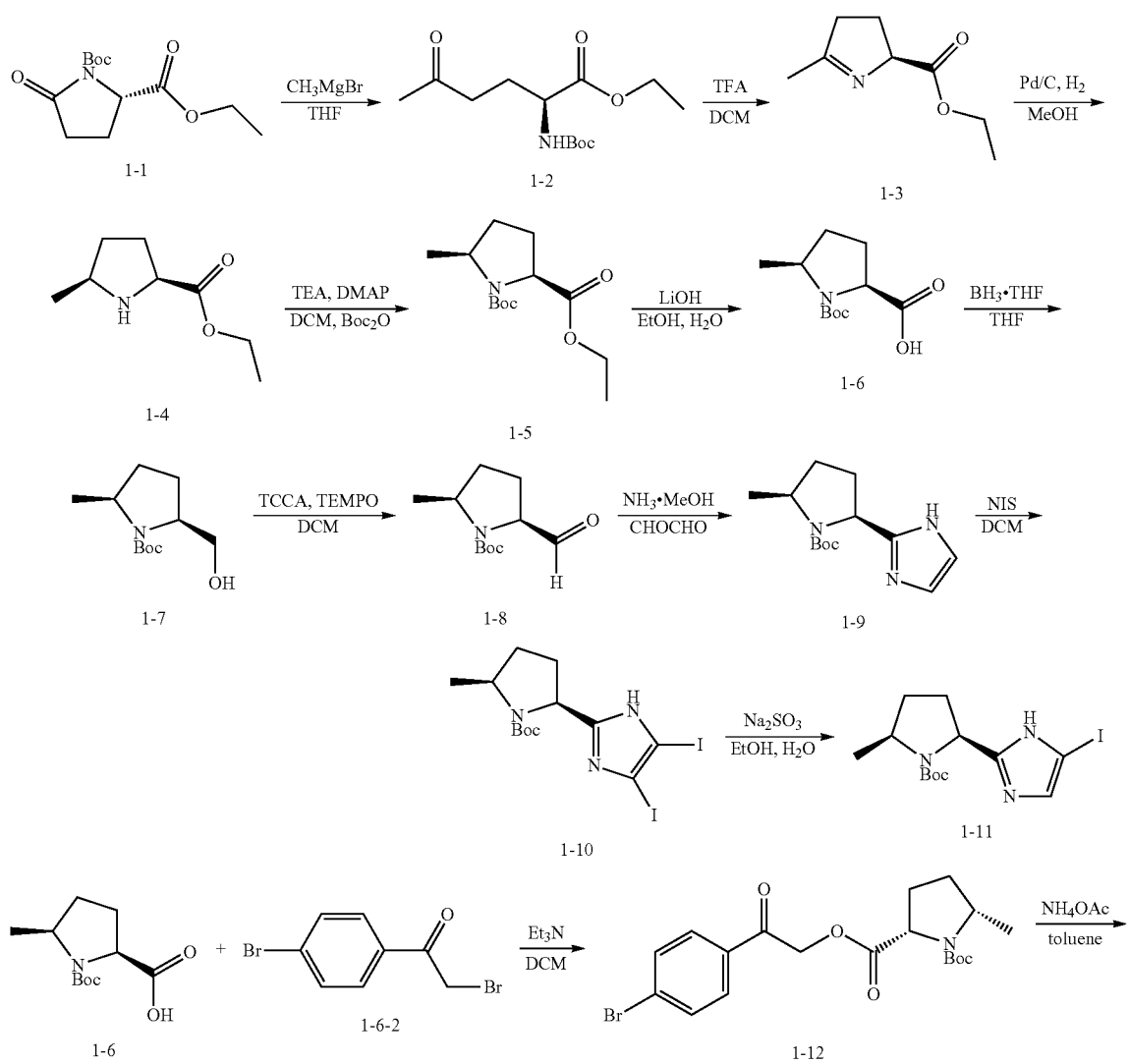

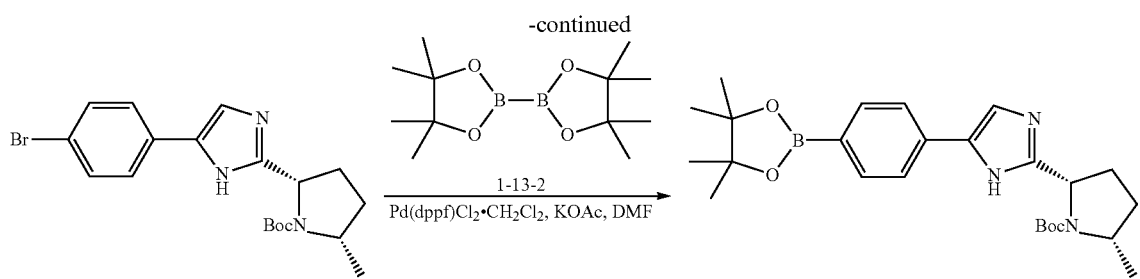
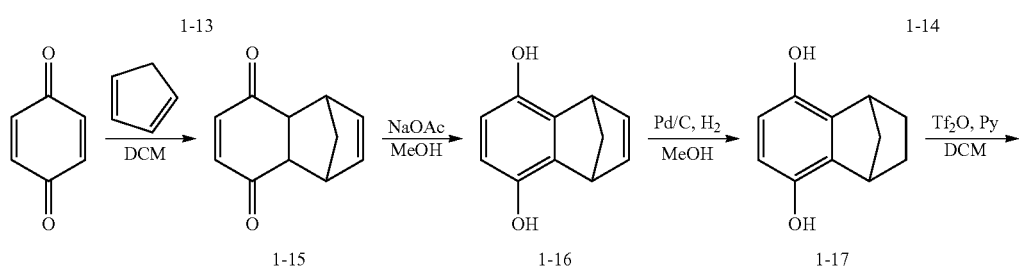
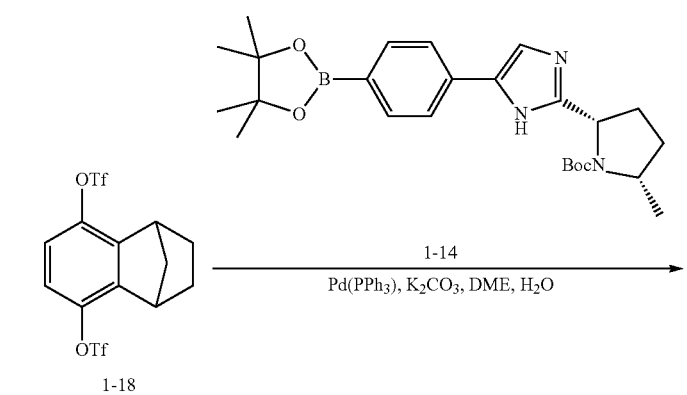
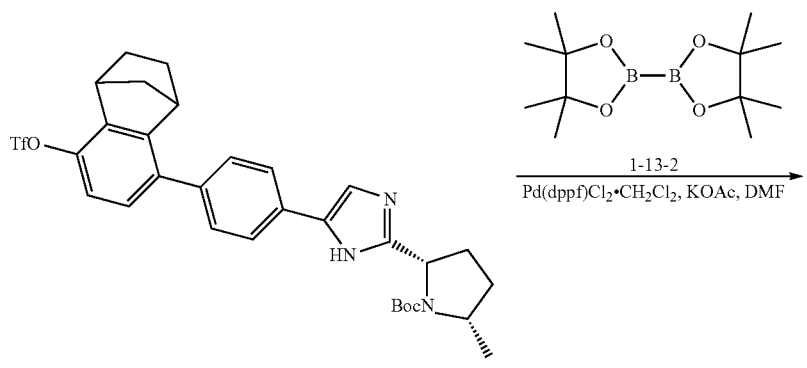
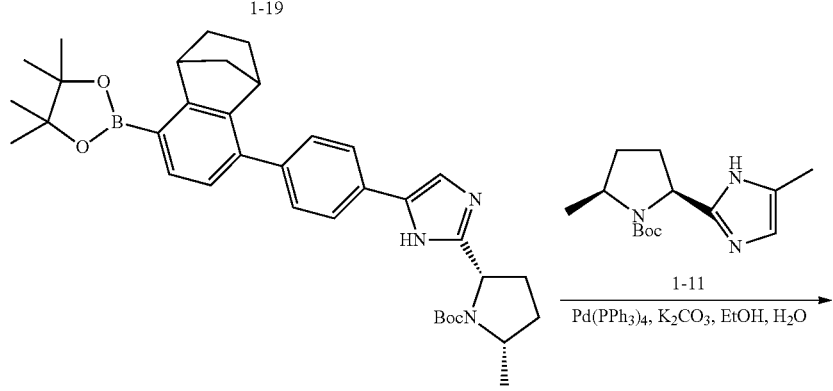

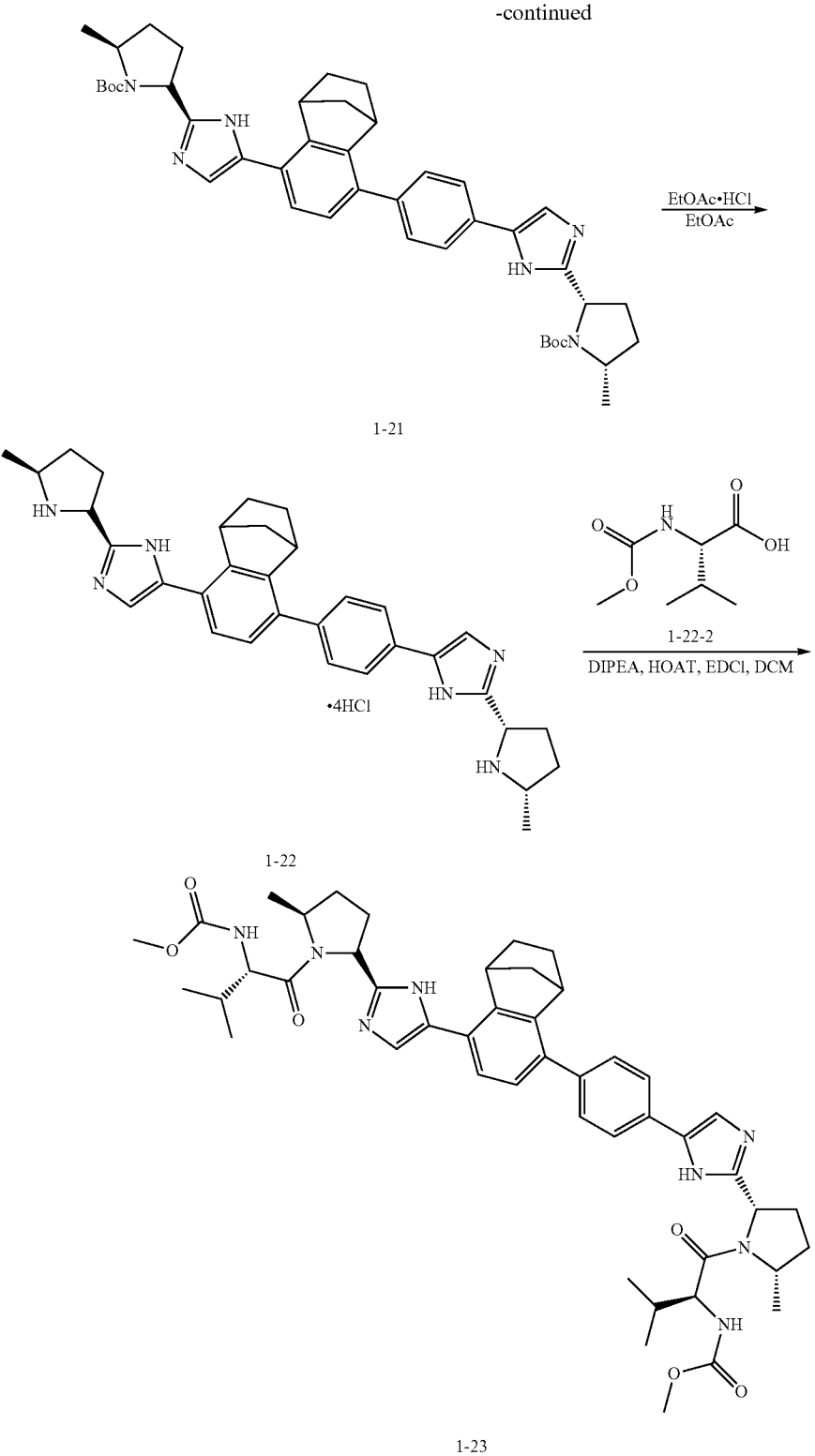

Step 1) the Preparation of Compound 1-2

To a cooled −40° C. solution of compound 1-1 (25 g, 97.16 mmol) in THF (100 mL) was added a solution of MeMgBr in ether (41.4 mL, 3 mol/L). The mixture was stirred at −40° C. for 2 hours, and then stirred at −20° C. overnight. After the reaction was completed, the reaction was quenched with aqueous ammonium chloride solution (50 mL). The THF solvent was removed and the residue was dissolved in EtOAc (200 mL). The resulting mixture was washed with water (100 mL×3), and the organic phase was dried over anhydrous $Na_2SO_4$ and concentrated in vacuo. The residue was purified by silica gel column chromatography (PE/EtOAc (v/v)=8/1) to give the title compound as colorless liquid (13.0 g, 49%). The compound was characterized by the following spectroscopicdata:

MS (ESI, pos.ion) m/z: 274.3 [M+H]$^+$; and
$^1$H NMR (400 MHz, CDCl$_3$): δ 7.95 (br.s, 1H), 4.55 (m, 1H), 4.19 (m, 2H), 2.51 (m, 2H), 2.19 (m, 2H), 2.13 (s, 3H), 1.42 (s, 9H), 1.28 (t, J=6.2 Hz, 3H) ppm.

Step 2) the Preparation of Compound 1-3

To a solution of compound 1-2 (13 g, 47.57 mmol) in DCM (20 mL) was added trifluoroacetic acid (20 mL) at 25° C. The mixture was stirred at 25° C. and monitored by TLC. After the reaction was completed, the trifluoroacetic acid was removed in vacuo to give the title compound 1-3 as colourless oil which was used directly for next step. The compound was characterized by the following spectroscopic data:

MS (ESI, pos.ion) m/z: 156.3 [M+H]$^+$; and
$^1$H NMR (400 MHz, CDCl$_3$): δ 4.94-4.91 (br, 1H), 4.23-4.18 (m, 2H), 2.67-2.53 (br, 2H), 2.23-2.07 (m, 2H), 2.02 (s, 3H), 1.27-1.24 (m, 3H) ppm.

Step 3) the Preparation of Compound 1-4

To a solution of crude compound 1-3 prepared in step 2) in EtOH (150 mL) was added Pd/C (4.0 g). The mixture was stirred at 50° C. under H$_2$ for 12 hours. After the reaction was completed, the mixture was filtered through diatomite. The EtOH was removed in vacuo to give the compound 1-4 as a white solid which was used directly for next step. The compound was characterized by the following spectroscopic data:

MS (ESI, pos.ion) m/z: 158.3 [M+H]$^+$; and
$^1$H NMR (400 MHz, CDCl$_3$): δ 4.20-4.14 (m, 2H), 3.79-3.74 (br, 1H), 3.28-3.21 (m, 1H), 2.15-2.07 (m, 1H), 2.01-1.92 (m, 1H), 1.84-1.74 (m, 1H), 1.53-1.43 (m, 1H), 1.29-1.22 (m, 6H) ppm.

Step 4) the Preparation of Compound 1-5

To a cooled 0° C. solution of compound 1-4 (7.48 g, 47.57 mmol), TEA (16 mL, 115.4 mmol) and DMAP (352 mg, 28.86 mmol) in DCM (140 mL) was added Boc$_2$O (14.6 mL, 63.49 mmol). After the addition, the mixture was stirred at 25° C. and monitored by TLC. After the reaction was completed, the mixture was diluted with DCM (200 mL). The resulting mixture was washed with aqueous ammonium chloride solution (100 mL×2). The separated organic phase was dried over anhydrous Na$_2$SO$_4$ and concentrated in vacuo. The residue was purified by silica gel column chromatography (PE/EtOAc (v/v)=10/1) to give the title compound as colorless liquid (9.11 g, 74%). The compound was characterized by the following spectroscopic data:

MS (ESI, pos.ion) m/z: 258.3 [M+H]$^+$; and
$^1$H NMR (400 MHz, CDCl$_3$): δ 4.31-4.27 (br, 1H), 4.14-4.09 (m, 3H), 2.18-2.12 (m, 1H), 1.99-1.91 (m, 2H), 1.73-1.65 (m, 1H), 1.44 (s, 9H), 1.36-1.33 (m, 3H), 1.29-1.26 (m, 3H) ppm.

Step 5) the Preparation of Compound 1-6

To a solution of compound 1-5 (9.11 g, 35.45 mmol) in EtOH (80 mL) was added a solution of Lithium hydroxide hydrate (2.5 g, 59.67 mmol) in 20 mL of H$_2$O at 25° C. The mixture was stirred at 25° C. for 12 hours. After the reaction was completed, the mixture was extracted with EtOAc (150 mL), then the EtOAc phase was discarded. The aqueous phase was adjusted to pH 2 with 6% hydrochloric acid, then the resulting mixture was extracted with EtOAc (80 mL×3). The combined organic phases were dried over anhydrous Na$_2$SO$_4$ and concentrated in vacuo to give the title compound as a white solid (8.0 g, 98.5%).

The compound was characterized by the following spectroscopic data:

MS (ESI, pos.ion) m/z: 230.3 [M+H]$^+$; and
$^1$H NMR (400 MHz, CD$_3$OD): δ 4.24 (m, 1H), 3.56 (m, 1H), 1.75-1.97 (m, 2H), 1.45-1.69 (m, 2H), 1.40 (s, 9H), 1.32-1.34 (m, 3H) ppm.

Step 6) the Preparation of Compound 1-7

To a cooled 0° C. solution of compound 1-6 (2.24 g, 9.78 mmol) in THF (20 mL) was added a solution of borane in THF (14.6 mL, 1 mol/L). The mixture was stirred at 25° C. for 2 hours, and then to the mixture was added MeOH (8.0 mL). The THF was removed in vacuo and the residue was dissolved in DCM (30 mL). The resulting mixture was washed with water (20 mL×3). The separated organic phase was dried over anhydrous Na$_2$SO$_4$ and concentrated in vacuo. The residue was purified by silica gel column chromatography (PE/EtOAc (v/v)=3/1) to give the title compound as colorless oil (1.98 g, 94.3%). The compound was characterized by the following spectroscopic data:

MS (ESI, pos.ion) m/z: 216.2 [M+H]$^+$; and
$^1$H NMR (400 MHz, CDCl$_3$): δ 3.90-3.91 (br, 2H), 3.62-3.65 (m, 2H), 3.50-3.54 (m, 1H), 1.91-1.93 (m, 2H), 1.51-1.60 (m, 2H), 1.44 (s, 9H), 1.13-1.14 (d, J=6.2 Hz, 3H) ppm.

Step 7) the Preparation of Compound 1-9

To a cooled 0° C. solution of compound 1-7 (1.98 g, 9.2 mmol) in DCM (20 mL) was added a solution of TCCA (2.14 g, 9.2 mmol) and TEMPO (156 mg, 1.0 mmol in DCM (5 mL). The mixture was stirred at 0° C. for 1 hour and then stirred at 25° C. for further 1 hour. After the reaction was completed, the mixture was filtered to remove the solid. The filtrate was washed with saturate aqeuous sodium sulfite solution (50 mL×3). The organic phase was dried over anhydrous Na$_2$SO$_4$ and concentrated in vacuo to give a compound 1-8 as coloress oil which was used directly for the next step. The compound 1-8 was dissolved in a solution of NH$_3$ in MeOH (20 mL, 7 mol/L). The reaction mixture was stirred at 0° C. for 0.5 hour, and then moved to 25° C. for 1 hour. The mixture was cooled at 0° C. diluted with a solution of glyoxal in MeOH (2.5 mL, 40%) and H$_2$O (4 mL). At the end of the addition, the mixture was stirred at 25° C. for 24 hours. After the reaction was completed, the mixture was concentrated in vacuo. The residue was dissolved in DCM (30 mL), and the resulting mixture was washed with water (20 mL×3). The separated aqueous phases were extracted with DCM (50 mL×3). The combined phases were dried over anhydrous Na$_2$SO$_4$ and concentrated in vacuo. The residue was purified by silica gel column chromatography (DCM/MeOH (v/v)=50/1) to give the title compound as a light yellow solid (1.18 g, yield of two steps: 51%). The compound was characterized by the following spectroscopicdata:

MS (ESI, pos.ion) m/z: 252.3 [M+H]$^+$; and
$^1$H NMR (400 MHz, CDCl$_3$): δ 6.97 (s, 2H), 4.90 (t, J=8.0 Hz, 1H), 3.76 (dd, J=10.0 Hz, 7.2 Hz, 1H), 2.83 (t, J=8.0 Hz, 1H), 2.64-2.33 (m, 2H), 2.32-2.12 (m, 1H), 1.47 (s, 9H), 1.13-1.14 (d, J=6.4 Hz, 3H) ppm.

Step 8) the Preparation of Compound 1-11

To a cooled 0° C. solution of compound 1-9 (1.18 g, 4.7 mmol) in DCM (20 mL) was added NIS (2.34 g, 10.4 mmol). The mixture was stirred at 0° C. for 2 hours, and then filtered. The filtrate was washed with saturate aqueous sodium sulfite solution (50 mL×3). The organic phase was dried over anhydrous Na$_2$SO$_4$ and concentrated in vacuo to give compound 1-10 as a yellow solid (1.85 g, 78%) which was used directly for the next step. To a solution of compound 1-10 (1.85 g, 3.67 mmol) in EtOH (15 mL) was added sodium sulfite (4.16 g, 33 mmol) and H₂O (15 mL). The reaction was stirred at 90° C. for 30 hours. After the reaction was completed, the mixture was filtered, and the filtrate was concentrated in vacuo. The residue was dissolved in DCM (20 mL), and the resulting mixture washed with water (30 mL). The separated aqueous phase was extracted with DCM (40 mL×3). The combined organic phases were dried over anhydrous Na₂SO₄ and concentrated in vacuo. The residue was purified by silica gel column chromatography (PE/EtOAc (v/v)=3/1) to give the title compound as a white solid (1.1 g, 80%). The compound was characterized by the following spectroscopic data:

MS (ESI, pos.ion) m/z: 378.2 [M+H]⁺; and
¹H NMR (400 MHz, CDCl₃): δ 7.03 (s, 1H), 4.86-4.89 (m, 1H), 3.90-3.94 (m, 1H), 2.88 (br, 1H), 2.04-2.11 (m, 2H), 1.78 (s, 1H), 1.45 (s, 9H), 1.12-1.13 (d, J=6.4 Hz, 3H) ppm.

Step 9) the Preparation of Compound 1-12

To a cooled 0° C. solution of compound 1-6 (5.0 g, 21.8 mmol) and compound 1-6-2 (7.28 g, 26.17 mmol) in DCM (140 mL) was added TEA (4.54 mL, 32.7 mmol) dropwise. The mixture was stirred at 25° C. for 3.5 hours. After the reaction was completed, the mixture was quenched with H₂O (80 mL) and extracted with DCM (100 mL×3). The combined organic phases were dried over anhydrous Na₂SO₄ and concentrated in vacuo. The residue was purified by silica gel column chromatography (PE/EtOAc (v/v)=5/1) to give the title compound as a white solid (4.73 g, 52%). The compound was characterized by the following spectroscopic data:

MS (ESI, pos.ion) m/z: 426.3 [M+H]⁺; and
¹H NMR (400 MHz, CDCl₃): δ 7.78-7.75 (m, 2H), 7.65-7.63 (m, 2H), 5.53-5.15 (m, 2H), 4.49-4.39 (m, 1H), 3.59-3.54 (m, 1H), 2.31-2.21 (m, 2H), 2.12-2.01 (m, 1H), 1.98-1.85 (m, 1H), 1.45 (s, 9H), 1.12-1.13 (d, J=6.4 Hz, 3H) ppm.

Step 10) the Preparation of Compound 1-13

A mixture of compound 1-12 (4.73 g, 11.15 mmol) and ammonium acetate (8.6 g, 111.5 mmol) in toluene (40 mL) was stirred at 120° C. for 5 hours. After the reaction was completed, the mixture was cooled to rt, and to the mixture was added H₂O (50 mL). The resulting mixture was extracted with EtOAc (100 mL×3). The combined organic phases were dried over anhydrous Na₂SO₄ and concentrated in vacuo. The residue was purified by silica gel column chromatography (PE/EtOAc (v/v)=4/1) to give the title compound as a white solid (4.0 g, 88.4%). The compound was characterized by the following spectroscopic data:

MS (ESI, pos.ion) m/z: 406.3 [M+H]⁺; and
¹H NMR (400 MHz, CDCl₃): δ 7.55 (br, 2H), 7.46-7.48 (m, 2H), 7.22 (s, 1H), 4.93-4.96 (m, 1H), 3.95-3.97 (m, 1H), 2.08-2.22 (m, 2H), 1.83 (m, 2H), 1.49 (s, 9H), 1.16 (d, J=6.2 Hz, 3H) ppm.

Step 11) the Preparation of Compound 1-14

To a mixture of compound 1-13 (4.0 g, 9.85 mmol), 4,4,4',4'5,5,5',5'-octamethyl-2,2'-bi(1,3,2-dioxaborolane) (3.0 g, 11.81 mmol), Pd(dppf)Cl₂.CH₂Cl₂ (0.40 g, 0.49 mmol) and KOAc (2.41 g, 24.61 mmol) was added DMF (40 mL). The reaction mixture was stirred at 90° C. for 4.0 hours. After the reaction was completed, the reaction mixture was cooled to rt and diluted with EtOAc (50 mL). The resulting mixture was filtered through diatomite. To the filtrate was added water (150 mL), and the resulting mixture was extracted with EtOAc (50 mL×3). The combined organic phases were washed with brine (100 mL), dried over anhydrous Na₂SO₄ and concentrated in vacuo. The residue was purified by silica gel column chromatography (PE/EtOAc (v/v)=2/1) to give the title compound as a light yellow solid (3.4 g, 76.4%). The compound was characterized by the following spectroscopic data:

MS (ESI, pos.ion) m/z: 454.3 [M+H]⁺; and
¹H NMR (400 MHz, CDCl₃): δ 7.79-7.81 (d, J=8.0 Hz, 2H), 7.64 (br, 2H), 7.28 (s, 1H), 4.95-4.98 (m, 1H), 3.95-3.96 (m, 1H), 2.12-2.21 (m, 2H), 1.83 (br, 2H), 1.49 (s, 9H), 1.38 (s, 12H), 1.16 (d, J=6.2 Hz, 3H) ppm.

Step 12) the Preparation of Compound 1-15

To a solution of benzoquinone (10.0 g, 92.5 mmol) in DCM (100 mL) was added 1, 4-cyclopentadiene (9.20 g, 138.8 mmol) at −10° C. The mixture was stirred at −10° C. for 1 hour, and then stirred at 25° C. for further 0.5 hour. After the reaction was completed, the solvent was removed in vacuo, and to the residue was added 500 mL of hexane. The resulting mixture was stirred and then filtered. The filtrate was concentrated in vacuo to give the title compound as a light yellow solid (10.5 g, 65.2%) which was not purified for the next step.

MS (ESI, pos.ion) m/z: 175.1 [M+H]⁺; and
¹H NMR (400 MHz, CDCl₃): δ 6.57 (s, 2H), 6.68 (s, 2H), 3.55 (s, 2H), 3.22-3.21 (m, 2H), 1.56-1.42 (m, 2H) ppm.

Step 13) the Preparation of Compound 1-16

A mixture of compound 1-15 (5.50 g, 31.6 mmol) and sodium acetate (7.77 g, 94.7 mmol) in 100 mL of MeOH (100 mL) was stirred at 50° C. under N₂ for 3 hours. After the reaction was completed, the mixture was concentrated in vacuo. The residue was purified by silica gel column chromatography (DCM) to give the title compound as a white solid (5.10 g, 92.7%). The compound was characterized by the following spectroscopic data:

MS (ESI, pos.ion) m/z: 175.1 [M+H]⁺; and
¹H NMR (400 MHz, CDCl₃): δ 6.80-6.79 (m, 2H), 6.35 (s, 2H), 3.55 (s, 2H), 4.10-4.09 (m, 2H), 2.25-2.18 (m, 2H) ppm.

Step 14) the Preparation of Compound 1-17

A suspension of compound 1-16 (4.70 g, 27.0 mmol) and Pa/C (10%, 0.47 g) in 50 mL of MeOH was stirred at 25° C. under H₂ for 1.5 hours. After the reaction was completed, the mixture was filtered. The filtrate was concentrated in vacuo to give the title compound as a white solid (3.55 g, 74.6%). The compound was characterized by the following spectroscopic data:

¹H NMR (400 MHz, DMSO-d₆): δ 8.27 (s, 2H), 6.29 (s, 2H), 3.47 (s, 2H), 1.79-1.77 (m, 2H), 1.48-1.46 (m, 1H), 1.36-1.34 (m, 1H), 1.01-0.99 (m, 2H) ppm.

Step 15) the Preparation of Compound 1-18

To a cooled 0° C. solution of compound 1-17 (3.35 g, 19 mmol) in DCM (50 mL) was added pyridine (9.00 g, 114 mmol) and TfOH (21 g, 76 mmol) dropwise in turn. After the addition, the mixture was stirred at 25° C. for 1 hour. After the reaction was completed, to the mixture was added 50 mL of DCM. The resulting mixture was washed with brine (80 mL). The separated organic phase was dried over anhydrous Na₂SO₄ and concentrated in vacuo. The residue was purified by silica gel column chromatography (PE/DCM (v/v)=10/1) to give the title compound as colorless oil (8.2 g, 98.0%). The compound was characterized by the following spectroscopic data:

¹H NMR (400 MHz, CDCl₃): δ 7.05 (s, 2H), 3.71-3.70 (m, 2H), 2.05-2.02 (m, 2H), 1.90-1.87 (m, 1H), 1.69-1.68 (m, 1H), 1.38-1.34 (m, 2H) ppm.

Step 16) the Preparation of Compound 1-19

To a mixture of compound 1-14 (2.4 g, 5.29 mmol), compound 1-18 (2.33 g, 5.29 mmol), Pd(PPh₃)₄ (367 mg, 0.32 mmol) and potassium carbonate (1.83 g, 13.24 mmol) was added DME (28 mL) and pure water (7 mL) under N₂.

The reaction mixture was stirred at 90° C. for 3 hours. After the reaction was completed, the mixture was cooled at rt, and to the mixture was added EtOAc (50 mL) and water (20 mL). The resulting mixture was extracted with EtOAc (50 mL×3), The combined organic phases were washed with brine (50 mL), dried over anhydrous $Na_2SO_4$ and concentrated in vacuo. The residue was purified by silica gel column chromatography (PE/EtOAc (v/v)=2/1) to give the title compound as a white solid (2.42 g, 74%). The compound was characterized by the following spectroscopic data:

MS (ESI, pos.ion) m/z: 618.3 $[M+H]^+$; and $^1$H NMR (400 MHz, $CDCl_3$): δ 7.75 (m, 2H), 7.42-7.44 (d, J=8.0 Hz, 2H), 7.30 (s, 1H), 7.19-7.21 (d, J=8.0 Hz, 1H), 7.02-7.04 (d, J=8.0 Hz, 1H), 4.98-5.0 (br, 1H), 3.98 (br, 1H), 2.11-2.26 (m, 2H), 2.02-2.04 (m, 2H), 1.94 (br, 1H), 1.80-1.82 (d, J=8.0 Hz, 2H), 1.56-1.59 (m, 3H), 1.39-1.42 (m, 2H), 1.24 (s, 9H), 1.17 (d, 3H) ppm.

Step 17) the Preparation of Compound 1-20

To a mixture of compound 1-19 (200 mg, 0.32 mmol), 4,4,4',4',5,5,5',5'-octamethyl-2,2'-bi(1,3,2-dioxaborolane) (90.5 mg, 0.36 mmol), $Pd(dppf)Cl_2 \cdot CH_2Cl_2$ (13.2 mg, 0.016 mmol) and KOAc (79.4 mg, 0.81 mmol) was added DMF (4.0 mL) under $N_2$. The reaction mixture was stirred at 90° C. under $N_2$ for 3 hours. After the reaction was completed, the reaction was cooled to rt and to the mixture was added EtOAc (40 mL). The resulting mixture was filtered through diatomite. To the filtrate was added water (30 mL), and the resulting mixture was extracted with EtOAc (30 mL×3). The combined organic phases were washed with brine (50 mL), dried over anhydrous $Na_2SO_4$ and concentrated in vacuo. The residue was purified by silica gel column chromatography (PE/EtOAc (v/v)=3/1) to give the title compound as a light yellow solid (0.18 g, 95%). The compound was characterized by the following spectroscopic data:

MS (ESI, pos.ion) m/z: 596.3 $[M+H]^+$; and $^1$H NMR (400 MHz, $CDCl_3$): δ 7.72 (m, 2H), 7.57-7.59 (d, J=8.0 Hz, 1H), 7.48-7.50 (d, 2H), 7.29 (s, 1H), 7.15-7.17 (d, J=8.0 Hz, 1H), 4.98-5.0 (br, 1H), 3.98 (br, 1H), 2.11-2.26 (m, 2H), 2.02-2.04 (m, 2H), 1.94 (br, 1H), 1.80-1.82 (d, J=8.0 Hz, 2H), 1.56-1.59 (m, 3H), 1.39-1.42 (m, 11H), 1.24 (s, 12H), 1.17 (d, 3H) ppm.

Step 18) the Preparation of Compound 1-21

To a mixture of compound 1-20 (270.9 mg, 0.46 mmol), compound 1-11 (188.7 mg, 0.5 mmol), $Pd(PPh_3)_4$ (26.3 mg, 0.023 mmol) and potassium carbonate (158 mg, 1.14 mmol) was added EtOH (12.0 mL) and pure water (3.0 mL) under $N_2$. The reaction mixture was stirred at 90° C. under $N_2$ for 3 hours. After the reaction was completed, the mixture was cooled at rt, and to the mixture was added EtOAc (30 mL) and water (10 mL) in turn. The resulting mixture was extracted with EtOAc (30 mL×3), The combined organic phases were washed with brine (50 mL), dried over anhydrous $Na_2SO_4$ and concentrated in vacuo. The residue was purified by silica gel column chromatography (DCM/MeOH (v/v)=60/1) to give the title compound as a white solid (236 mg, 72%). The compound was characterized by the following spectroscopic data:

MS (ESI, pos.ion) m/z: 360.3 $[M+H]^{2+}$; and $^1$H NMR (400 MHz, $CDCl_3$): δ 7.72-7.75 (m, 3H), 7.49-7.51 (d, J=8.0 Hz, 3H), 7.24 (s, 1H), 6.99 (s, 1H), 4.95-5.03 (m, 2H), 3.98 (br, 2H), 3.63 (m, 2H), 2.11-2.27 (m, 4H), 1.64-1.89 (m, 10H), 1.27 (s, 18H), 1.20 (d, J=6.3 Hz, 6H) ppm.

Step 19) the Preparation of Compound 1-22

To a solution of compound 1-21 (236 mg, 0.33 mmol) in 4 mL of EtOAc was added a solution of HCl in EtOAc (5 mL, 3 mol/L) at 25° C. The reaction was stirred at 25° C. for 8 hours. After the reaction was completed, the mixture was concentrated in vacuo to give the title compound as a light yellow solid (195 mg, 90%) which was used directly for the next step. The compound was characterized by the following spectroscopic data:

MS (ESI, pos.ion) m/z: 519.2 $[M+1]^+$.

Step 20) the Preparation of Compound 1-23

To a cooled 0° C. mixture of compound 1-22 (194.2 mg, 0.29 mmol), compound 1-22-2 (107.6 mg, 0.61 mmol), EDCI (117.7 mg, 0.61 mmol), HOAT (59.7 mg, 0.44 mmol) and 20 mL of DCM was added DIPEA (0.4 mL, 2.34 mmol) dropwise. After the addition, the mixture was stirred at 25° C. for 3.0 hours. After the reaction was completed, to the mixture was added DCM (20 mL), and washed with aqueous $NH_4Cl$ solution (15 mL) and saturated brine (15 mL) in turn. The organic phases was dried over anhydrous $Na_2SO_4$ and concentrated in vacuo. The residue was purified by silica gel column chromatography (DCM/MeOH (v/v)=60/1) to give the title compound as a white foam (104 mg, 43%).

MS (ESI, pos.ion) m/z: 417.3 $[M+H]^{2+}$; and $^1$H NMR (400 MHz, $CDCl_3$): δ 7.85-7.87 (d, J=8.0 Hz, 2H), 7.47 (m, 3H), 7.38 (s, 1H), 7.18 (br, 2H), 5.16-5.22 (br, 2H), 4.64 (br, 2H), 4.19-4.24 (m, 2H), 3.69 (s, 6H), 3.59-3.57 (m, 2H), 3.24 (br, 2H), 2.33-2.40 (m, 4H), 2.24-2.26 (m, 4H), 1.73-1.75 (m, 4H), 1.51 (m, 2H), 1.16 (m, 6H), 0.97-1.05 (m, 12H) ppm.

Example 2

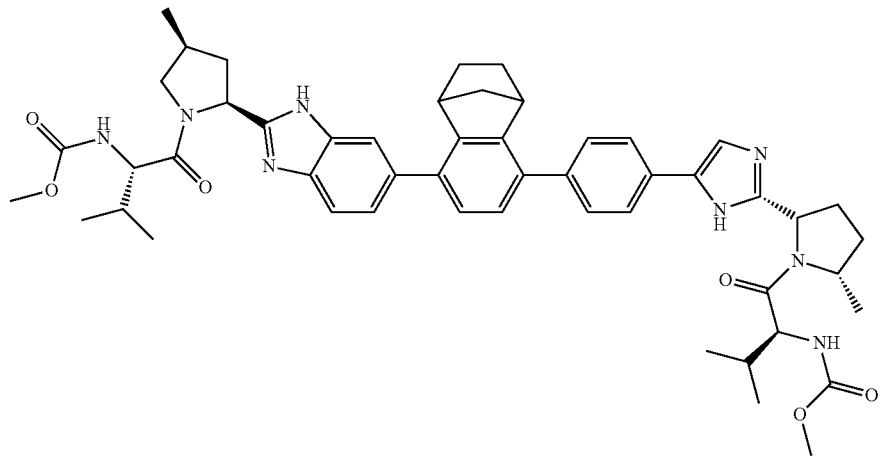

Synthetic Route:
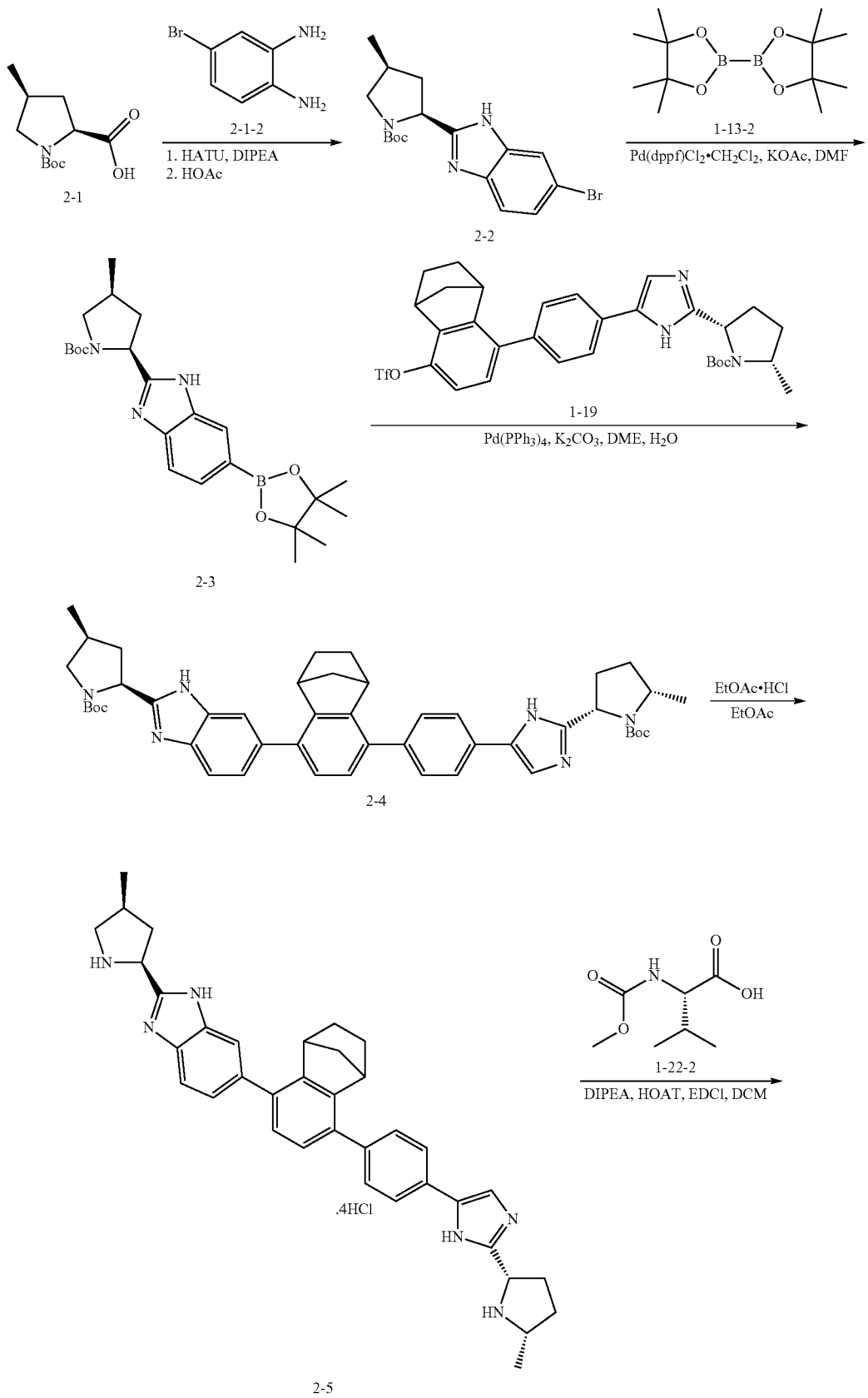

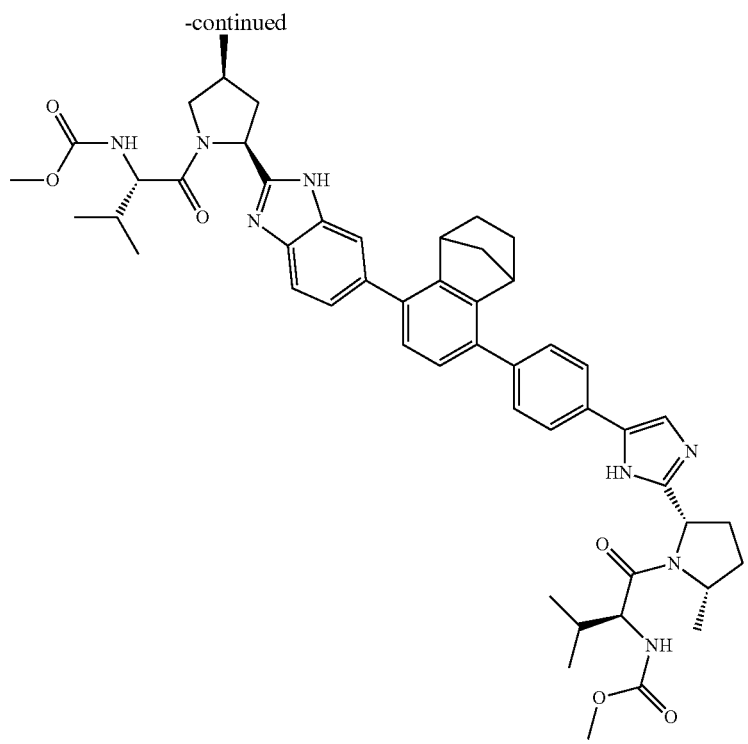

2-6

Step 1) the Preparation of Compound 2-2

To a cooled 0° C. solution of compound 2-1(13.3 g, 47.1 mmol), HATU (26.5 g, 69 mmol) in 150 mL of THF was added DIPEA (9 mL, 51.1 mmol) dropwise. After the addition, the mixture was stirred at 0° C. for 0.5 hour, and then to the mixture was added a solution of compound 2-1-2 (10 g, 53.5 mmol) in THF (20 mL) After the addition, the mixture was stirred at 25° C. for 4.0 hours, quenched with little water, removed the THF and then to the mixture was added water (50 mL). To the residue was added water (50 mL), and the resulting mixture was extracted with EtOAc (60 mL×3). The combined organic phases were washed with brine (100 mL), dried over anhydrous $Na_2SO_4$ and concentrated in vacuo. The residue was dissolved in 100 mL of acetic acid, and the resulting mixture was stirred at 40° C. for 12 hours. Then the mixture was concentrated in vacuo to remove the acetic acid. To the residue was added saturate aqueous $NaHCO_3$ solution (100 mL), and the resulting mixture was extracted with EtOAc (100 mL×3). The combined organic phases were washed with brine (100 mL), dried over anhydrous $Na_2SO_4$ and concentrated in vacuo. The residue was purified by silica gel column chromatography (PE/EtOAc (v/v)=2/1) to give the title compound as a light yellow solid (17.32 g, 85%). The compound was characterized by the following spectroscopic data:

$^1$H NMR (400 MHz, $CDCl_3$): δ 7.68 (s, 1H), 7.42-7.40 (m, 1H), 7.30-7.28 (m, 1H), 5.11-5.09 (m, 1H), 3.45-3.43 (m, 2H), 2.94-2.93 (m, 1H), 2.21-2.18 (m, 2H), 2.01-1.91 (m, 1H), 1.49 (s, 9H), 1.23 (d, 3H) ppm.

Step 2) the Preparation of Compound 2-3

To a mixture of compound 2-2 (4.0 g, 10.55 mmol), 4,4,4',4',5,5,5',5'-octamethyl-2,2'-bi(1,3,2-dioxaborolane) (2.95 g, 11.6 mmol), $Pd(dppf)Cl_2·CH_2Cl_2$ (430.5 mg, 0.528 mmol) and KOAc (2.59 g, 26.37 mmol) was added DMF (40 mL) under $N_2$. The reaction mixture was stirred at 90° C. under $N_2$ for 4.0 hours. After the reaction was completed, the reaction was cooled to rt, and to the mixture was added EtOAc (250 mL). The resulting mixture was filtered through diatomite. To the filtrate was added water (150 mL), and the resulting mixture was extracted with EtOAc (50 mL×3). The combined organic phases were washed with brine (150 mL), dried over anhydrous $Na_2SO_4$ and concentrated in vacuo. The residue was purified by silica gel column chromatography (PE/EtOAc (v/v)=2/1) to give the title compound as a white solid (3.83 g, 85%). The compound was characterized by the following spectroscopic data:

MS (ESI, pos.ion) m/z: 428.3 $[M+H]^+$;

$^1$H NMR (400 MHz, $CDCl_3$): δ 7.70 (s, 1H), 7.44-7.46 (m, 1H), 7.32-7.30 (m, 1H), 5.13-5.11 (m, 1H), 3.47-3.45 (m, 2H), 2.95-2.94 (m, 1H), 2.21-2.18 (m, 2H), 2.01-1.91 (m, 1H), 1.49 (s, 9H), 1.28 (s, 12H), 1.23 (d, 3H) ppm.

Step 3) the Preparation of Compound 2-4

To a mixture of compound 1-19 (147 mg, 0.24 mmol), compound 2-3 (102 mg, 0.24 mmol), $Pd(PPh_3)_4$ (13.9 mg, 0.012 mmol) and potassium carbonate (82.8 mg, 0.6 mmol) was added DME (12.0 mL) and pure water (3.0 mL). The reaction mixture was stirred at 90° C. for 3 hours. After the reaction was completed, the mixture was cooled at rt, and to the mixture was added EtOAc (50 mL) and water (10 mL). The separated water phase was extracted with EtOAc (30 mL×3). The combined organic phases were washed with brine (50 mL), dried over anhydrous $Na_2SO_4$ and concentrated in vacuo. The residue was purified by silica gel column chromatography (DCM/MeOH (v/v)=60/1) to give the title compound as a light yellow solid (170 mg, 92.8%). The compound was characterized by the following spectroscopic data:

MS (ESI, pos.ion) m/z: 385.3 $[M+H]^{2+}$; and $^1$H NMR (400 MHz, $CDCl_3$): δ 7.52-7.54 (m, 5H), 7.39-7.41 (m, 3H), 7.31 (s, 2H), 5.15-5.17 (m, 1H), 4.99-

5.02 (m, 1H), 4.09-4.15 (dd, J=8.0 Hz, 4H), 3.63-3.66 (m, 4H), 2.04-2.22 (m, 6H), 1.74-1.76 (m, 4H), 1.51-1.53 (m, 18H), 1.37 (s, 3H), 1.13 (s, 3H) ppm.

Step 4) the Preparation of Compound 2-5

To a solution of compound 2-4 (164 mg, 0.21 mmol) in 4 mL of EtOAc was added HCl in EtOAc (3 mL, 3 mol/L) at 25° C. The reaction was stirred at 25° C. for 8 hours. After the reaction was completed, the mixture was concentrated in vacuo. The residue was diluted with EtOAc (5.0 mL), then the resulting mixture was filtered to give the title compound as light yellow powder (155 mg, 100%) which was used directly for the next step. The compound was characterized by the following spectroscopic data:

MS (ESI, pos.ion) m/z: 570.3 [M+1]$^+$.

Step 5) the Preparation of Compound 2-6

To a cooled 0° C. mixture of compound 2-5 (150 mg, 0.21 mmol), compound 1-22-2 (77 mg, 0.44 mmol), EDCI (84.6 mg, 0.44 mmol) and HOAT (42.9 mg, 0.32 mmol) and 20 mL of DCM was added DIPEA (0.29 mL, 1.68 mmol) dropwise. After the addition, the mixture was stirred at 25° C. for 3.0 hours. After the reaction was completed, to the mixture was added DCM (20 mL), and the resulting mixture was washed with aqueous NH$_4$Cl solution (30 mL) and brine (30 mL). The organic phases was dried over anhydrous Na$_2$SO$_4$ and concentrated in vacuo. The residue was purified by silica gel column chromatography (DCM/MeOH (v/v)=60/1) to give the title compound as a white foam solid (80 mg, 43.2%).

MS (ESI, pos.ion) m/z: 442.3 [M+H]$^{2+}$; and $^1$H NMR (400 MHz, CDCl$_3$): δ 7.50-7.52 (m, 6H), 7.39-7.42 (m, 3H), 7.30 (s, 1H), 5.21-5.24 (m, 4H), 3.7 (s, 6H), 3.50-3.64 (m, 3H), 2.98-3.02 (m, 2H), 2.51-2.60 (m, 1H), 2.32-2.41 (m, 1H), 2.17-2.20 (m, 4H), 2.04 (s, 1H), 1.91-1.96 (br, 2H), 1.58-1.66 (br, 6H), 1.29 (s, 3H), 1.14 (s, 3H), 0.81-0.85 (m, 12H) ppm.

Example 3

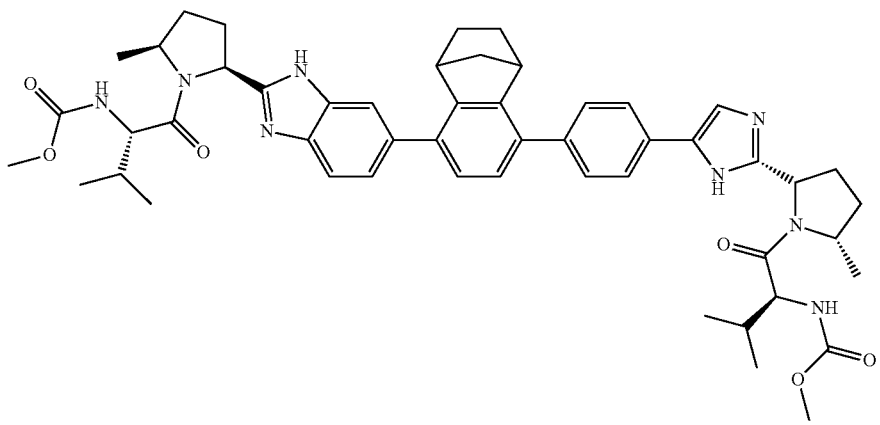

Synthetic Route:

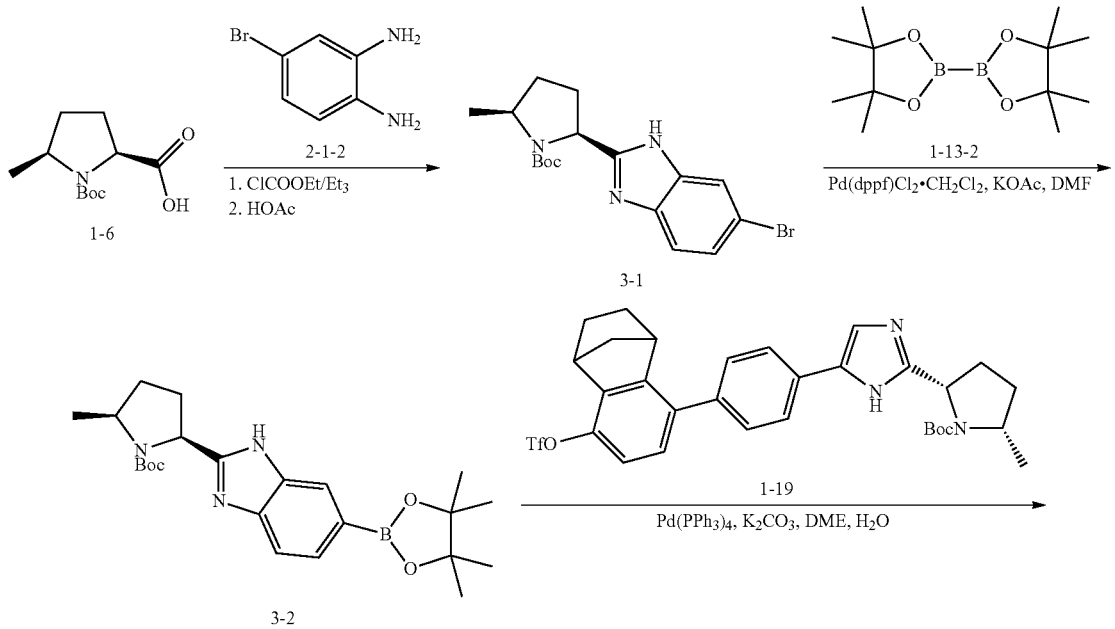

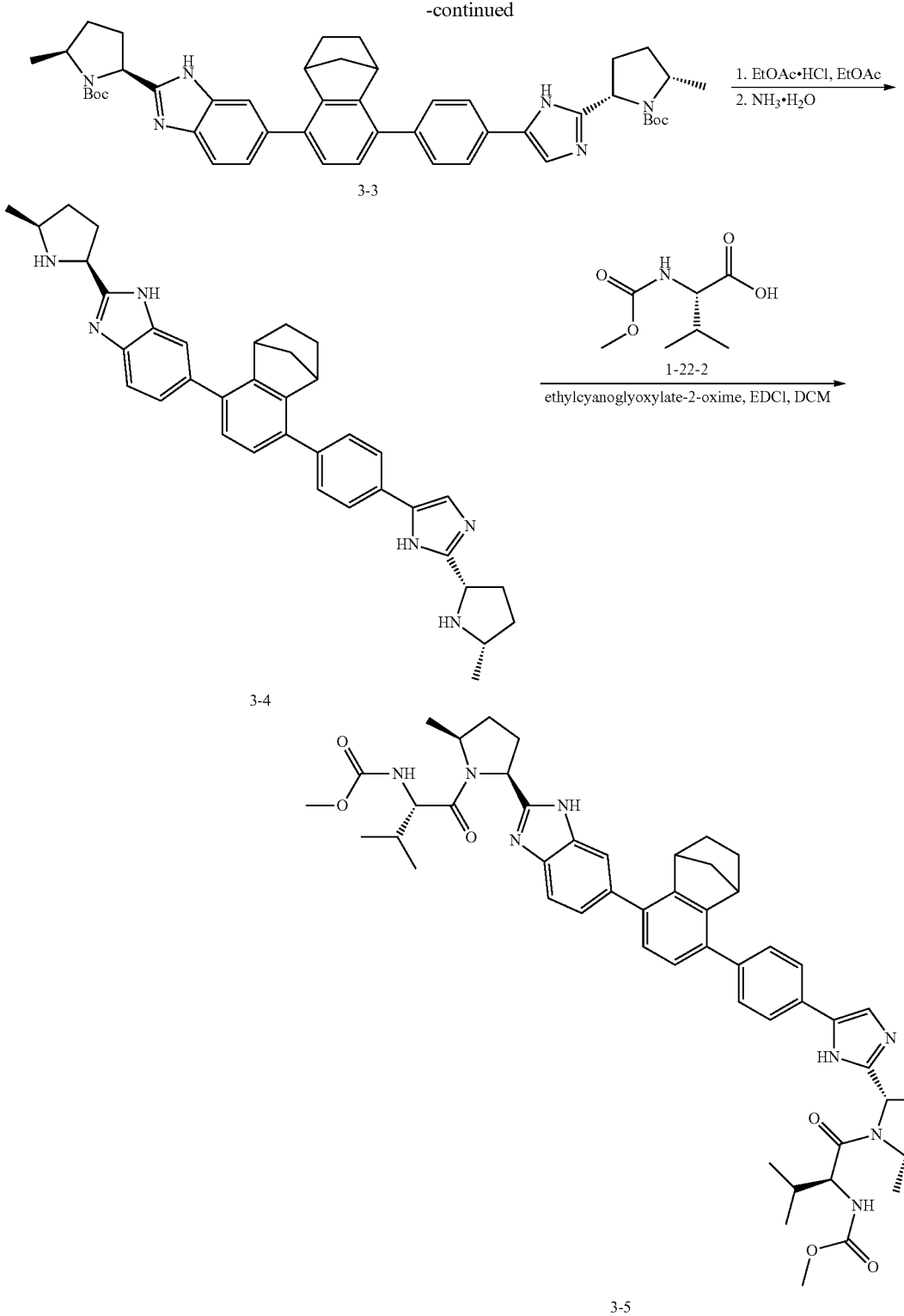

Step 1) the Preparation of Compound 3-1

To a cooled 0° C. solution of compound 1-6 (3.8 g, 16.57 mmol) in 50 mL of DCM was added ClCOOEt (1.58 mL, 16.57 mmol) and TEA (2.4 mL, 17.36 mmol) dropwise. After the addition, the mixture was stirred at 0° C. for 0.5 hour, and then to the mixture was added a solution of compound 2-1-2 (2.96 g, 15.78 mmol) in DCM (30 mL). Then the mixture was stirred at 25° C. for 4 hours. To the mixture was added water (20 mL). The resulting mixture was extracted with DCM (100 mL×3), the combined organic phases were dried over anhydrous $Na_2SO_4$ and concentrated in vacuo. The residue (4.2 g, 10.57 mmol) was dissolved in 50 mL of acetic acid, and the resulting mixture was stirred at 50° C. for 10 h. After the reaction was completed, the mixture was concentrated in vacuo to remove acetic acid. The residue was dissolved in EtOAc (100 mL), and the resulting mixture was washed with aqueous NaHCO$_3$ solution (50 mL×2). The separated organic phase was dried over anhydrous Na$_2$SO$_4$ and concentrated in vacuo. The residue was purified by silica gel column chromatography (PE/EtOAc (v/v)=4/1) to give the title compound as a light red solid (3.98 g, 66%). The compound was characterized by the following spectroscopic data:

MS (ESI, pos.ion) m/z: 381.3 [M+H]$^+$; and $^1$H NMR (400 MHz, CDCl$_3$): δ 7.71 (br, 1H), 7.43 (br, 1H), 7.30-7.32 (d, J=8.0 Hz, 1H), 5.07-5.10 (m, 1H), 3.95-3.97 (m, 1H), 2.94 (br, 1H), 2.12-2.26 (m, 2H), 1.86 (br, 1H), 1.49 (s, 9H), 1.14 (d, J=6.4 Hz, 3H) ppm.

Step 2) the Preparation of Compound 3-2

To a mixture of compound 3-1 (5.66 g, 14.88 mmol), 4,4,4',4',5,5,5',5'-octamethyl-2,2'-bi(1,3,2-dioxaborolane) (4.54 g, 17.86 mmol), Pd(dppf)Cl$_2$·CH$_2$Cl$_2$ (0.6 g, 0.744 mmol) and KOAc (3.65 g, 37.2 mmol) was added DMF (40 mL) under N$_2$, the reaction mixture was stirred at 90° C. under N$_2$ for 4 hours. After the reaction was completed, the reaction was cooled to rt and to the mixture was added EtOAc (200 mL). The resulting mixture was filtered through diatomite. To the filtrate was added water (150 mL), and The resulting mixture was extracted with EtOAc (50 mL×3). The combined organic phases were washed with brine (100 mL×3), dried over anhydrous Na$_2$SO$_4$ and concentrated in vacuo. The residue was purified by silica gel column chromatography (PE/EtOAc (v/v)=2/1) to give the title compound as a white solid (4.0 g, 63%). The compound was characterized by the following spectroscopic data:

MS (ESI, pos.ion) m/z: 428.3 [M+1]$^+$; and $^1$H NMR (400 MHz, CDCl$_3$): δ 7.75 (br., 1H), 7.53 (br., 1H), 7.32-7.34 (d, J=8.0 Hz, 1H), 5.07-5.10 (m, 1H), 3.95-3.97 (m, 1H), 2.94 (br., 1H), 2.12-2.26 (m, 2H), 1.86 (br., 1H), 1.49 (s, 9H), 1.28 (s, 12H), 1.14 (d, J=6.4 Hz, 3H) ppm.

Step 3) the Preparation of Compound 3-3

To a mixture of compound 1-19 (300 mg, 0.49 mmol), compound 3-2 (207.6 mg, 0.49 mmol), Pd(PPh$_3$)$_4$ (56 mg, 0.049 mmol) and potassium carbonate (201 mg, 1.46 mmol) was added DME (8.0 mL) and pure water (2.0 mL) in turn under N$_2$. The reaction mixture was stirred at 90° C. under N$_2$ for 3 hours. After the reaction was completed, the mixture was cooled at rt, and to the mixture was added EtOAc (50 mL) and water (40 mL). The separated water phase was extracted with EtOAc (20 mL×3). The combined organic phases were washed with brine (50 mL), dried over anhydrous Na$_2$SO$_4$ and concentrated in vacuo. The residue was purified by silica gel column chromatography (PE/EtOAc (v/v)=1/1) to give the title compound as a light yellow solid (210 mg, 55%). The compound was characterized by the following spectroscopic data:

MS (ESI, pos.ion) m/z: 385.3 [M+H]$^{2+}$; and $^1$H NMR (400 MHz, CDCl$_3$): δ 7.68-7.80 (br, 3H), 7.52-7.54 (d, J=8.0 Hz, 2H), 7.39-7.41 (d, J=8.0 Hz, 1H), 7.27-7.29 (m, 4H), 5.15-5.18 (m, 1H), 4.99-5.02 (m, 1H), 3.91-4.04 (br., 2H), 3.64-3.66 (d, J=8.0 Hz, 2H), 2.96-3.15 (m, 4H), 2.11-2.19 (m, 4H), 2.03-2.07 (m, 4H), 1.81-1.97 (m, 2H), 1.52 (s, 18H), 1.14 (d, J=6.3 Hz, Step 4) the Preparation of Compound 3-4

To a solution of compound 3-3 (190 mg, 0.25 mmol) in 4 mL of EtOAc was added a solution of HCl in EtOAc (5 mL, 3 mol/L) at 25° C. The reaction was stirred at 25° C. for 8 hours. After the reaction was completed, the mixture was concentrated in vacuo. The residue was washed with EtOAc (10 mL), and then filtered to give compound 3-4 hydrochloric salt as light yellow powder (161 mg, 91%). The powder was dissociated with ammonium hydroxide (10 mL) and filter to give the title compound as a white solid which was used directly for the next step. The compound was characterized by the following spectroscopic data:

MS (ESI, pos.ion) m/z: 569.3 [M+1]$^+$.

Step 5) the Preparation of Compound 3-5

To a cooled 0° C. solution of compound 3-4 (150 mg, 0.21 mmol) and compound 1-22-2 (92.4 mg, 0.53 mmol) in DCM (10 mL) was added a solution of EDCI (101.2 mg, 0.53 mmol) and ethyl cyanoglyoxylate-2-oxime (15.0 mg, 0.11 mmol) in DCM (10 mL) dropwise. After the addition, the mixture was stirred at 0° C. for 5 hours. After the reaction was completed, to the mixture was added DCM (20 mL), and the resulting mixture was washed with saturated aqueous NH$_4$Cl solution (20 mL) and saturated brine (20 mL). The organic phase was dried over anhydrous Na$_2$SO$_4$ and concentrated in vacuo. The residue was purified by silica gel column chromatography (DCM/MeOH (v/v)=60/1) to give the title compound as a white foam solid (140 mg, 76%). The compound was characterized by the following spectroscopic data:

MS (ESI, pos.ion) m/z: 442.3 [M+H]$^{2+}$; and $^1$H NMR (400 MHz, CDCl$_3$): δ 7.89-7.91 (m, 2H), 7.71-7.74 (m, 2H), 7.52-7.59 (m, 4H), 7.31-7.33 (m, 2H), 5.40-5.44 (m, 2H), 4.69-4.71 (m, 1H), 4.21-4.30 (br, 1H), 3.73 (s, 6H), 3.49-3.54 (m, 2H), 3.0-3.02 (d, J=8.0 Hz, 4H), 2.51-2.60 (br, 1H), 2.32-2.41 (br, 1H), 2.17-2.20 (br, 2H), 2.10 (s, 1H), 2.04 (s, 1H), 1.91-1.96 (br, 2H), 1.58-1.66 (br, 4H), 1.24-1.27 (m, 2H), 1.14 (s, 6H), 0.81-0.85 (m, 12H) ppm.

Example 4

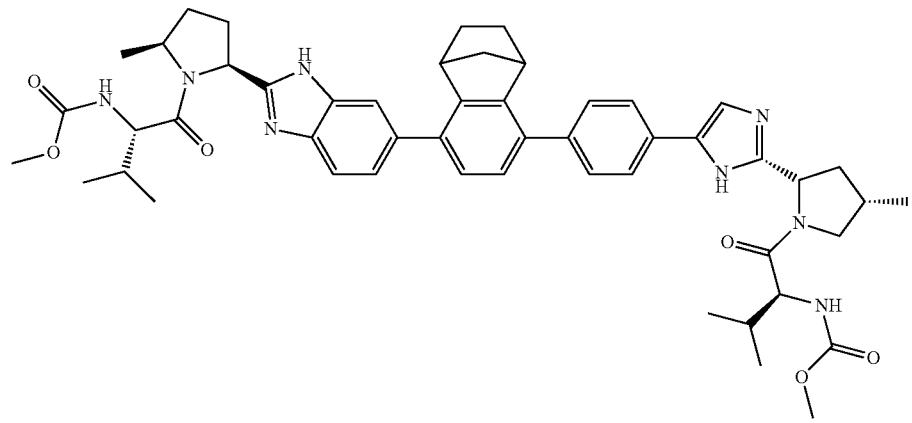

Synthetic Route:
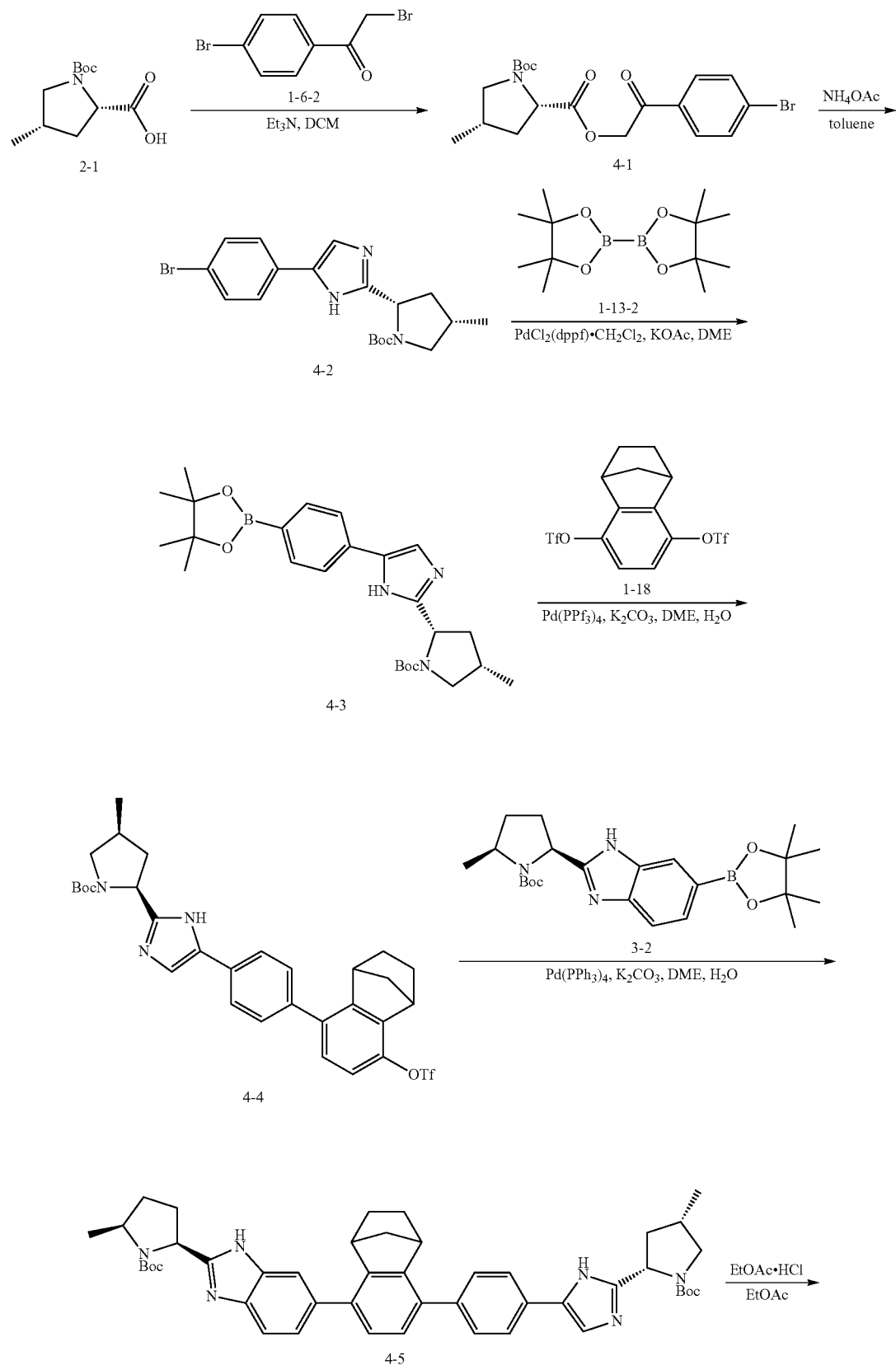

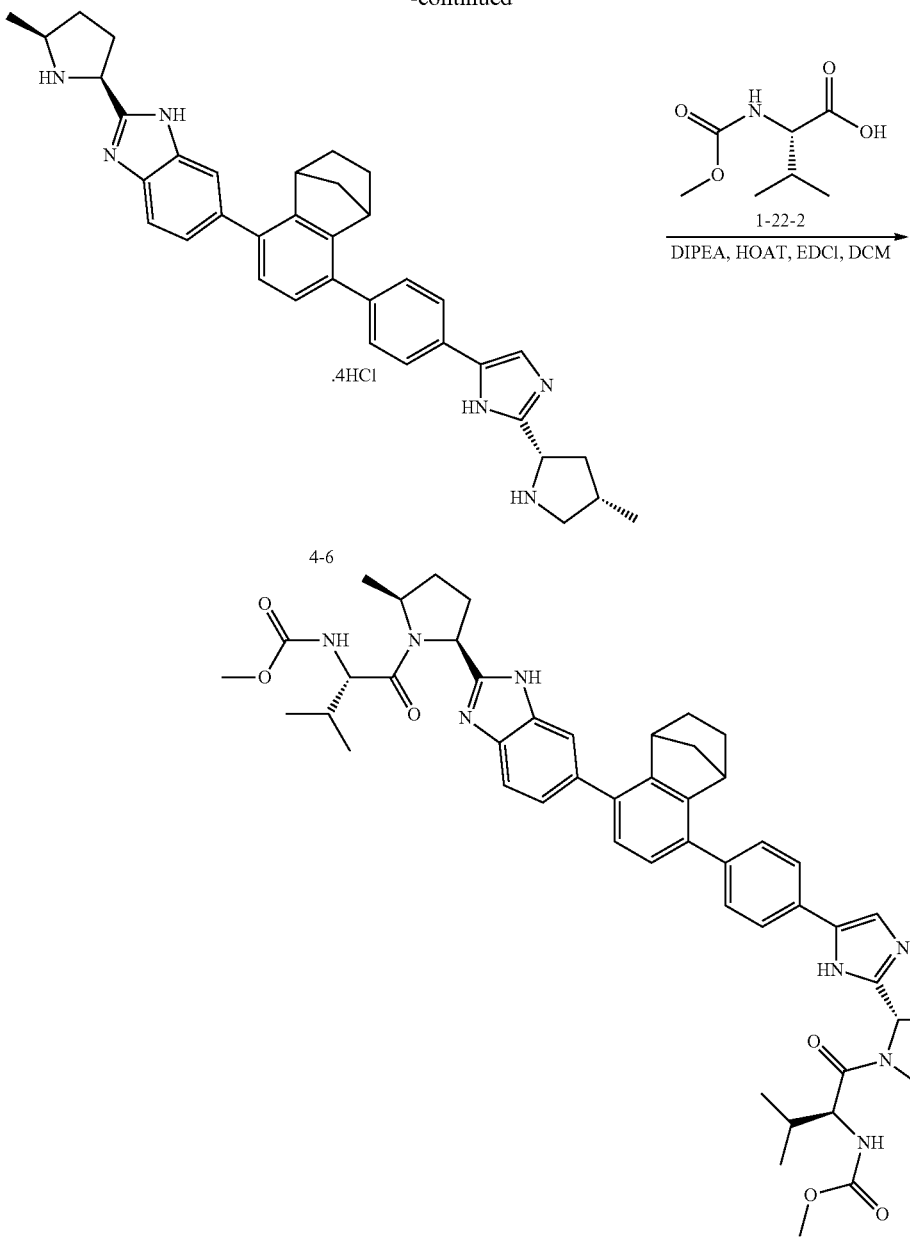

Step 1) the Preparation of Compound 4-1

To a cooled 0° C. solution of compound 2-1 (3.0 g, 13.1 mmol) and compound 1-6-2 (3.63 g, 13.1 mmol) in 40 mL of DCM was added TEA (3.9 mL, 26.3 mol) dropwise. After the addition, the mixture was stirred at 25° C. for 2 hours. After the reaction was completed, the mixture was quenched with water (50 mL). The resulting mixture was extracted with DCM (50 mL×3). The combined organic phases were dried over anhydrous $Na_2SO_4$ and concentrated in vacuo to give the crude product (3.27 g) which was used directly for the next step. The compound was characterized by the following spectroscopic data:

MS (ESI, pos.ion) m/z: 426.1[M+H]$^+$.

Step 2) the Preparation of Compound 4-2

A mixture of compound 4-1 (3.27 g, 7.67 mmol) and ammonium acetate (5.1 g, 62 mmol) in 34 mL of toluene was stirred at 110° C. for 5 hours. After the reaction was completed, the reaction mixture was cooled to rt, and to the mixture was added water (50 mL). The resulting mixture was extracted with EtOAc (80 mL×3). The combined organic phases were dried over anhydrous $Na_2SO_4$. The residue was purified by silica gel column chromatography (PE/EtOAc (v/v)=4/1) to give the title compound as a white solid (2.8 g, 90%). The compound was characterized by the following spectroscopic data:

MS (ESI, pos.ion) m/z: 407.3 [M+H]$^+$; and $^1$H NMR (400 MHz, CDCl$_3$): δ 7.45 (m, 4H), 7.20 (s, 1H), 4.93 (t, J=8.2 Hz, 1H), 3.88-3.66 (m, 1H), 2.90 (t, J=8 Hz, 1H), 2.50-2.47 (m, 2H), 2.27-2.25 (m, 1H), 1.48 (s, 7H), 1.26 (s, 2H), 1.12 (d, J=6.2 Hz, 3H) ppm.

Step 3) the Preparation of Compound 4-3

To a mixture of compound 4-2 (2.8 g, 6.9 mmol), 4,4,4',4',5,5,5',5'-octamethyl-2,2'-bi(1,3,2-dioxaborolane) (1.93 g, 7.6 mmol), Pd(dppf)Cl$_2$·CH$_2$Cl$_2$ (0.28 g, 0.34 mmol) and KOAc (1.7 g, 17.25 mmol) was added DME (30 mL) under N$_2$. The reaction mixture was stirred at 90° C. under N$_2$ for 2 hours. After the reaction was completed, the reaction was cooled to rt and diluted with EtOAc (40 mL). The resulting mixture was filtered through diatomite. To the filtrate was added water (30 mL), and the resulting mixture was extracted with EtOAc (40 mL×3). The combined organic phases were washed with saturated brine (60 mL), dried over anhydrous Na$_2$SO$_4$ and concentrated in vacuo. The residue was diluted in (PE/EtOAc (v/v)=2/1, 20 mL), then the resulting mixture was filtered. The filtrate was concentrated in vacuo to give the title compound as a yellow foam solid (3.4 g, 100%). The compound was characterized by the following spectroscopic data:

MS (ESI, pos.ion) m/z: 454.4 [M+H]$^+$; and
$^1$H NMR (400 MHz, CDCl$_3$): δ 7.35 (m, 4H), 7.10 (s, 1H), 4.93 (t, J=8.2 Hz, 1H), 3.88-3.66 (m, 1H), 2.90 (t, J=8.0 Hz, 1H), 2.50-2.47 (m, 2H), 2.27-2.25 (m, 1H), 1.48 (s, 9H), 1.26 (s, 12H), 1.02 (d, J=6.2 Hz, 3H) ppm.

Step 4) the Preparation of Compound 4-4

To a mixture of compound 4-3 (3.4 g, 7.7 mmol), compound 1-18 (3.4 g, 7.7 mmol), Pd(PPh$_3$)$_4$ (450 mg, 0.38 mmol) and potassium carbonate (2.1 g, 15.4 mmol) was added DME (32 mL) and pure water (8 mL) under N$_2$. The reaction mixture was stirred at 90° C. for 3 hours under N$_2$. After the reaction was completed, the mixture was cooled to rt, and to the mixture was added EtOAc (100 mL) and water (40 mL). The separated aqueous phase was extracted with EtOAc (50 mL×3). The combined organic phases were washed with brine (100 mL), dried over anhydrous Na$_2$SO$_4$ and concentrated in vacuo. The residue was purified by silica gel column chromatography (PE/EtOAc (v/v)=2/1) to give the title compound as a light yellow solid (2.87 g, 62%). The compound was characterized by the following spectroscopic data:

MS (ESI, pos.ion) m/z: 618.7 [M+H]$^+$; and
$^1$H NMR (400 MHz, CDCl$_3$): δ 7.85-7.79 (m, 2H), 7.42-7.41 (m, 2H), 7.27 (s, 1H), 7.19 (d, J=8.6 Hz, 1H), 7.02 (d, J=8.6 Hz, 1H), 4.97 (t, J=8.0 Hz, 1H), 3.92-3.73 (m, 1H), 2.94-2.89 (m, 1H), 2.63 (m, 1H), 2.28 (m, 2H), 2.02 (d, J=7.1 Hz, 2H), 1.58 (m, 1H), 1.50 (m, 3H), 1.41 (d, J=10.7 Hz, 2H), 1.24 (s, 9H), 1.13 (d, J=6.1 Hz, Step 5) the Preparation of Compound 4-5

To a mixture of compound 4-4 (125.4 mg, 0.2 mmol), compound 3-2 (85.4 mg, 0.2 mmol), Pd(PPh$_3$)$_4$ (11.6 mg, 0.01 mmol) and potassium carbonate (69 mg, 0.5 mmol) was added DME (12.0 mL) and pure water (3.0 mL) under N$_2$. The reaction mixture was stirred at 90° C. under N$_2$ for 3.0 hours. After the reaction was completed, the mixture was cooled at rt, to the mixture was added EtOAc (20 mL) and water (10 mL). The separated water phase was extracted with EtOAc (50 mL×3). The combined organic phases were washed with brine (50 mL), dried over anhydrous Na$_2$SO$_4$ and concentrated in vacuo. The residue was purified by silica gel column chromatography (DCM/MeOH (v/v)=60/1) to give the title compound as a light yellow solid (150 mg, 96.8%). The compound was characterized by the following spectroscopic data:

MS (ESI, pos.ion) m/z: 385.3 [M+H]$^{2+}$; and
$^1$H NMR (400 MHz, CDCl$_3$): δ 7.52-7.54 (m, 5H), 7.39-7.41 (m, 3H), 7.31 (s, 2H), 5.15-5.17 (m, 1H), 4.99-5.02 (m, 1H), 4.09-4.15 (dd, J=8.0 Hz, 4H), 3.63-3.66 (m, 4H), 2.04-2.22 (m, 6H), 1.74-1.76 (m, 4H), 1.51-1.53 (m, 18H), 1.37 (s, 3H), 1.13 (s, 3H) ppm.

Step 6) the Preparation of Compound 4-6

To a solution of compound 4-5 (150 mg, 0.2 mmol) in 4 mL of EtOAc was added a solution of HCl in EtOAc (3 mL, 3 mol/L) at 25° C. The reaction was stirred at 25° C. for 8 hours. After the reaction was completed, the mixture was concentrated in vacuo. The residue was washed with EtOAc (10 mL), then filtered to give the title compound as light yellow powder (110 mg, 78.6%) which was used directly for the next step. The compound was characterized by the following spectroscopic data:

MS (ESI, pos.ion) m/z: 569.3 [M+H]$^+$.

Step 7) the Preparation of Compound 4-7

To a cooled 0° C. mixture of compound 4-6 (150 mg, 0.21 mmol), compound 1-22-2 (77 mg, 0.44 mmol), EDCI (84.6 mg, 0.44 mmol), HOAT (42.9 mg, 0.32 mmol) and 20 mL of DCM was added DIPEA (0.29 mL, 1.68 mmol) dropwise. After the addition, the mixture was stirred at 25° C. for 3.0 hours. After the reaction was completed, to the mixture was added DCM (20 mL), and the resulting mixture was washed with aqueous NH$_4$Cl solution (20 mL) and saturated brine (20 mL). The separated organic phase was dried over anhydrous Na$_2$SO$_4$ and concentrated in vacuo. The residue was purified by silica gel column chromatography (DCM/MeOH (v/v)=60/1) to give the title compound as a white foam solid (80 mg, 43.2%). The compound was characterized by the following spectroscopic data:

MS (ESI, pos.ion) m/z: 442.3 [M+H]$^{2+}$; and
$^1$H NMR (400 MHz, CDCl$_3$): δ 7.48-7.50 (m, 6H), 7.36-7.39 (m, 3H), 7.28 (s, 1H), 5.19-5.24 (m, 4H), 3.73 (s, 6H), 3.49-3.64 (m, 3H), 3.0-3.02 (m, 2H), 2.51-2.60 (m, 1H), 2.32-2.41 (m, 1H), 2.17-2.20 (m, 4H), 2.04 (s, 1H), 1.91-1.96 (br, 2H), 1.58-1.66 (br, 6H), 1.29 (s, 3H), 1.14 (s, 3H), 0.81-0.85 (m, 12H) ppm.

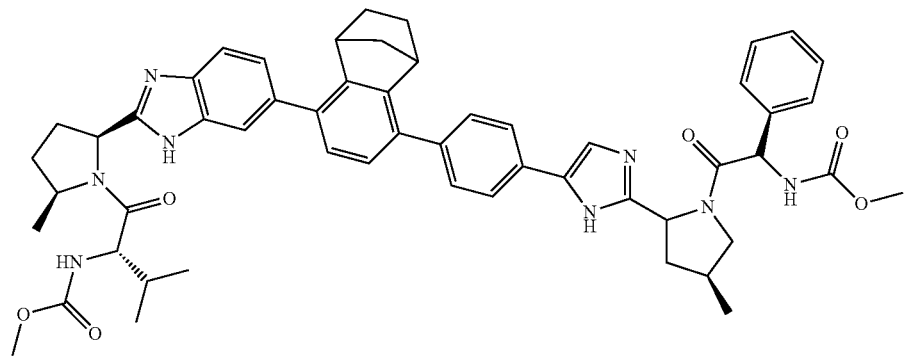

Example 5
Synthetic Route:
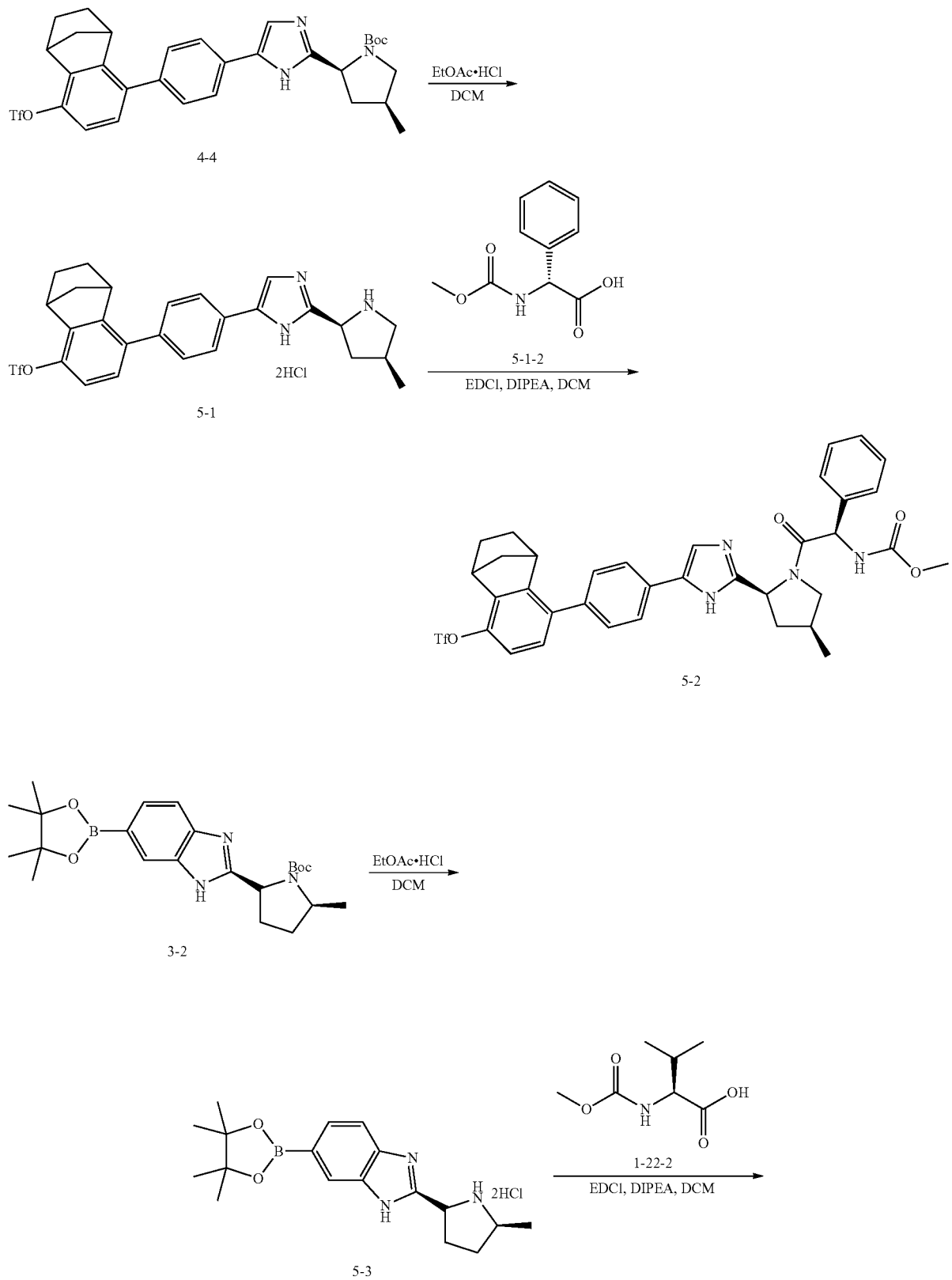

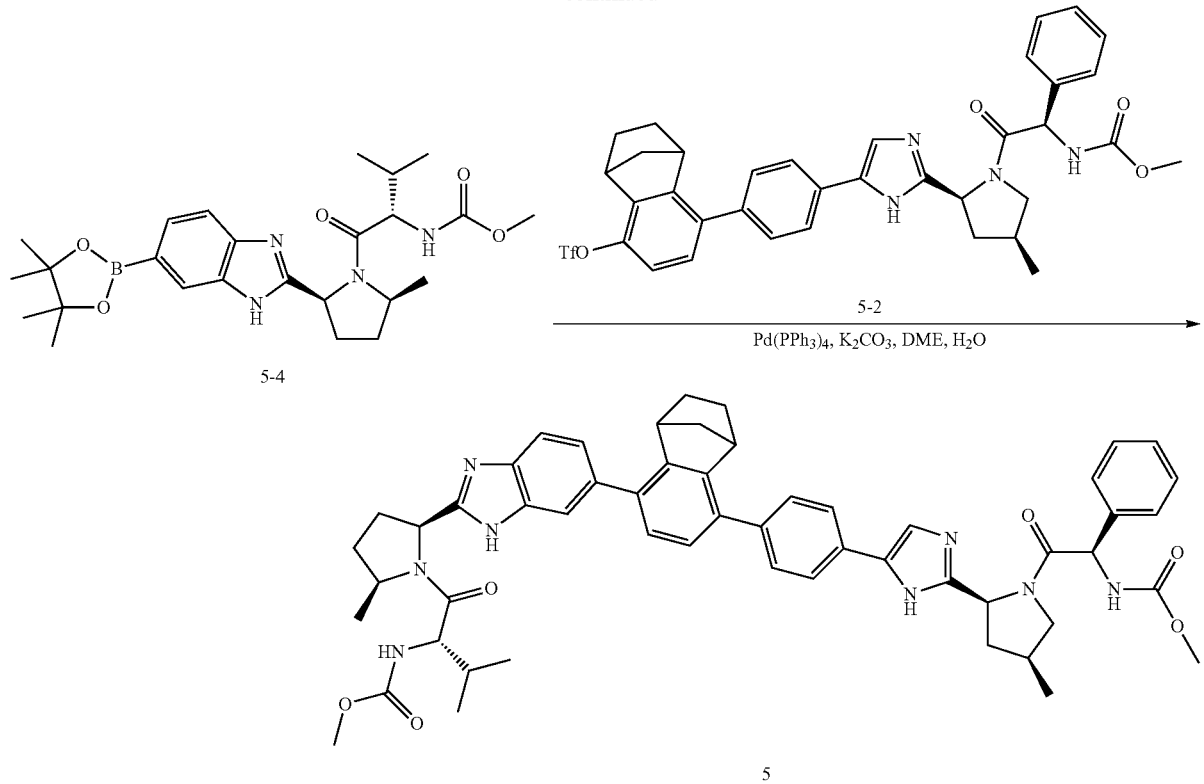

Step 1) the Preparation of Compound 5-1

To a solution of compound 4-4 (2.02 g, 3.27 mmol) in DCM (30 mL) was added a solution of HCl in EtOAc (12 mL, 4 mol/L) dropwise at 25° C. The reaction was stirred at 25° C. for 5.5 hours. After the reaction was completed, the reaction mixture was concentrated in vacuo. The residue was washed with EtOAc (15 mL), and then filtrated to give the title compound as an offwhite solid (1.4 g, 72%). The compound was characterized by the following spectroscopic data:

MS (ESI, pos. ion) m/z: 518.5[M+H]$^+$.

Step 2) the Preparation of Compound 5-2

To a mixture of compound 5-1 (295 mg, 0.5 mmol), compound 5-1-2 (101 mg, 0.53 mmol), EDCI (115 mg, 0.6 mmol) and DCM (10 mL) was added DIPEA (0.18 mL, 1 mmol) dropwise at −15° C. The reaction mixture was stirred at −15° C. for 1.0 hour and then at 25° C. for further 4.0 hours. Then to the reaction was added ammonia (6 mL), and the resulting mixture was stirred for 2 hours. The separated organic phase was washed with water (5 mL×2), dried over anhydrous Na$_2$SO$_4$ and concentrated in vacuo. The residue was purified by silica gel column chromatography (DCM/MeOH (v/v)=50/1) to give the title compound as a white solid (270 mg, 78%). The compound was characterized by the following spectroscopic data:

MS (ESI, pos. ion) m/z: 709.2 [M+H]$^+$; and $^1$H NMR (400 MHz, CDCl$_3$): δ 8.32-8.29 (m, 2H), 7.81 (s, 1H), 7.41-7.39 (m, 2H), 7.35 (s, 1H), 7.27-7.25 (m, 5H), 7.23 (s, 1H), 4.85-4.82 (m, 1H), 4.38-4.35 (m, 1H), 3.70 (s, 3H), 3.59-3.56 (m, 1H), 2.88-2.84 (m, 2H), 2.42-2.38 (m, 2H), 2.02-2.00 (m, 2H), 1.70-1.67 (m, 4H), 1.45-1.41 (m, 2H), 1.1 (d, J=4.3 Hz, 3H) ppm.

Step 3) the Preparation of Compound 5-3

To a solution of compound 3-2 (2.1 g, 4.92 mmol) in DCM (20 mL) was added a solution of HCl in EtOAc (8 mL, 4 mol/L) dropwise at 25° C. The reaction was stirred at 25° C. for 3.0 hours. After the reaction was completed, the reaction mixture was filtrated, and the filter cake was washed with EtOAc (5 mL) to give the title compound as a white solid (1.64 g, 83%). The compound was characterized by the following spectroscopic data:

MS (ESI, pos. ion) m/z: 328.3 [M+H]$^+$.

Step 4) the Preparation of Compound 5-4

To a mixture of compound 5-3 (386.3 mg, 0.97 mmol), compound 1-22-2 (184 mg, 1.05 mmol), EDCI (230 mg, 1.2 mmol) and DCM (10 mL) was added dropwise DIPEA (0.35 mL, 2 mmol) at −15° C. The reaction mixture was stirred at −15° C. for 1.0 hour and then at 25° C. for further 4.0 hours. Then to the reaction was added ammonia (6 mL), and the resulting mixture was stirred for 2.0 hours. The separated organic phase was washed with water (5 mL×2), dried over anhydrous Na$_2$SO$_4$ and concentrated in vacuo. The residue was purified by silica gel column chromatography (DCM/MeOH (v/v)=50/1) to give the title compound as a white solid (200 mg, 43%). The compound was characterized by the following spectroscopic data:

MS (ESI, pos. ion) m/z: 485.3 [M+H]$^+$; and $^1$H NMR (400 MHz, CDCl$_3$): δ 8.01 (br.s, 1H), 7.66 (s, 1H), 7.61 (d, J=4.0 Hz, 1H), 7.20 (d, J=4.0 Hz, 1H), 4.81-4.79 (m, 1H), 4.63-4.61 (m, 1H), 3.68 (s, 3H), 3.53-3.50 (m, 2H), 2.68-2.65 (m, 1H), 2.38-2.35 (m, 2H), 2.02-1.99 (m, 2H), 1.25 (s, 12H), 1.1 (d, J=4.4 Hz, 3H), 0.93 (d, J=4.4 Hz, 6H) ppm.

Step 5) the Preparation of Compound 5

A suspension of compound 5-2 (138 mg, 0.2 mmol), compound 5-4 (90 mg, 0.2 mmol), Pd(PPh$_3$)$_4$ (23 mg, 0.02 mmol) and K$_2$CO$_3$ (56 mg, 0.4 mmol) in a mixture solvent of DME (8 mL) and water (2 mL) was stirred at 90° C. under $N_2$ for 3.5 hours. After the reaction was completed, to the mixture was added DCM (30 mL) and water (20 mL). The separated organic phase was dried over anhydrous $Na_2SO_4$ and concentrated in vacuo. The residue was purified by silica gel column chromatography (DCM/MeOH (v/v)=50/1) to give the title compound as a light yellow solid (98 mg, 55%). The compound was characterized by the following spectroscopic data:

MS (ESI, pos. ion) m/z: 917.3[M+H]$^+$; and $^1$H NMR (400 MHz, CDCl$_3$): δ 8.33-8.31 (m, 2H), 8.05 (br.s, 1H), 7.83 (s, 1H), 7.67 (s, 1H), 7.60 (d, J=4.0 Hz, 1H), 7.41-7.39 (m, 3H), 7.35 (s, 2H), 7.27-7.25 (m, 2H), 7.23 (s, 1H), 7.20 (d, J=4.0 Hz, 1H), 4.85-4.81 (m, 2H), 4.63-4.61 (m, 1H), 4.38-4.36 (m, 1H), 4.21-4.19 (m, 1H), 3.71 (s, 3H), 3.68 (s, 3H), 3.58-3.54 (m, 4H), 3.37 (s, 3H), 2.88-2.85 (m, 2H), 2.68-2.65 (m, 1H), 2.41-2.37 (m, 2H), 2.02-1.99 (m, 2H), 1.69-1.67 (m, 2H), 1.44-1.41 (m, 2H), 1.20 (d, J=4.0 Hz, 3H), 1.1 (d, J=4.0, 3H), 0.92 (d, J=4.4 Hz, 6H) ppm.

Example 6

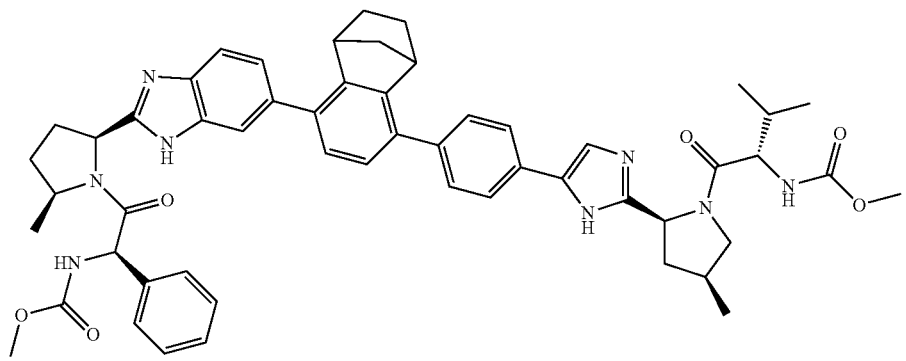

Synthetic Route:

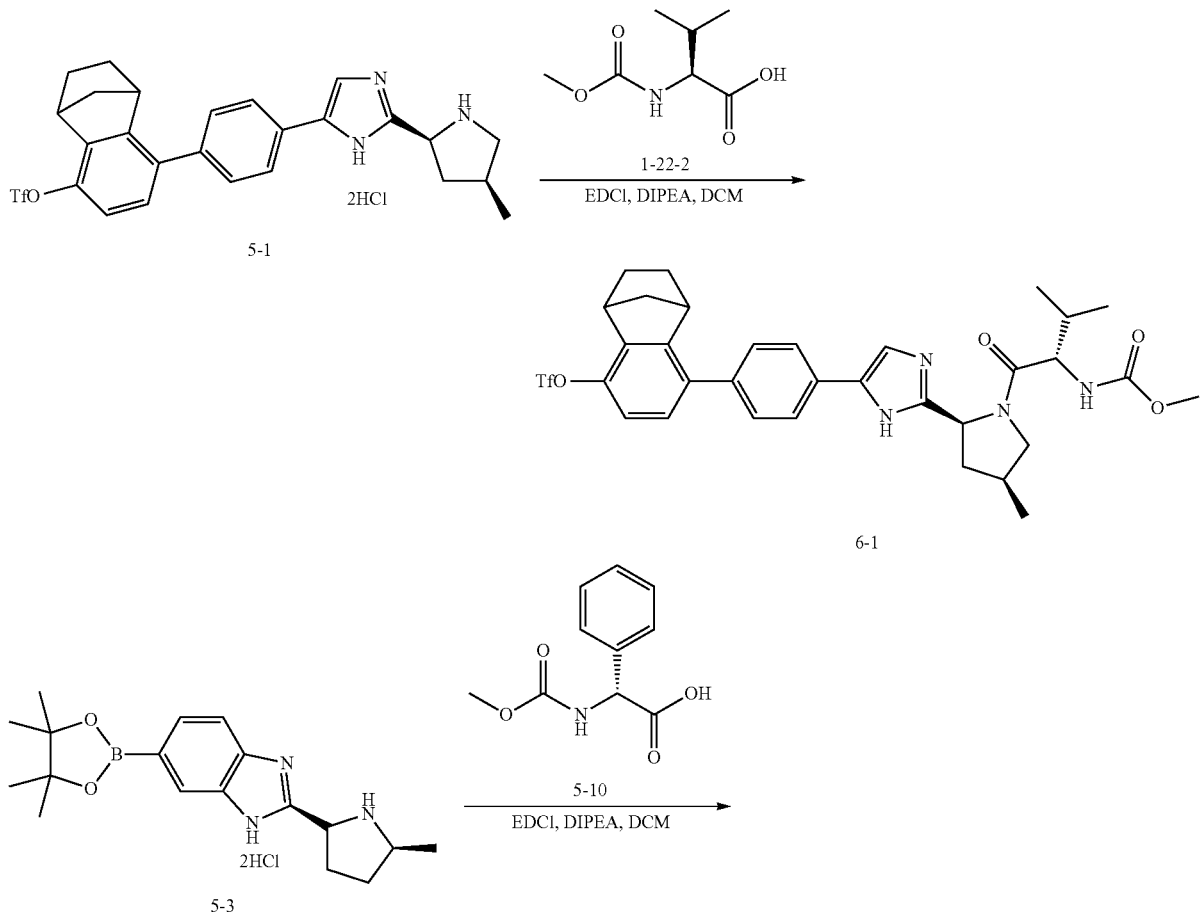

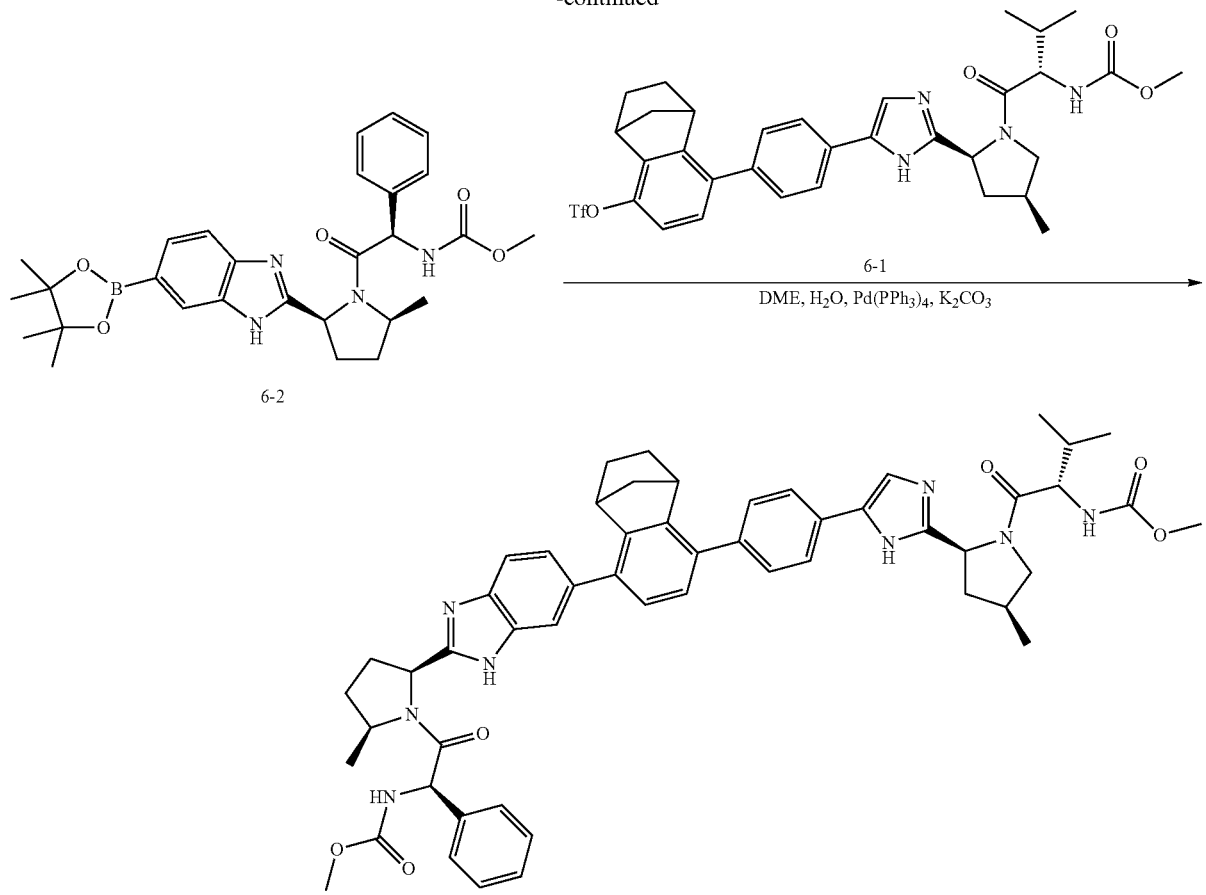

Step 1) the Preparation of Compound 6-1

To a mixture of compound 5-1 (295 mg, 0.5 mmol), compound 1-22-2 (101 mg, 0.58 mmol), EDCI (115 mg, 0.6 mmol) and DCM (10 mL) was added dropwise DIPEA (0.18 mL, 1 mmol) at −15° C. The reaction mixture was stirred at −15° C. for 1.0 hour and then at 25° C. for further 4.0 hours. Then to the reaction was added ammonia (6 mL), and the resulting mixture was stirred for 2.0 hours. The separated organic phase was washed with water (5 mL×2), dried over anhydrous $Na_2SO_4$ and concentrated in vacuo. The residue was purified by silica gel column chromatography (DCM/MeOH (v/v)=50/1) to give the title compound as a white solid (270 mg, 80%). The compound was characterized by the following spectroscopic data:

MS (ESI, pos. ion) m/z: 675.2[M+H]$^+$; and $^1$H NMR (400 MHz, CDCl$_3$): δ 10.53 (br.s, 1H), 7.83 (br.s, 1H), 7.42 (d, J=8.1 Hz, 2H), 7.26 (m, 2H), 7.20 (d, J=8.6 Hz, 1H), 7.02 (d, J=8.6 Hz, 1H), 4.85-4.81 (m, 2H), 4.38-4.36 (m, 1H), 3.71 (s, 3H), 3.58-3.54 (m, 2H), 2.88-2.85 (m, 2H), 2.68-2.65 (m, 1H), 2.41-2.37 (m, 4H), 2.02-1.99 (m, 4H), 1.69-1.67 (m, 3H), 1.20 (d, J=4.0 Hz, 3H), 0.92-0.96 (m, 6H) ppm.

Step 2) the Preparation of Compound 6-2

To a mixture of compound 5-3 (386.3 mg, 0.97 mmol), compound 5-10 (184 mg, 1.05 mmol), EDCI (230 mg, 1.2 mmol) and DCM (10 mL) was added DIPEA (0.35 mL, 2 mmol) dropwise at −15° C. The reaction mixture was stirred at −15° C. for 1.0 hour and then at 25° C. for 4.0 hours. Then to the reaction was added ammonia (6 mL), and the resulting mixture was stirred for 2.0 hours. The separated organic phase was washed with water (5 mL×2), dried over anhydrous $Na_2SO_4$ and concentrated in vacuo. The residue was purified by silica gel column chromatography (DCM/MeOH (v/v)=50/1) to give the title compound as a white solid (200 mg, 40%). The compound was characterized by the following spectroscopic data:

MS (ESI, pos. ion) m/z: 519.3 [M+H]$^+$; and $^1$H NMR (400 MHz, CDCl$_3$): δ 8.01 (br.s, 1H), 7.66 (s, 1H), 7.61 (d, J=4.0 Hz, 1H), 7.20 (d, J=4.0 Hz, 6H), 4.81-4.79 (m, 1H), 4.63-4.61 (m, 1H), 3.68 (s, 3H), 3.53-3.50 (m, 1H), 2.68-2.65 (m, 1H), 2.38-2.35 (m, 2H), 2.02-1.99 (m, 2H), 1.25 (s, 12H), 1.1 (d, J=4.0 Hz, 3H) ppm.

Step 3) the Preparation of Compound 6

A suspension of compound 6-1 (138 mg, 0.2 mmol), compound 6-2 (103 mg, 0.2 mmol), Pd(PPh$_3$)$_4$ (23 mg, 0.02 mmol) and K$_2$CO$_3$ (56 mg, 0.4 mmol) in a mixture solvent of DME (8 mL) and water (2 mL) was stirred at 90° C. under N$_2$. The reaction was monitored by TLC. After the reaction was completed, to the mixture were added DCM (30 mL) and water (20 mL). The separated organic phase was dried over anhydrous Na$_2$SO$_4$ and concentrated in vacuo. The residue was purified by silica gel column chromatography (DCM/MeOH (v/v)=50/1) to give the title compound as a light yellow solid (98 mg, 53%). The compound was characterized by the following spectroscopic data:

MS (ESI, pos. ion) m/z: 917.5[M+H]+; and
1H NMR (400 MHz, CDCl3): δ 8.33-8.31 (m, 2H), 8.05 (br.s, 1H), 7.83 (s, 1H), 7.67 (s, 1H), 7.60 (d, J=4.0 Hz, 1H), 7.41-7.39 (m, 4H), 7.35 (m, 1H), 7.27-7.25 (m, 2H), 7.23 (s, 1H), 7.20 (d, J=4.0 Hz, 1H), 4.85-4.81 (m, 2H), 4.63-4.61 (m, 1H), 4.38-4.36 (m, 1H), 4.21-4.19 (m, 1H), 3.71 (s, 3H), 3.68 (s, 3H), 3.58-3.54 (m, 4H), 3.37 (s, 3H), 2.88-2.85 (m, 2H), 2.68-2.65 (m, 1H), 2.41-2.37 (m, 2H), 2.02-1.99 (m, 2H), 1.69-1.67 (m, 2H), 1.44-1.41 (m, 2H), 1.20 (d, J=4.0 Hz, 3H), 1.1 (d, J=4.0, 3H), 0.92 (d, J=4.4 Hz, 6H) ppm.
Example 7
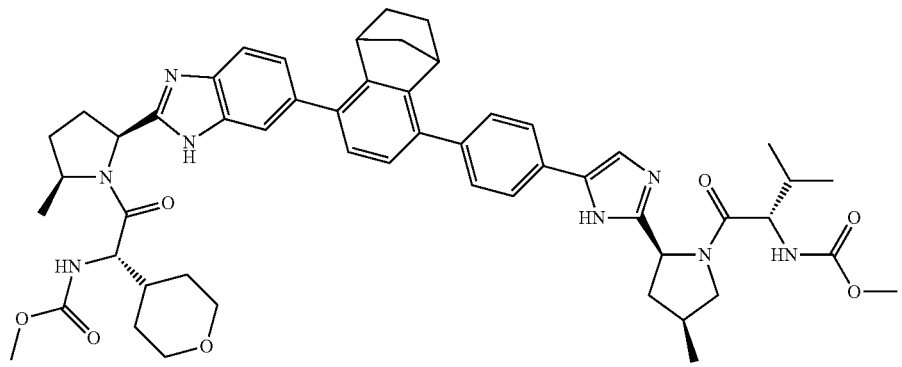
Synthetic Route:
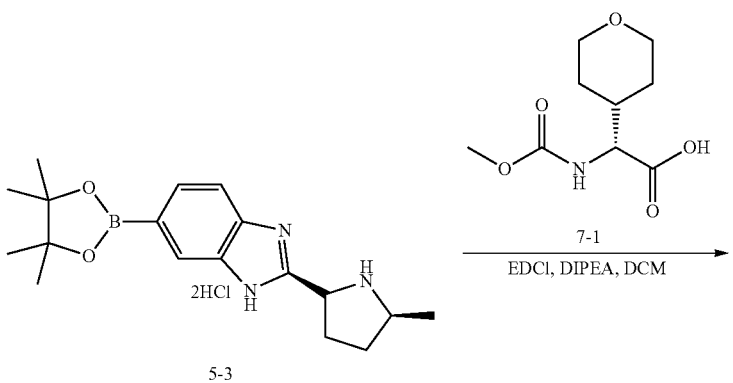
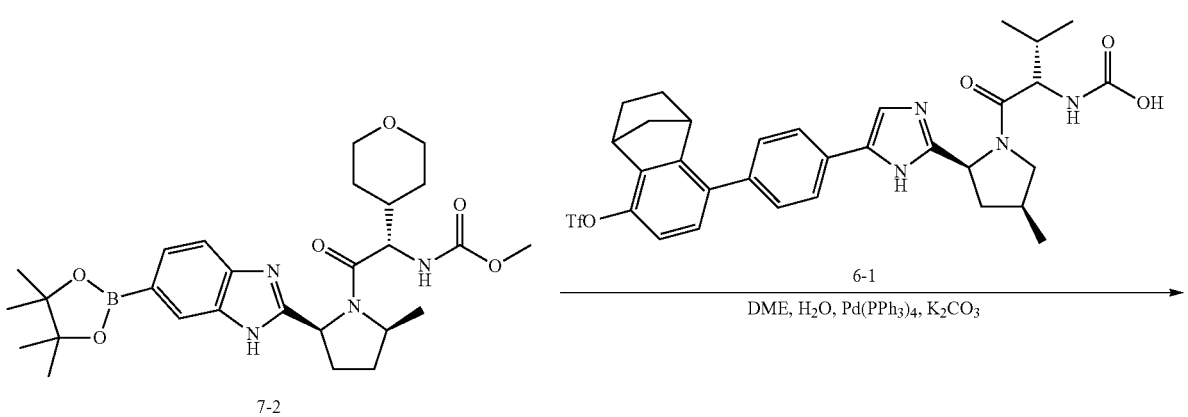

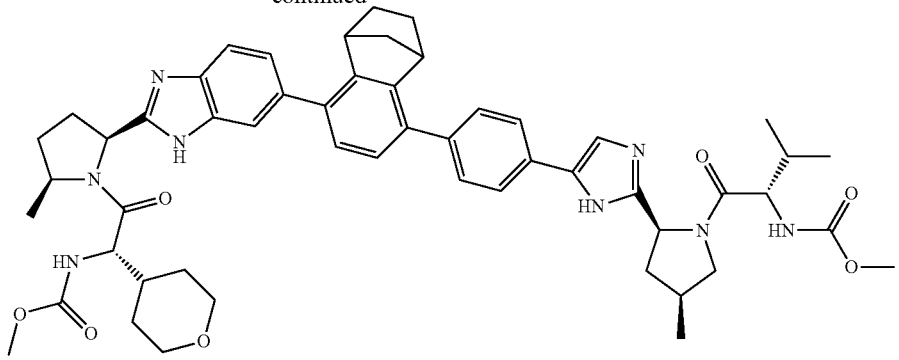

7

Step 1) the Preparation of Compound 7-2

To a mixture of compound 5-3 (400 mg, 1 mmol), compound 7-1 (227 mg, 1.05 mmol) and EDCI (230 mg, 1.2 mmol) and DCM (10 mL) was added DIPEA (0.35 mL, 2 mmol) dropwise at −15° C. The reaction mixture was stirred at −15° C. for 1.0 hour and then at 25° C. for 4.0 hours. Then to the reaction were added ammonia (6 mL), and the resulting mixture was stirred for 2.0 hours. The organic phase was washed with water (5 mL×2), dried over anhydrous Na$_2$SO$_4$ and concentrated in vacuo. The residue was purified by silica gel column chromatography (DCM/MeOH (v/v)=50/1) to give the title compound as a white solid (200 mg, 38%). The compound was characterized by the following spectroscopic data:

MS (ESI, pos. ion) m/z: 527.3 [M+H]$^+$; and $^1$H NMR (400 MHz, CDCl$_3$): δ 8.01 (br.s, 1H), 7.66 (s, 1H), 7.61 (d, J=7.2 Hz, 1H), 4.81-4.79 (m, 1H), 4.63-4.61 (m, 1H), 3.68-3.63 (m, 5H), 3.53-3.50 (m, 4H), 2.68-2.65 (m, 1H), 2.38-2.35 (m, 2H), 2.02-1.69 (m, 4H), 1.32-1.44 (m, 2H), 1.25 (s, 12H), 1.3 (d, J=4.0, 3H) ppm.

Step 2) the Preparation of Compound 7

A suspension of compound 6-1 (132 mg, 0.2 mmol), compound 7-2 (144 mg, 0.2 mmol), Pd(PPh$_3$)$_4$ (23 mg, 0.02 mmol) and K$_2$CO$_3$ (56 mg, 0.4 mmol) in a mixture solvent of DME (8 mL) and water (2 mL) was stirred at 90° C. under N$_2$ for 3.0 hours. After the reaction was completed, to the mixture were added DCM (30 mL) and water (20 mL). The separated organic phase was dried over anhydrous Na$_2$SO$_4$ and concentrated in vacuo. The residue was purified by silica gel column chromatography (DCM/MeOH (v/v)=50/1) to give the title compound as a light yellow solid (98 mg, 53%). The compound was characterized by the following spectroscopic data:

MS (ESI, pos. ion) m/z: 925.5[M+H]$^+$; and $^1$H NMR (400 MHz, CDCl$_3$): δ 10.65 (br.s, 1H), 8.03-7.61 (m, 2H), 7.56-7.42 (m, 3H), 7.41-7.30 (m, 2H), 7.25-7.14 (m, 3H), 4.81-4.79 (m, 2H), 4.63-4.61 (m, 2H), 3.88-3.84 (m, 5H), 3.73 (s, 3H), 3.71 (s, 3H), 3.56-3.32 (m, 2H), 3.30 (m, 2H), 2.51-2.32 (m, 4H), 2.32-2.18 (m, 4H), 2.15-1.94 (m, 2H), 1.82-1.62 (m, 5H), 1.58-1.36 (m, 4H), 1.13-1.02 (m, 3H), 0.97-0.71 (m, 9H) ppm.

Example 8

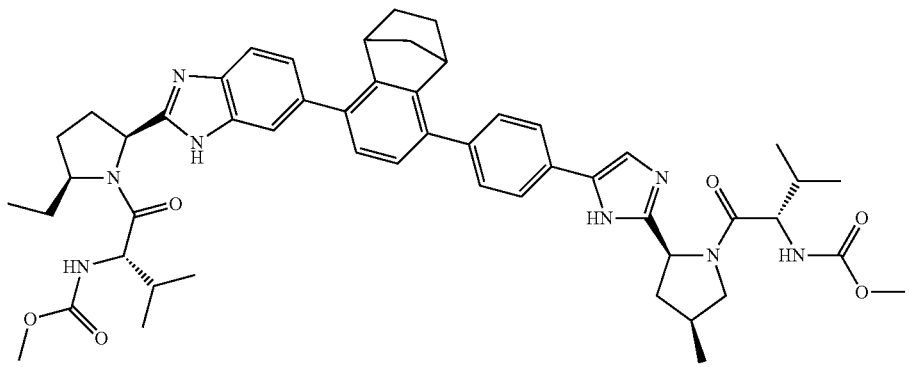 [SMILES: CC[C@H]1CC[C@@H](c2nc3ccc(-c4ccc(-c5ccc(-c6cnc([C@@H]7C[C@H](C)CN7C(=O)[C@@H](NC(=O)OC)C(C)C)[nH]6)cc5)c5c4C4CCC5C4)cc3[nH]2)N1C(=O)[C@@H](NC(=O)OC)C(C)C]

Synthetic Route:

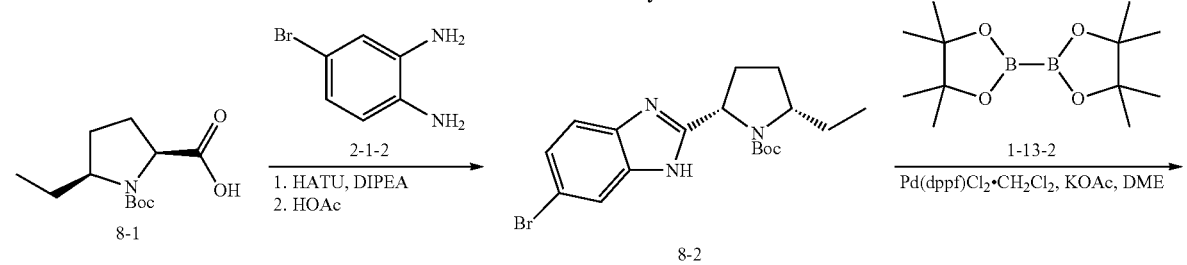

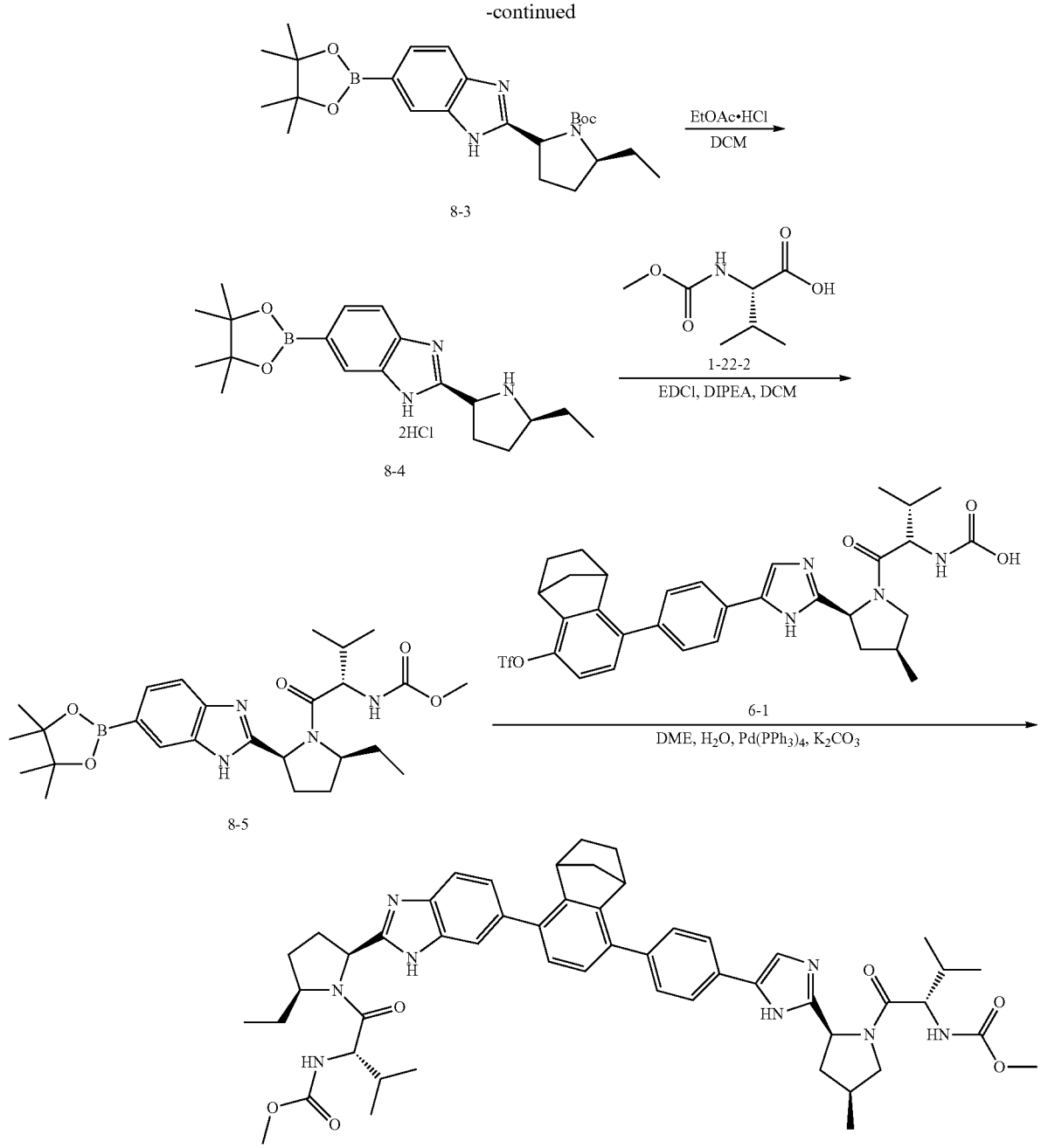

Step 1) the Preparation of Compound 8-2

To a solution of compound 8-1 (2.11 g, 8.7 mmol) and HATU (3.5 g, 9.2 mmol) in THF (30 mL) was added DIPEA (6 mL, 34 mmol) dropwise at 0° C. The reaction mixture was stirred at 0° C. for 0.5 hour. Then to the mixture was added a solution of compound 2-1-2 (1.8 g, 9.6 mmol) in THF (15 mL). After the addition, the reaction was stirred at 25° C. for 2.0 hours, and then to the mixture was added water (10 mL). The THF was removed. The residue was added water (10 mL), and the resulting mixture was extracted with EtOAc (50 mL×3). The combined organic phases were washed with saturated brine (100 mL), dried over anhydrous Na$_2$SO$_4$ and concentrated in vacuo. The residue was dissolved with acetic acid (35 mL). The resulting mixture was stirred at 40° C. for 12 hours, neutralized with saturated aqueous sodium hydrogen carbonated solution, and extracted with EtOAc (50 mL×3). The combined organic phases were washed with saturated brine (100 mL), dried over anhydrous Na$_2$SO$_4$ and concentrated in vacuo, and the residue was purified by silica gel column chromatography (n-hexane/EtOAc (v/v)=4/1) to give the title compound as a reddish brown solid (2.4 g, 70%). The compound was characterized by the following spectroscopic data:

$^1$H NMR (400 MHz, CDCl$_3$): δ 7.87 (s, 1H), 7.42-7.40 (m, 1H), 7.30-7.28 (m, 1H), 5.11-5.09 (m, 1H), 3.45-3.43 (m, 2H), 2.94-2.93 (m, 1H), 2.21-2.18 (m, 1H), 2.01-1.91 (m, 1H), 1.62-1.52 (m, 2H), 1.49 (s, 9H), 0.91 (m, 3H) ppm.

Step 2) the Preparation of Compound 8-3

To a mixture of compound 8-2 (2.5 g, 6.3 mmol), 4,4,4', 4',5,5,5',5'-octamethyl-2,2'-bi(1,3,2-dioxaborolane) (1.8 g, 7.0 mmol), Pd(dppf)Cl$_2$·CH$_2$Cl$_2$ (100 mg, 0.12 mmol) and KOAc (1.6 g, 16 mmol) was added DME (30 mL) under N$_2$. The reaction was stirred at 90° C. under N$_2$ for 3.0 hours. After the reaction was completed, the reaction was cooled to rt, and concentrated in vacuo. To the mixture was added water (30 mL). The resulting mixture was extracted with EtOAc (50 mL×3). The combined organic phases were washed with brine (50 mL×2), dried over anhydrous Na$_2$SO$_4$ and concentrated in vacuo. The residue was purified by silica gel column chromatography (PE/EtOAc (v/v)=4/1) to give the title compound (2.1 g, 76%). The compound was characterized by the following spectroscopic data:

$^1$H NMR (400 MHz, CDCl$_3$): δ 7.87 (s, 1H), 7.42-7.40 (m, 1H), 7.30-7.28 (m, 1H), 5.11-5.09 (m, 1H), 3.45-3.43 (m, 2H), 2.94-2.93 (m, 1H), 2.21-2.18 (m, 1H), 2.01-1.91 (m, 1H), 1.62-1.52 (m, 2H), 1.49 (s, 9H), 1.25 (s, 12H) 0.91 (d, 3H) ppm.

Step 3) the Preparation of Compound 8-4

To a solution of compound 8-3 (2.2 g, 5.08 mmol) in DCM (20 mL) was added a solution of HCl in EtOAc (8 mL, 4 mol/L) dropwise at 25° C. The reaction was stirred at 25° C. for 3.0 hours. After the reaction was completed, the reaction mixture was filtrated, and the filter cake was washed with EtOAc (5 mL) to give the title compound as a white solid (1.64 g, 78%). The compound was characterized by the following spectroscopic data:

MS (ESI, pos. ion) m/z: 342.3 [M+H]$^+$.

Step 4) the Preparation of Compound 8-5

To a mixture of compound 8-4 (413.3 mg, 1 mmol), compound 1-22-2 (184 mg, 1.05 mmol) and EDCI (230 mg, 1.2 mmol) and DCM (10 mL) was added dropwise DIPEA (0.35 mL, 2 mmol) at −15° C. The reaction mixture was stirred at −15° C. for 1.0 hour and then at 25° C. for 4.0 hours. Then to the reaction was added ammonia (6 mL), and the resulting mixture was stirred for 2.0 hours. The organic phase was washed with water (5 mL×2), dried over anhydrous Na$_2$SO$_4$ and concentrated in vacuo. The residue was purified by silica gel column chromatography (DCM/MeOH (v/v)=50/1) to give the title compound as a white solid (200 mg, 40.1%). The compound was characterized by the following spectroscopic data:

MS (ESI, pos. ion) m/z: 499.3[M+H]$^+$; and $^1$H NMR (400 MHz, CDCl$_3$): δ 8.01 (br.s, 1H), 7.66 (s, 1H), 7.61 (d, J=4.0 Hz, 1H), 4.81-4.79 (m, 1H), 4.63-4.61 (m, 1H), 3.68 (s, 3H), 3.53-3.50 (m, 2H), 2.68-2.65 (m, 1H), 2.38-2.35 (m, 1H), 2.02-1.99 (m, 2H), 1.61 (m, 2H), 1.25 (s, 12H), 0.93 (m, 9H) ppm.

Step 5) the Preparation of Compound 8

A suspension of compound 6-1 (132 mg, 0.2 mmol), compound 8-5 (99.6 mg, 0.2 mmol), Pd(PPh$_3$)$_4$ (23 mg, 0.02 mmol) and K$_2$CO$_3$ (56 mg, 0.4 mmol) in a mixture solvent of DME (8 mL) and water (2 mL) was stirred at 90° C. under N$_2$ for 3.5 hours. After the reaction was completed, to the mixture were added DCM (30 mL) and water (20 mL). The separated organic phase was dried over anhydrous Na$_2$SO$_4$ and concentrated in vacuo. The residue was purified by silica gel column chromatography (DCM/MeOH (v/v)=50/1) to give the title compound as a light yellow solid (98 mg, 55%). The compound was characterized by the following spectroscopic data:

MS (ESI, pos. ion) m/z: 897.5[M+H]$^+$; and $^1$H NMR (400 MHz, CDCl$_3$): δ 8.33-8.31 (m, 2H), 8.05 (br.s, 1H), 7.83 (s, 1H), 7.67 (s, 1H), 7.60 (d, J=4.0 Hz, 1H), 7.41-7.39 (m, 2H), 7.35 (s, 1H), 7.23 (s, 1H), 4.85-4.81 (m, 2H), 4.38-4.36 (m, 1H), 4.21-4.19 (m, 1H), 3.71 (s, 3H), 3.68 (s, 3H), 3.58-3.54 (m, 4H), 3.37 (s, 3H), 2.88-2.85 (m, 2H), 2.68-2.65 (m, 1H), 2.41-2.37 (m, 4H), 2.02-1.99 (m, 4H), 1.69-1.67 (m, 3H), 1.61 (m, 2H), 1.50 (m, 3H), 1.1 (d, J=4.0 Hz, 3H), 0.95 (d, J=4.4 Hz, 6H), 0.93 (m, 9H) ppm.

Example 9

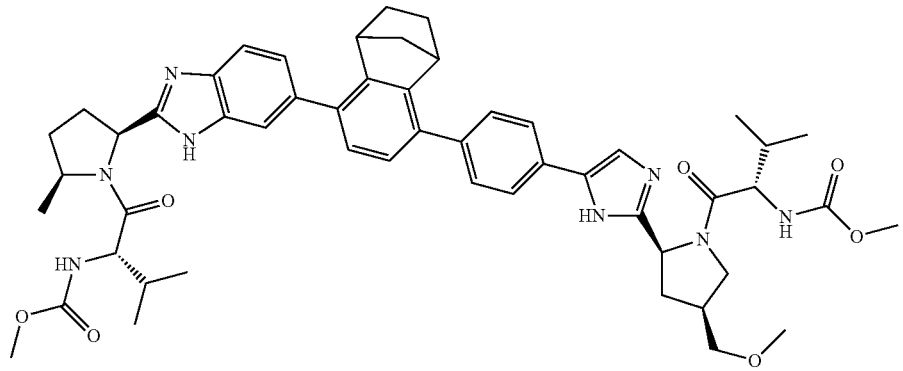

Synthetic Route:

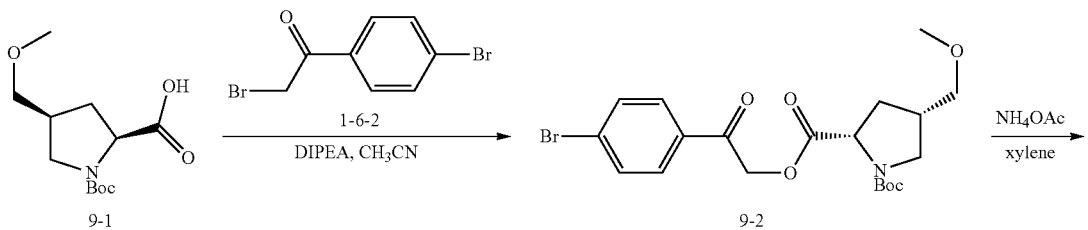

-continued
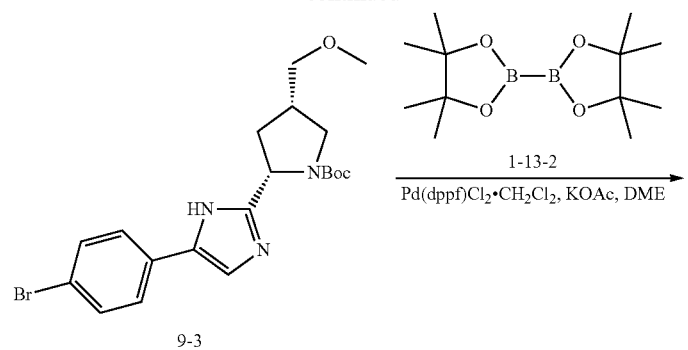
9-3
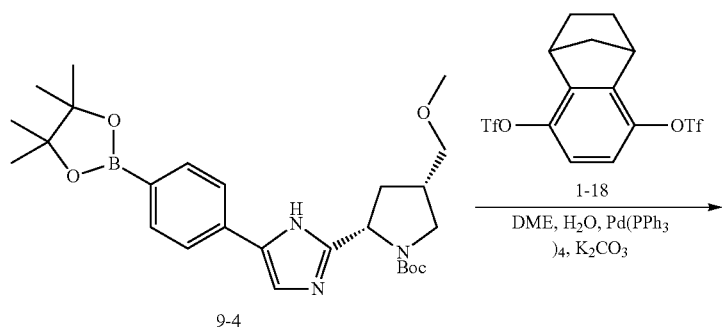
9-4
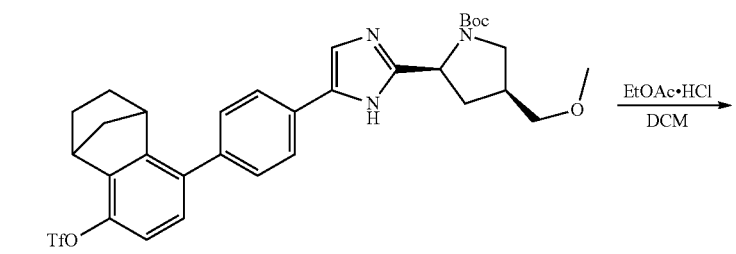
9-5
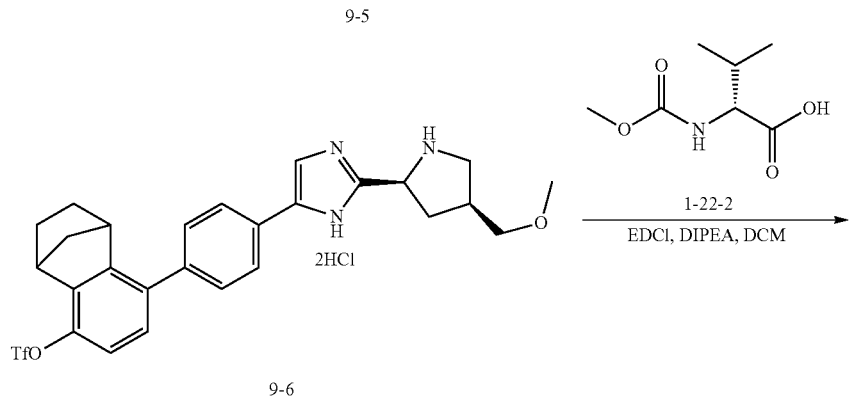
9-6
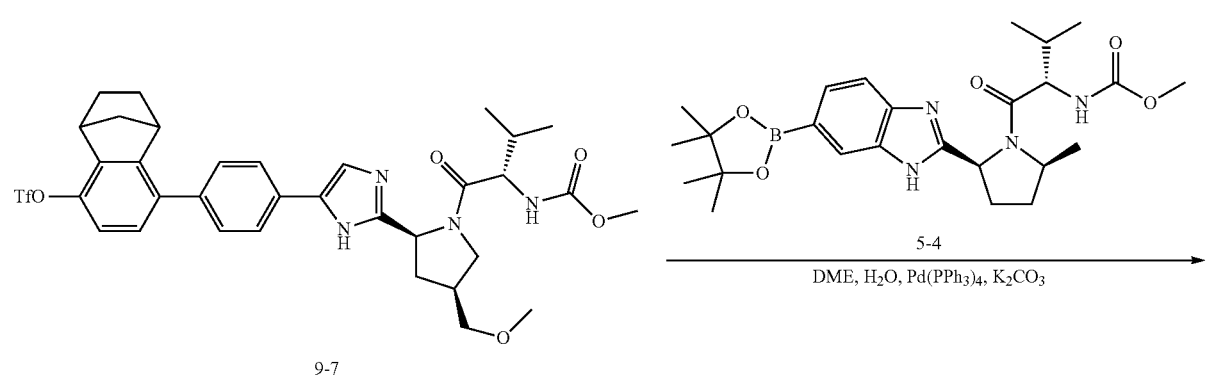
9-7

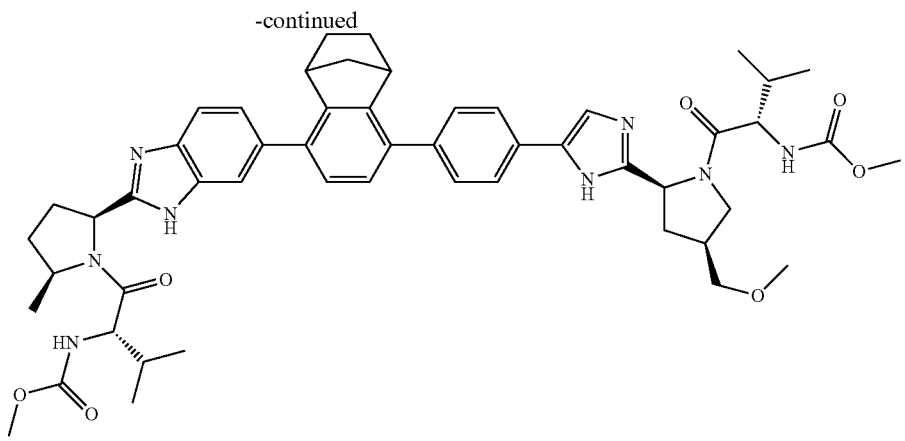

9

Step 1) the Preparation of Compound 9-2

To a solution of compound 9-1 (1.7 g, 6.55 mmol) and compound 1-6-2 (2.0 g, 7.2 mmol) in acetonitrile (50 mL) was added DIPEA (1.3 mL, 7.36 mmol) at 0° C. The reaction was stirred at 25° C. The reaction was monitored by TLC, after the reaction was completed, to the mixture was added water (10 mL). The resulting mixture was extracted with EtOAc (30 mL×3). The combined organic phases were dried over anhydrous $Na_2SO_4$ and concentrated in vacuo. The residue was purified by silica gel column chromatography (PE/EtOAc (v/v)=4/1) to give the title compound as a white solid (2.55 g g, 85%). The compound was characterized by the following spectroscopic data:

MS (ESI, pos.ion) m/z: 456.1 [M+H]$^+$; and $^1$H NMR (400 MHz, CDCl$_3$): δ 7.78 (m, 2H), 7.65 (m, 2H), 5.54-5.15 (m, 2H), 4.43 (dt, J=15.2, 8.0 Hz, 1H), 3.82-3.66 (m, 1H), 3.46-3.34 (m, 5H), 3.23 (dd, J=10.7, 7.7 Hz, 1H), 2.25-2.12 (m, 2H), 1.84 (m, 1H), 1.43 (s, 9H) ppm.

Step 2) the Preparation of Compound 9-3

To xylene (30 mL) was added a mixture of compound 9-2 (2.82 g, 6.2 mmol) and ammonium acetate (4.6 g, 59.7 mmol). The reaction mixture was stirred at 130° C. for 5 hours. The mixture was cooled to rt and to the mixture was added H$_2$O (30 mL). The resulting mixture was extracted with EtOAc (40 mL×3). The combined organic phases were dried over anhydrous $Na_2SO_4$ and concentrated in vacuo. The residue was purified by silica gel column chromatography (PE/EtOAc (v/v)=4/1) to give the title compound as a whited solid (1.63 g, 60.3%). The compound was characterized by the following spectroscopic data:

MS (ESI, pos.ion) m/z: 436.1 [M+H]$^+$; and $^1$H NMR (400 MHz, CDCl$_3$): δ 7.55 (br., 2H), 7.46-7.48 (m, 2H), 7.22 (s, 1H), 4.93-4.96 (m, 1H), 3.95-3.97 (m, 1H), 3.46-3.34 (m, 5H), 3.23 (dd, J=10.7, 7.7 Hz, 1H), 2.25-2.12 (m, 2H), 1.84 (m, 1H), 1.43 (s, 9H) ppm.

Step 3) the Preparation of Compound 9-4

To a mixture of compound 9-3 (1.63 g, 4.0 mmol), 4,4,4',4',5,5,5',5'-octamethyl-2,2'-bi(1,3,2-dioxaborolane) (1.12 g, 4.4 mmol), Pd(dppf)Cl$_2$.CH$_2$Cl$_2$ (71 mg, 0.09 mmol) and KOAc (0.98 g, 10 mmol) was added DME (20 mL) under N$_2$. The reaction mixture was stirred at 90° C. for 5.0 hours. After the reaction was completed, the reaction was cooled to rt and removed DME. Then to the residue was added water (20 mL). The resulting mixture was extracted with EtOAc (30 mL×3). The combined organic phases were washed with brine (50 mL), dried over anhydrous $Na_2SO_4$ and concentrated in vacuo. The residue was purified by silica gel column chromatography (PE/EtOAc (v/v)=2/1) to give the title compound as a light yellow solid (1.77 g, 97.6%). The compound was characterized by the following spectroscopic data:

MS (ESI, pos.ion) m/z: 484.3 [M+H]$^+$; and $^1$H NMR (400 MHz, CDCl$_3$): δ 7.78 (m, 2H), 7.65 (m, 2H), 7.35 (s, 1H), 4.43 (dt, J=15.2, 8.0 Hz, 1H), 3.82-3.66 (m, 1H), 3.46-3.34 (m, 5H), 3.23 (dd, J=10.7, 7.7 Hz, 1H), 2.25-2.12 (m, 2H), 1.84 (m, 1H), 1.43 (s, 9H), 1.25 (s, 12H) ppm.

Step 4) the Preparation of Compound 9-5

A suspension of compound 1-18 (8.30 g, 18.8 mmol), compound 9-4 (9.27 g, 19.2 mmol), Pd(PPh$_3$)$_4$ (1.10 g, 0.94 mmol) and K$_2$CO$_3$ (10.4 g, 75.4 mmol) in a mixture solvent of DME and water (v/v=3/1, 80 mL) was stirred at 90° C. under N$_2$ for 3.0 hours. After the reaction was completed, to the mixture was added EtOAc (50 mL), and the resulting mixture was washed saturated brine (50 mL). The separated organic phase was dried over anhydrous Na$_2$SO$_4$ and concentrated in vacuo. The residue was purified by recrystal with ethyl alcohol to give the title compound as a white solid (5.50 g, 44.3%). The compound was characterized by the following spectroscopic data:

MS (ESI, pos.ion) m/z: 604.3 [M+H]$^+$; and $^1$H NMR (400 MHz, CDCl$_3$): δ 10.53 (br.s, 1H), 7.83 (br.s, 1H), 7.42 (d, J=8.1 Hz, 2H), 7.26 (m, 2H), 7.20 (d, J=8.6 Hz, 1H), 7.02 (d, J=8.6 Hz, 1H), 4.98 (d, J=5.2 Hz, 1H), 3.70 (s, 3H), 3.48-3.35 (m, 4H), 2.88-2.84 (m, 2H), 2.25-2.10 (m, 2H), 2.04-1.96 (m, 3H), 1.82-1.80 (m, 3H), 1.59-1.56 (m, 1H), 1.51 (s, 9H) ppm.

Step 5) the Preparation of Compound 9-6

To a solution of compound 9-5 (2.12 g, 3.27 mmol) in DCM (30 mL) was added a solution of HCl in EtOAc (12 mL, 4 mol/L) dropwise at 25° C. The reaction was stirred at 25° C. for 5.5 hours. After the reaction was completed, the reaction mixture was concentrated in vacuo, and residue was washed with EtOAc (30 mL) to give the title compound as a hoary solid (1.4 g, 69.2%). The compound was characterized by the following spectroscopic data:

MS (ESI, pos. ion) m/z: 548.2[M+H]$^+$.

Step 6) the Preparation of Compound 9-7

To a mixture of compound 9-6 (310 mg, 0.5 mmol), compound 1-22-2 (92 mg, 0.53 mmol), EDCI (115 mg, 0.6 mmol) and DCM (10 mL) was added DIPEA (0.18 mL, 1 mmol) dropwise at −15° C. The reaction mixture was stirred at −15° C. for 1.0 hour and then at 25° C. for 4.0 hours. Then to the reaction was added ammonia (6 mL), and the resulting mixture was stirred for 2.0 hours. The organic phase was washed with water (5 mL×2), dried over anhydrous $Na_2SO_4$ and concentrated in vacuo. The residue was purified by silica gel column chromatography (DCM/MeOH (v/v)=50/1) to give the title compound as a white solid (270 mg, 78%). The compound was characterized by the following spectroscopic data:

MS (ESI, pos. ion) m/z: 705.7 $[M+H]^+$; and $^1$H NMR (400 MHz, $CDCl_3$): δ 8.32-8.29 (m, 1H), 7.81 (s, 1H), 7.41-7.39 (m, 2H), 7.35 (s, 1H), 7.27-7.25 (m, 2H), 4.85-4.82 (m, 1H), 4.38-4.35 (m, 1H), 4.21-4.18 (m, 1H), 3.70 (s, 3H), 3.46-3.34 (m, 5H), 3.59-3.56 (m, 2H), 2.88-2.84 (m, 2H), 2.42-2.38 (m, 2H), 2.02-2.00 (m, 1H), 1.70-1.67 (m, 3H), 1.45-1.41 (m, 3H), 1.1 (d, J=4.3 Hz, 6H) ppm.

Step 7) the Preparation of Compound 9

A suspension of compound 9-7 (141 mg, 0.2 mmol), compound 5-4 (97 mg, 0.2 mmol), $Pd(PPh_3)_4$ (23 mg, 0.02 mmol) and $K_2CO_3$ (56 mg, 0.4 mmol) in a mixture solvent of DME (8 mL) and water (2 mL) was stirred at 90° C. under $N_2$. The reaction was monitored by TLC, after the reaction was completed, to the mixture were added DCM (30 mL) and water (20 mL). The separated organic phase was dried over anhydrous $Na_2SO_4$ and concentrated in vacuo. The residue was purified by silica gel column chromatography (DCM/MeOH (v/v)=50/1) to give the title compound as a light yellow solid (98 mg, 53%). The compound was characterized by the following spectroscopic data:

MS (ESI, pos. ion) m/z: 913.5$[M+H]^+$; and $^1$H NMR (400 MHz, $CDCl_3$): δ 8.33-8.31 (m, 2H), 8.05 (br.s, 1H), 7.83 (s, 1H), 7.60 (d, J=4.0 Hz, 1H), 7.35 (s, 1H), 7.27-7.25 (m, 2H), 7.23 (s, 1H), 7.20 (d, J=4.0 Hz, 1H), 4.85-4.81 (m, 2H), 4.38-4.36 (m, 1H), 4.21-4.19 (m, 1H), 3.71 (s, 3H), 3.68 (s, 3H), 3.58-3.54 (m, 4H), 3.37 (s, 3H), 2.88-2.85 (m, 2H), 2.68-2.65 (m, 1H), 2.41-2.37 (m, 4H), 2.02-1.99 (m, 4H), 1.69-1.67 (m, 4H), 1.20 (d, J=4.0 Hz, 3H), 0.92 (d, J=4.4 Hz, 12H) ppm.

Example 10

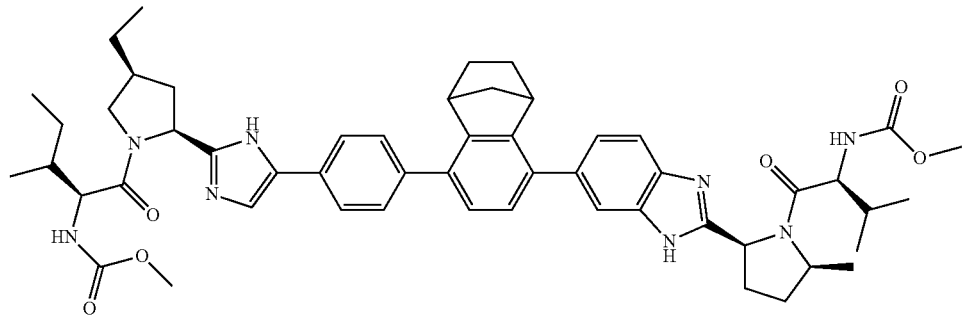 [SMILES: CCC(C)[C@H](NC(=O)OC)C(=O)N1C[C@@H](CC)C[C@H]1c1ncc(-c2ccc(-c3ccc(-c4ccc5nc([C@@H]6CC[C@H](C)N6C(=O)[C@@H](NC(=O)OC)C(C)C)[nH]c5c4)c4c3C3CCC4C3)cc2)[nH]1]

Synthetic Route:

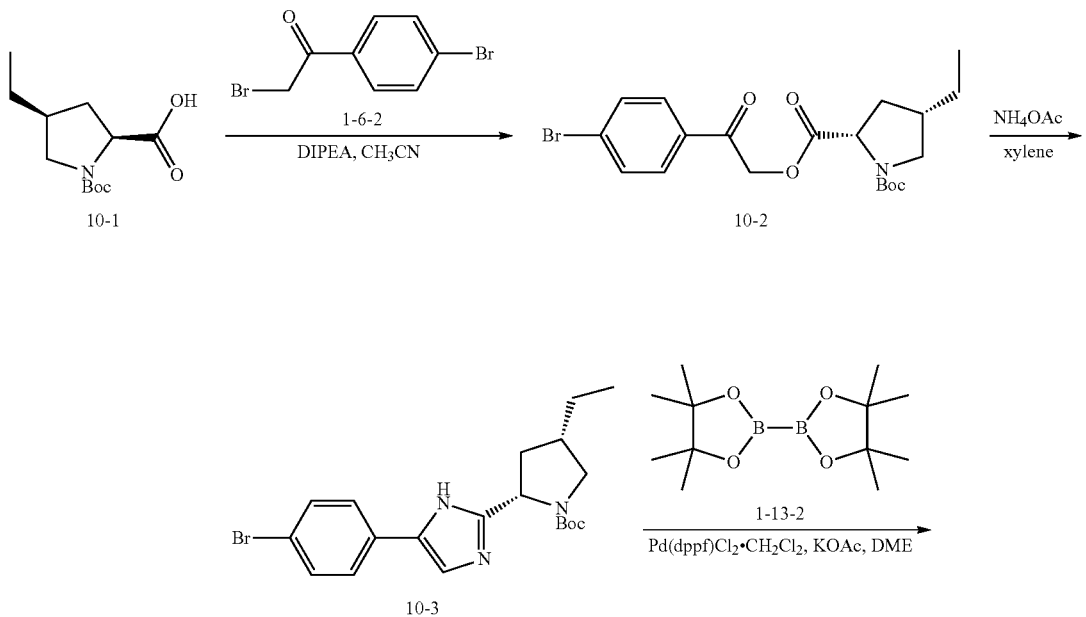

-continued
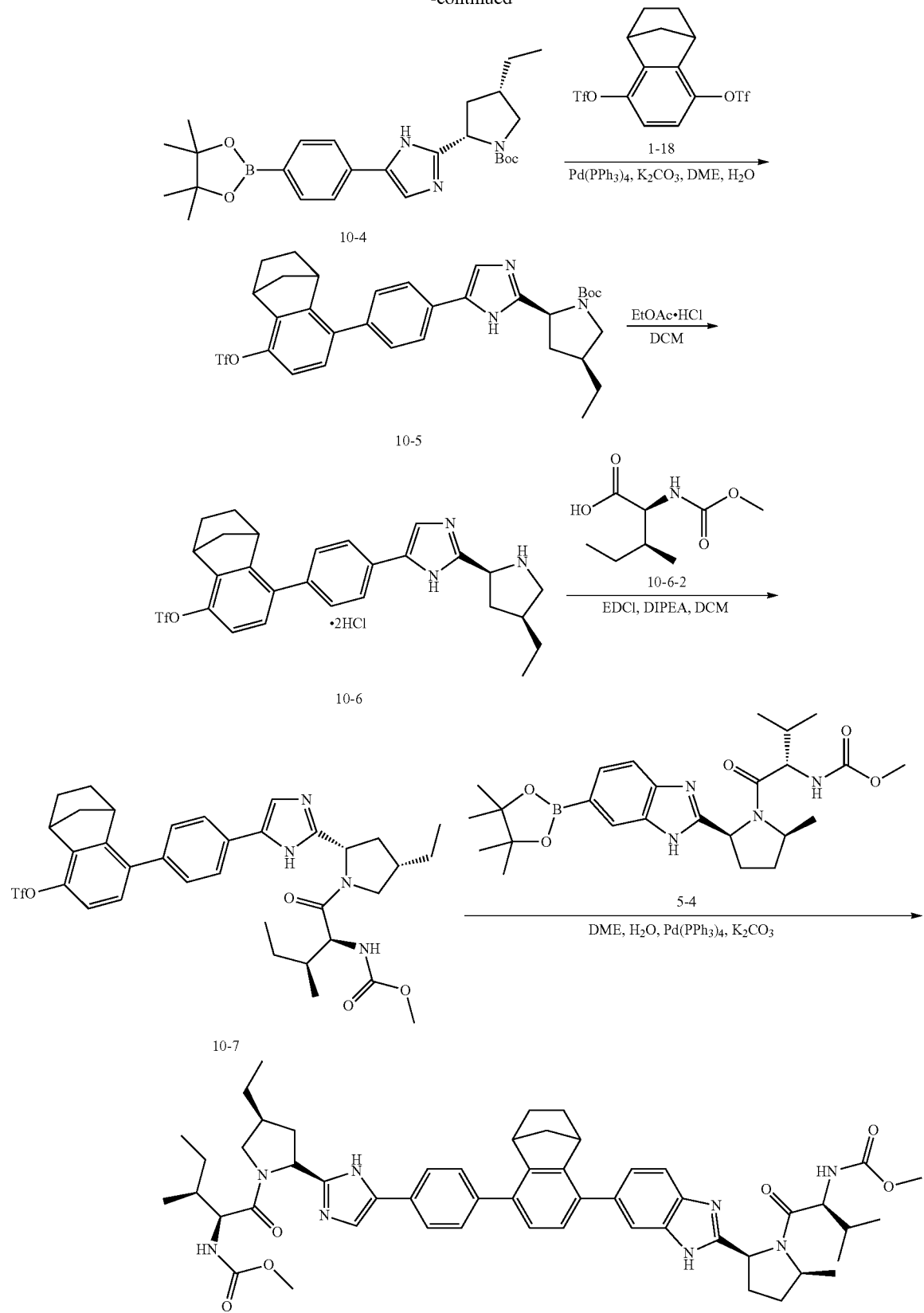

Step 1) the Preparation of Compound 10-2

The title compound was prepared by the procedure described in step 1 of Example 9 using DIPEA (1.3 mL, 7.36 mmol), compound 10-1 (1.59 g, 6.55 mmol), compound 1-6-2 (2.0 g, 7.2 mmol) and acetonitrile (50 mL) to give the title compound as a white solid (2.65 g, 92%). The compound was characterized by the following spectroscopic data:

MS (ESI, pos.ion) m/z: 440 [M+H]$^+$; and
$^1$H NMR (400 MHz, CDCl$_3$): δ 7.78 (m, 2H), 7.65 (m, 2H), 5.54-5.15 (m, 2H), 4.39 (m, 1H), 3.76 (m, 1H), 3.03 (m, 1H), 2.53 (m, 1H), 2.27 (m, 1H), 1.84 (m, 1H), 1.62 (m, 2H), 1.43 (m, 9H), 1.09 (m, 3H) ppm.

Step 2) the Preparation of Compound 10-3

The title compound was prepared by the procedure described in step 2 of Example 9 using compound 10-2 (2.65 g, 6.0 mmol), ammonium acetate (4.6 g, 60 mmol) and xylene (30 mL) to give the title compound as white solid (1.56 g, 62%). The compound was characterized by the following spectroscopic data:

MS (ESI, pos.ion) m/z: 420 [M+H]$^+$; and
$^1$H NMR (400 MHz, CDCl$_3$): δ 7.78 (m, 2H), 7.65 (m, 2H), 7.35 (s, 1H), 4.39 (m, 1H), 3.76 (m, 1H), 3.03 (m, 1H), 2.53 (m, 1H), 2.27 (m, 1H), 1.84 (m, 1H), 1.63 (m, 2H), 1.43 (m, 9H), 1.09 (m, 3H) ppm.

Step 3) the Preparation of Compound 10-4

The title compound was prepared by the procedure described in step 3 of Example 9 using DME (20 mL), compound 10-3 (1.56 g, 3.7 mmol), 4,4,4',4',5,5,5',5'-octamethyl-2,2'-bi(1,3,2-dioxaborolane) (1.04 g, 4.1 mmol), Pd(dppf)Cl$_2$.CH$_2$Cl$_2$ (73 mg, 0.09 mmol) and KOAc (0.73 g, 7.4 mmol) to give the title compound as a light yellow solid (1.65 g, 95%). The compound was characterized by the following spectroscopic data:

MS (ESI, pos.ion) m/z: 468.4 [M+H]$^+$; and
$^1$H NMR (400 MHz, CDCl$_3$): δ 7.78 (m, 2H), 7.65 (m, 2H), 7.35 (s, 1H), 4.39 (m, 1H), 3.76 (m, 1H), 3.03 (m, 1H), 2.53 (m, 1H), 2.27 (m, 1H), 1.84 (m, 1H), 1.63 (m, 2H), 1.43 (m, 9H), 1.09 (m, 15H) ppm.

Step 4) the Preparation of Compound 10-5

The title compound was prepared by the procedure described in step 4 of Example 9 using compound 1-18 (8.20 g, 18.6 mmol), compound 10-4 (8.88 g, 19.0 mmol), Pd(PPh$_3$)$_4$ (1.07 g, 0.93 mmol), K$_2$CO$_3$ (10.28 g, 74.4 mmol) and a mixture solvent of DME and water (v/v=3/1, 80 mL) to give the title compound as a white solid (6.12 g, 52.1%). The compound was characterized by the following spectroscopic data:

MS (ESI, pos.ion) m/z: 632.7 [M+H]$^+$; and
$^1$H NMR (400 MHz, CDCl$_3$): δ 10.53 (br.s, 1H), 7.83 (br.s, 1H), 7.42 (d, J=8.1 Hz, 2H), 7.26 (m, 2H), 7.20 (d, J=8.6 Hz, 1H), 7.02 (d, J=8.6 Hz, 1H), 4.98 (d, J=5.2 Hz, 1H), 3.70-3.50 (m, 2H), 3.48-3.35 (m, 2H), 2.25-2.10 (m, 2H), 2.04-1.96 (m, 3H), 1.82-1.80 (m, 1H), 1.59-1.56 (m, 2H), 1.51 (s, 9H), 1.43-1.39 (m, 3H), 0.96 (m, 3H, J=4.8 Hz) ppm.

Step 5) the Preparation of Compound 10-6

The title compound was prepared by the procedure described in step 5 of Example 9 using a solution of HCl in EtOAc (24 mL, 4 mol/L), compound 10-5 (6.12 g, 9.69 mmol) and DCM (60 mL) to give the title compound as a offwhite solid (4.69 g, 80%). The compound was characterized by the following spectroscopic data:

MS (ESI, pos. ion) m/z: 532.6 [M+H]$^+$.

Step 6) the Preparation of Compound 10-7

The title compound was prepared by the procedure described in step 6 of Example 9 using DIPEA (0.18 mL, 1 mmol), compound 10-6 (302 mg, 0.5 mmol), compound 10-6-2 (100 mg, 0.53 mmol), EDCI (115 mg, 0.6 mmol) and DCM (10 mL) to give the title compound as a white solid (283 mg, 81%). The compound was characterized by the following spectroscopic data:

MS (ESI, pos. ion) m/z: 703.8 [M+H]$^+$; and
$^1$H NMR (400 MHz, CDCl$_3$): δ 10.53 (br.s, 1H), 7.83 (br.s, 1H), 7.42 (d, J=8.1 Hz, 2H), 7.26 (m, 2H), 7.20 (d, J=8.6 Hz, 1H), 7.02 (d, J=8.6 Hz, 1H), 4.85-4.81 (m, 1H), 4.38-4.36 (m, 1H), 3.71 (s, 3H), 3.58-3.54 (m, 2H), 2.88-2.85 (m, 2H), 2.68-2.65 (m, 1H), 2.41-2.37 (m, 2H), 2.02-1.99 (m, 2H), 1.69-1.67 (m, 2H), 1.58-1.55 (m, 4H), 1.44-1.41 (m, 3H), 1.20 (d, J=4.0 Hz, 3H), 0.92-0.96 (m, 6H) ppm.

Step 7) the Preparation of Compound 10

The title compound was prepared by the procedure described in step 7 of Example 9 using compound 10-7 (140 mg, 0.2 mmol), compound 5-4 (97 mg, 0.2 mmol), Pd(PPh$_3$)$_4$ (23 mg, 0.02 mmol), K$_2$CO$_3$ (56 mg, 0.4 mmol) and a mixture solvent of DME (8 mL) and water (2 mL) to give the title compound as a light yellow solid (111 mg, 61%). The compound was characterized by the following spectroscopic data:

MS (ESI, pos. ion) m/z: 911.4 [M+H]$^+$; and
$^1$H NMR (400 MHz, CDCl$_3$): δ 8.33-8.31 (m, 2H), 8.05 (br.s, 1H), 7.83 (s, 1H), 7.67 (s, 1H), 7.60 (d, J=4.0 Hz, 1H), 7.41-7.39 (m, 2H), 7.35 (s, 1H), 7.23 (s, 1H), 4.85-4.81 (m, 2H), 4.63-4.61 (m, 1H), 4.38-4.36 (m, 1H), 3.71 (s, 3H), 3.68 (s, 3H), 3.58-3.34 (m, 3H), 2.88-2.85 (m, 2H), 2.68-2.65 (m, 1H), 2.41-2.37 (m, 4H), 2.02-1.99 (m, 3H), 1.69-1.67 (m, 3H), 1.61 (m, 2H), 1.58-1.55 (m, 2H), 1.52-1.50 (m, 3H), 1.18 (d, J=4.0 Hz, 3H), 0.93-0.91 (m, 15H) ppm.

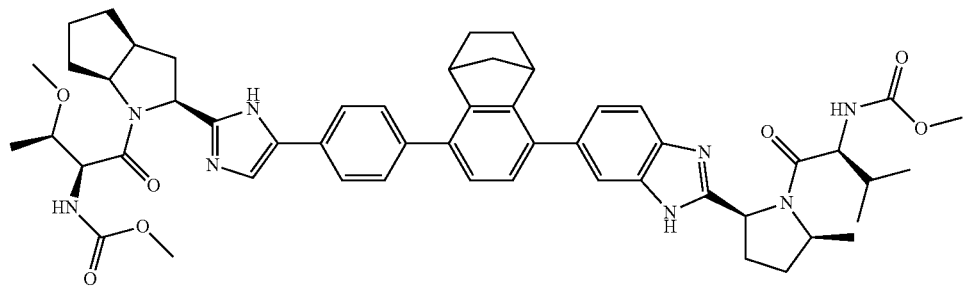 [SMILES: COC(=O)N[C@H](C(=O)N1[C@@H](C)CC[C@H]1c1nc2ccc(-c3ccc(-c4ccc(-c5cnc([C@@H]6C[C@@H]7CCC[C@@H]7N6C(=O)[C@@H](NC(=O)OC)[C@@H](C)OC)[nH]5)cc4)c4c3C3CCC4C3)cc2[nH]1)C(C)C]

Example 11
Synthetic Route:
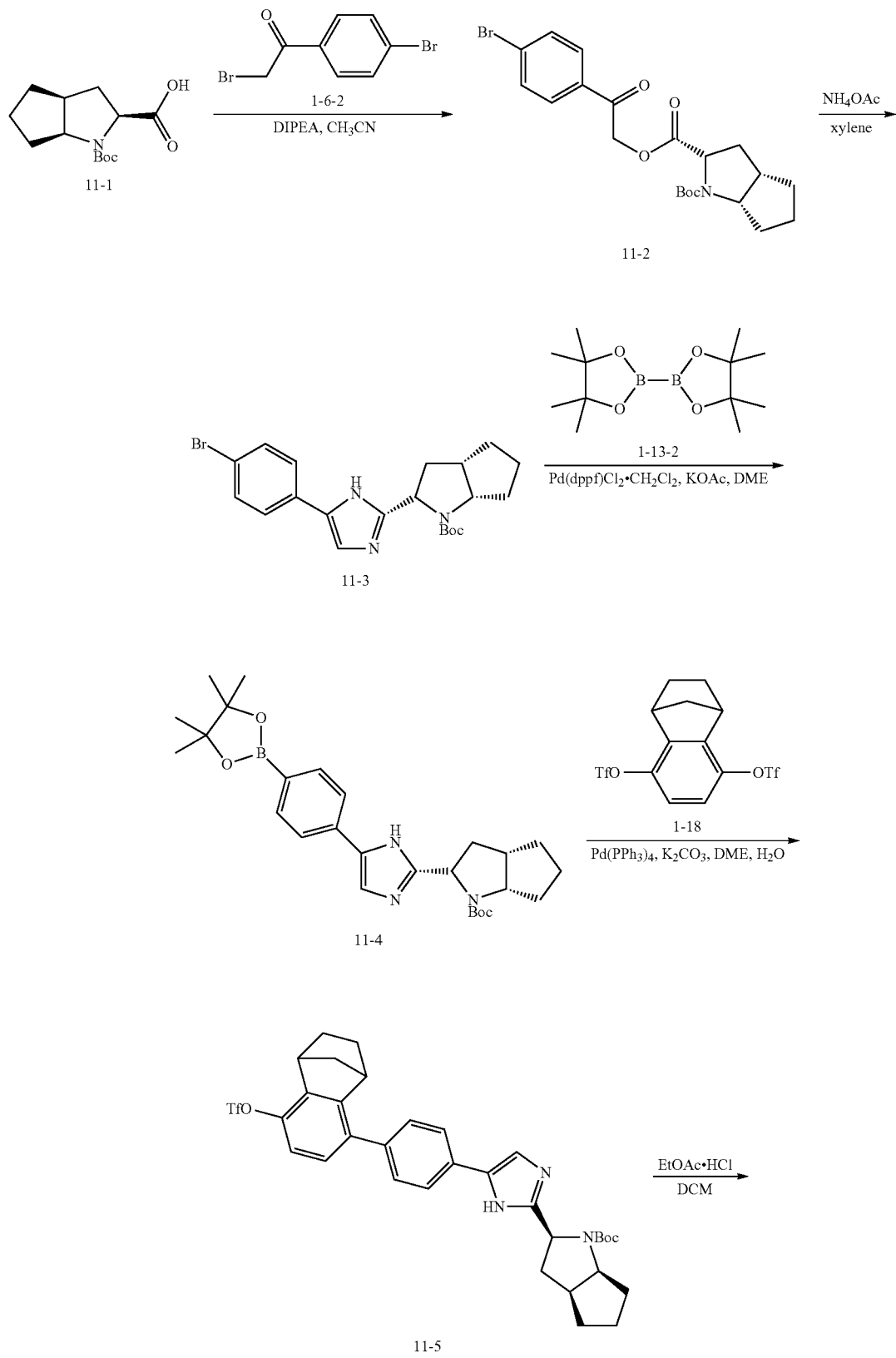

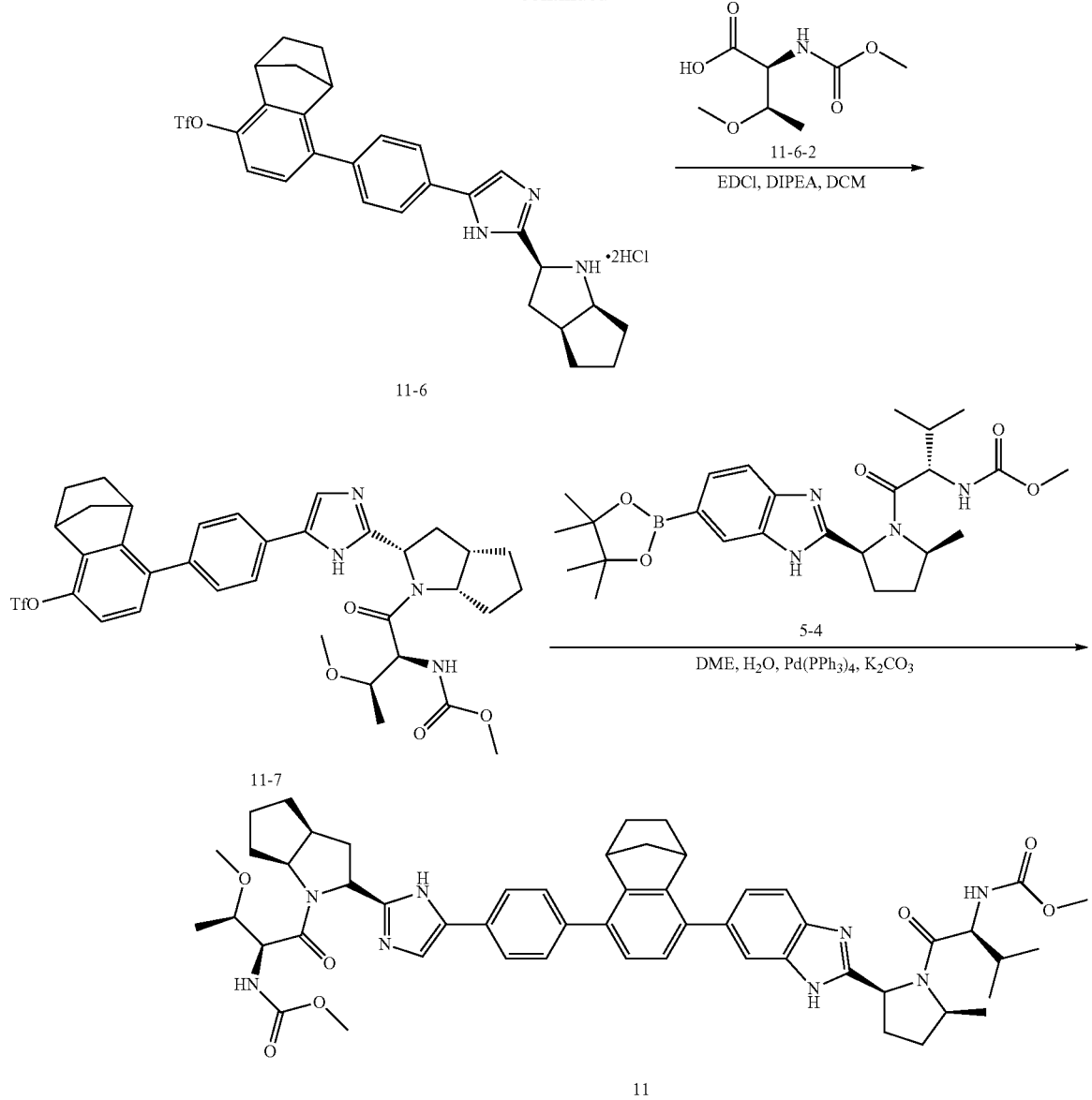

Step 1) the Preparation of Compound 11-2

The title compound was prepared by the procedure described in step 1 of Example 9 using DIPEA (1.3 mL, 7.36 mmol), compound 11-1 (1.67 g, 6.55 mmol), compound 1-6-2 (2.0 g, 7.2 mmol) and acetonitrile (50 mL) to give the title compound as a white solid (2.78 g, 94%). The compound was characterized by the following spectroscopic data:

MS (ESI, pos.ion) m/z: 453.3 [M+H]$^+$; and $^1$H NMR (400 MHz, CDCl$_3$): δ 7.78 (m, 2H), 7.65 (m, 2H), 5.54-5.15 (m, 2H), 4.39 (m, 1H), 3.76 (m, 1H), 3.03 (m, 1H), 2.53 (m, 1H), 1.84 (m, 1H), 1.62 (m, 4H), 1.43 (m, 9H), 1.24 (m, 2H) ppm.

Step 2) the Preparation of Compound 11-3

The title compound was prepared by the procedure described in step 2 of Example 9 using compound 11-2 (2.78 g, 6.1 mmol), ammonium acetate (4.7 g, 61 mmol) and xylene (30 mL) to give the title compound as white solid (1.73 g, 65%). The compound was characterized by the following spectroscopic data:

MS (ESI, pos.ion) m/z: 433.3 [M+H]$^+$; and $^1$H NMR (400 MHz, CDCl$_3$): δ 7.78 (m, 2H), 7.65 (m, 2H), 7.35 (s, 1H), 4.39 (m, 1H), 3.76 (m, 1H), 3.03 (m, 1H), 2.53 (m, 1H), 1.84 (m, 1H), 1.63 (m, 4H), 1.43 (m, 9H), 1.24 (m, 2H) ppm.

Step 3) the Preparation of Compound 11-4

The title compound was prepared by the procedure described in step 3 of Example 9 using DME (20 mL), compound 11-3 (1.73 g, 4.0 mmol), 4,4,4',4',5,5,5',5'-octamethyl-2,2'-bi(1,3,2-dioxaborolane) (1.12 g, 4.4 mmol), Pd(dppf)Cl$_2$.CH$_2$Cl$_2$ (82 mg, 0.1 mmol) and KOAc (0.78 g, 8.0 mmol) to give the title compound as a light yellow solid (1.76 g, 92%). The compound was characterized by the following spectroscopic data:

MS (ESI, pos.ion) m/z: 480.4 [M+H]$^+$; and $^1$H NMR (400 MHz, CDCl$_3$): δ 7.78 (m, 2H), 7.65 (m, 2H), 7.35 (s, 1H), 4.39 (m, 1H), 3.76 (m, 1H), 3.03 (m, 1H), 2.53 (m, 1H), 1.84 (m, 1H), 1.63 (m, 4H), 1.43 (m, 9H), 1.24 (m, 2H), 1.22 (s, 12H) ppm.

Step 4) the Preparation of Compound 11-5

The title compound was prepared by the procedure described in step 4 of Example 9 using compound 1-18 (8.20 g, 18.6 mmol), compound 11-4 (9.1 g, 19.0 mmol), Pd(PPh$_3$)$_4$ (1.07 g, 0.93 mmol), K$_2$CO$_3$ (10.28 g, 74.4 mmol) and a mixture solvent of DME and water (v/v=3/1, 80 mL) to give the title compound as a white solid (6.1 g, 51%). The compound was characterized by the following spectroscopic data:

MS (ESI, pos.ion) m/z: 644.7 [M+H]$^+$; and
$^1$H NMR (400 MHz, CDCl$_3$): δ 10.53 (br.s, 1H), 7.83 (br.s, 1H), 7.42 (d, J=8.1 Hz, 2H), 7.26 (m, 2H), 7.20 (d, J=8.6 Hz, 1H), 7.02 (d, J=8.6 Hz, 1H), 4.98 (d, J=5.2 Hz, 1H), 3.70 (s, 1H), 3.60 (s, 1H), 3.48-3.35 (m, 1H), 2.25-2.10 (m, 2H), 2.04-1.96 (m, 3H), 1.82-1.80 (m, 2H), 1.59-1.56 (m, 4H), 1.51 (s, 9H), 1.43-1.39 (m, 4H) ppm.

Step 5) the Preparation of Compound 11-6

The title compound was prepared by the procedure described in step 5 of Example 9 using a solution of HCl in EtOAc (24 mL, 4 mol/L), compound 11-5 (6.10 g, 9.48 mmol) and DCM (60 mL) to give the title compound as an offwhite solid (4.17 g, 71%). The compound was characterized by the following spectroscopic data:

MS (ESI, pos. ion) m/z: 544.6[M+H]$^+$.

Step 6) the Preparation of Compound 11-7

The title compound was prepared by the procedure described in step 6 of Example 9 using DIPEA (0.18 mL, 1 mmol), compound 11-6 (272 mg, 0.5 mmol), compound 11-6-2 (101 mg, 0.53 mmol), EDCI (115 mg, 0.6 mmol) and DCM (10 mL) to give the title compound as a white solid (249 mg, 82%). The compound was characterized by the following spectroscopic data:

MS (ESI, pos. ion) m/z: 703.8 [M+H]$^+$; and
$^1$H NMR (400 MHz, CDCl$_3$): δ 10.53 (br.s, 1H), 7.83 (br.s, 1H), 7.42 (d, J=8.1 Hz, 2H), 7.26 (m, 2H), 7.20 (d, J=8.6 Hz, 1H), 7.02 (d, J=8.6 Hz, 1H), 4.85-4.81 (m, 2H), 4.63-4.61 (m, 1H), 4.38-4.36 (m, 1H), 4.21-4.19 (m, 1H), 3.71 (s, 3H), 3.31 (s, 3H), 2.88-2.85 (m, 2H), 2.68-2.65 (m, 1H), 2.41-2.37 (m, 4H), 2.02-1.99 (m, 3H), 1.85-1.83 (m, 1H), 1.69-1.67 (m, 4H), 1.44-1.41 (m, 2H), 1.20 (d, J=4.0 Hz, 3H) ppm.

Step 7) the Preparation of Compound 11

The title compound was prepared by the procedure described in step 7 of Example 9 using compound 11-7 (144 mg, 0.2 mmol), compound 5-4 (97 mg, 0.2 mmol), Pd(PPh$_3$)$_4$ (23 mg, 0.02 mmol), K$_2$CO$_3$ (56 mg, 0.4 mmol) and a mixture solvent of DME (8 mL) and water (2 mL) to give the title compound as a light yellow solid (98 mg, 53%). The compound was characterized by the following spectroscopic data:

MS (ESI, pos. ion) m/z: 926.1[M+H]$^+$; and
$^1$H NMR (400 MHz, CDCl$_3$): δ 8.33-8.31 (m, 2H), 8.05 (br.s, 1H), 7.83 (s, 1H), 7.67 (s, 1H), 7.60 (d, J=4.0 Hz, 1H), 7.41-7.39 (m, 2H), 7.35 (s, 1H), 7.23 (s, 1H), 4.85-4.81 (m, 2H), 4.63-4.61 (m, 1H), 4.38-4.36 (m, 1H), 4.21-4.19 (m, 1H), 3.71 (s, 3H), 3.68 (s, 3H), 3.58-3.54 (m, 2H), 3.37 (s, 3H), 2.88-2.85 (m, 2H), 2.68-2.65 (m, 1H), 2.41-2.37 (m, 2H), 2.02-1.99 (m, 3H), 1.86-1.84 (m, 1H), 1.69-1.67 (m, 3H), 1.61 (m, 2H), 1.58-1.55 (m, 5H), 1.52-1.50 (m, 3H), 1.44-1.41 (m, 4H), 1.18 (d, J=4.0, 3H), 0.93-0.91 (m, 6H) ppm.

BIOLOGICAL ACTIVITY

HCV Replicon System was utilized as a screening model in the present disclosure to evaluate the antivirus effects of the compounds disclosed herein against HCV. HCV Replicon assay was first described in Science, 1999, 285 (5424), 110-3. HCV Replicon System is one of the most important tools for research on HCV RNA replication, pathogenicity and persistent of virus, for example, 5'-NCR minimum areas is necessary for HCV RNA replication that was proved by using replicon, and HCV Replicon System was utilized successfully as an evaluation model of antiviral drugs. To determine the potential anti-HCV effects of the test compounds, luciferase assay and antibiotic Neomycin resistance gene were tested according to the method described in Science. 1999 Jul. 2; 285 (5424), 110-3 and J. Virol. 2003 March; 77 (5), 3007-19.

In a word, the compounds disclosed herein were tested by using human hepatic carcinoma cell line Huh-7 which is transfected stably with HCV GT1a, GT1b or GT2a replicon respectively, and resistant cells of Y93H, L31F, P32L or I302V and wild-type cells HCV 1b. HCV Replicon System disclosed herein contains G418 resistance gene NEO and Luciferase Reporter Gene, and the level of HCV replication in host cells is detected and characterized by the expression level of the NEO gene or Luciferase Reporter Gene, so the effects of the compounds herein inhibit HCV replication can be evaluated in this system. In this article, a real-time quantitative polymerase chain reaction (qPCR) method was used to detect NEO gene expression level, and chemiluminescence method was used to test Luciferase Reporter Gene expression level.

Operating Procedure:

1. Test Method for Measuring EC$_{50}$ of the Compounds Based on Luciferase Assay.

The Huh-7 cells transfected with HCV replicons system were seeded into 96-well plates (8,000 cells in 125 μL/well) respectively; each test compound was diluted to desired concentration using 5-fold serial dilutions protocol, 10 doses in duplicate (initial concentration for 10 nM) and added to wells with POD™ 810 Plate Assembler. The plates were incubated in a CO$_2$ incubator for 72 hours; after that, 40 μL of Luciferase assay substrate (Promega Bright-Glo) was added to each well, and detected by a chemiluminescence detection system (Topcount Microplate Scintillation and Luminescence Counter) 5 minutes later; the EC$_{50}$ (half-maximal effective concentration, concentration for 50% of maximal effect) values of test compounds were analyzed by GraphPad Prism software. In this paper, experiments were repeated twice and set the wells without compounds as negative control.

2. Test Method for Measuring EC$_{50}$ of the Compounds by Detecting Antibiotic G418 Resistance Gene NEO Gene.

The Huh-7 cells transfected with HCV replicons system were seeded into 96-well plates (8,000 cells in 125 μL/well) respectively; each test compound was diluted to desired concentration using 5-fold serial dilutions protocol, 10 doses in duplicate (initial concentration for 10 nM) and added to wells with POD™ 810 Plate Assembler. The plates were incubated in a CO2 incubator for 72 hours; and detected the expression level of the NEO gene expression with real-time quantitative PCR later; the EC$_{50}$ (half-maximal effective concentration, concentration for 50% of maximal effect) values of test compounds were analyzed by GraphPad Prism software, respectively. In this paper, experiments were repeated twice and set the wells without compounds as negative control.

3. Results

The test compounds of the present disclosure can be effective against the HCV 1a, 1b, 2a, 2b, 3a, 3b, 4a, 5a and 6a genotypes according to the experiment data, and EC50 ranges of the test compounds against HCV 1b are 1 pM-99 nM; Table 2 shows the $EC_{50}$ values of representative compounds of the present disclosure against the HCV 1a and HCV 1b genotypes.

TABLE 2

| Example | 1a (nM) | 1b (nM) | Example | 1a (nM) | 1b (nM) | Example | 1a (nM) | 1b (nM) |
|---|---|---|---|---|---|---|---|---|
| 1 | 0.019 | 0.004 | 2 | 0.004 | 0.004 | 3 | 0.008 | 0.005 |
| 4 | 0.131 | 0.005 | 5 | 0.098 | 0.007 | 6 | 0.032 | 0.006 |
| 7 | 0.087 | 0.005 | 8 | 0.063 | 0.009 | 9 | 0.123 | 0.008 |
| 10 | 0.057 | 0.009 | 11 | 0.235 | 0.012 | | | |

The experiment results of HCV 1b wild-type and Y93H, L31F, P32L, I302V resistance cells and the simulation results of molecular modeling and docking show that the present disclosure plays an excellent anti-HCV role, which suggest a novel anti-HCV mechanism by interfering with HCV NS5A protein.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A. The compounds of the present disclosure may inhibit multiple genotypes of HCV.

In the description of the invention, the reference term "one embodiment," "some embodiments," "example", "a specific example", or "some examples" and means in connection with the embodiment described in or example described in Example particular feature, structure, material, or characteristic be included in the present invention, at least one embodiment or example. In the present specification, the term of the above schematic representation is not necessarily referring to the same embodiment or example. Moreover, describe a particular feature, structure, material, or characteristics can be in any one or more embodiments or examples in combination in an appropriate manner. Although embodiments of the present invention has been shown and described above, the above embodiments are illustrative embodiments that can be understood, and cannot be understood as a limit for the invention, the skills in the art without departing from the principles of the invention and purpose, can change modify, substitute, and vary these embodiments within the scope of the present invention.

What is claimed is:

1. A compound having Formula (I), or a stereoisomer, a tautomer, an N-oxide, a hydrate, a solvate, a metabolite, a pharmaceutically acceptable salt or a prodrug thereof:

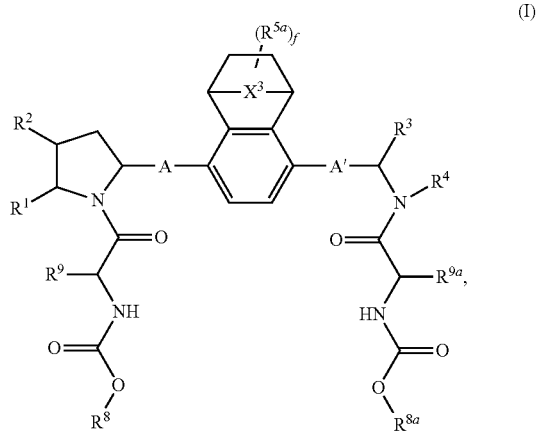

(I)

wherein $X^3$ is $(CR^7R^{7a})_e$;
each $R^7$ and $R^{7a}$ is independently H or $C_{1-3}$ alkyl;
e is 1 or 2;
each of A and A' is independently

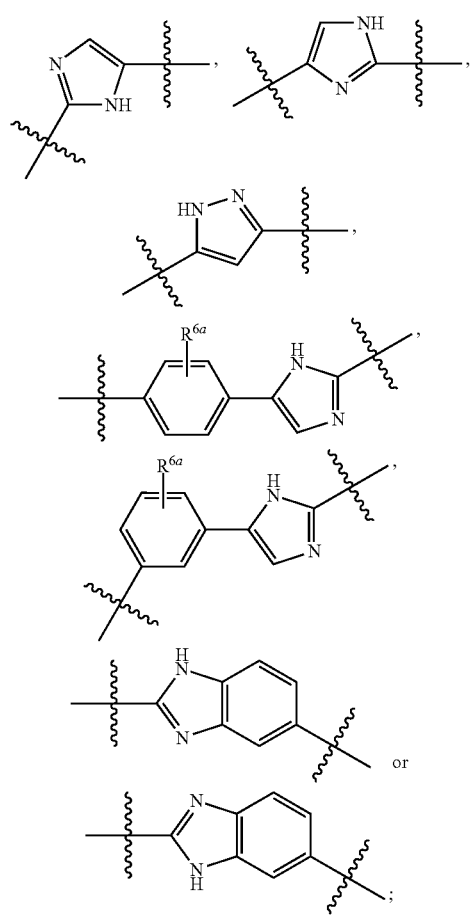

$R^1$ is $C_{1-4}$ alkyl, $C_{1-4}$ heteroalkyl or $C_{6-10}$ aryl;
$R^2$ is H, deuterium, $C_{1-4}$ alkyl, $C_{1-4}$ heteroalkyl or $C_{6-10}$ aryl;
$R^3$ and $R^4$, together with N—CH to which they are attached, form one of the following groups:

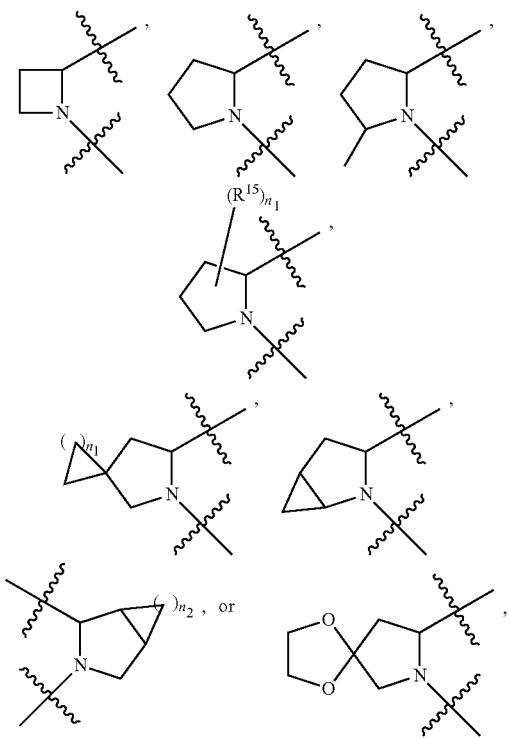

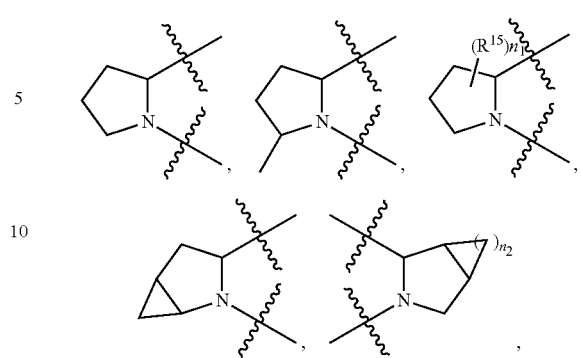

wherein each R[15] is independently H, F, Cl, Br, I, cyano, hydroxy, phenyl, $C_{1-4}$ alkyl, $C_{1-4}$ hydroxyalkyl, $C_{1-4}$ haloalkyl, $C_{1-4}$ alkoxy, $C_{1-4}$ alkoxy-$C_{1-4}$-alkyl, or $C_{2-10}$ heterocyclyl;

and each $n_1$ and $n_2$ is independently 1, 2, 3 or 4.

4. The compound according to claim 1 having formula (II):

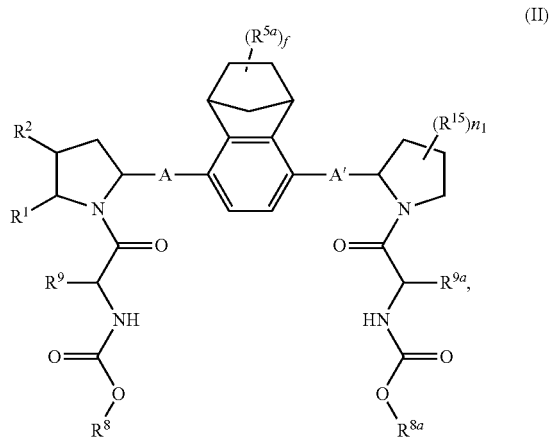

wherein each of A and A' is independently

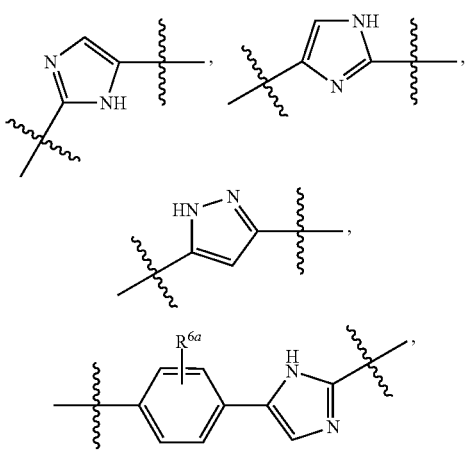

wherein each R[15] is independently H, deuterium, F, Cl, Br, I, cyano, hydroxy, oxo(=O), phenyl, $C_{1-4}$ alkyl, $C_{1-4}$ hydroxyalkyl, $C_{1-4}$ haloalkyl, $C_{1-4}$ alkoxy, $C_{1-4}$ alkoxy-$C_{1-4}$-alkyl, $C_{1-4}$ alkylamino, $C_{6-10}$ arylamino, $C_{6-10}$ aryloxy, $C_{1-9}$ heteroaryl, $C_{1-9}$ heteroaryloxy, $C_{2-6}$ alkenyl or $C_{2-10}$ heterocyclyl;

each R[6] is independently H, $C_{1-4}$ alkyl, $C_{1-4}$ haloalkyl, $C_{1-4}$ hydroxyalkyl, $C_{1-4}$ amnioalkyl, $C_{1-6}$ alkoxy-$C_{1-4}$-alkyl, $C_{1-6}$ alkylamino-$C_{1-4}$-alkyl, $C_{6-10}$ aryl-$C_{1-4}$-alkyl, $C_{6-10}$ aryl, $C_{2-10}$ heterocyclyl or $C_{3-8}$ cycloalkyl;

each $n_1$ and $n_2$ is independently 1, 2, 3 or 4;

each R[5a] and R[6a] is independently H, deuterium, oxo (=O), hydroxy, amino, F, Cl, Br, I, cyano, mercapto, nitro, $C_{1-6}$ alkoxy, $C_{1-6}$ alkyl, $C_{6-10}$ aryl, —$CF_3$, $C_{1-6}$ alkylamino, $C_{3-10}$ cycloalkyl or $C_{6-10}$ aryloxy;

each R[9] and R[9a] is independently H, deuterium, $C_{1-6}$ alkyl, $C_{1-6}$ alkoxy-$C_{1-6}$-alkyl, $C_{1-6}$ haloalkyl, $C_{1-6}$ hydroxyalkyl, $C_{1-6}$ heteroalkyl, $C_{1-6}$ alkylamino-$C_{1-6}$-alkyl, $C_{6-10}$ aryl-$C_{1-6}$-alkyl, $C_{1-9}$ heteroaryl-C $C_{2-10}$ heterocyclyl-$C_{1-6}$-alkyl, $C_{3-8}$ cycloalkyl-$C_{1-6}$-alkyl, $C_{6-10}$ aryl, $C_{1-9}$ heteroaryl, $C_{2-10}$ heterocyclyl or $C_{3-8}$ carbocyclyl;

each of R[8] and R[8a] is independently H, deuterium, $C_{1-6}$ alkyl, $C_{1-6}$ haloalkyl, $C_{1-6}$ hydroxyalkyl, $C_{1-6}$ heteroalkyl, $C_{6-10}$ aryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and f is 0, 1, 2, 3 or 4.

2. The compound according to claim 1, wherein $X^3$ is $(CR^7R^{7a})_e$;

e is 1 or 2; and each R[7] and R[7a] is independently H.

3. The compound according to claim 1, wherein R[3] and R[4], together with N—CH to which they are attached, form one of the following groups:

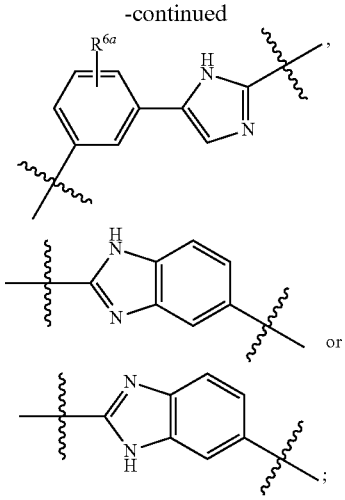

R[1] is methyl, ethyl, i-propyl, or phenyl;
R[2] is H, deuterium, methyl, ethyl, i-propyl, or phenyl;
each R[5a] is independently H, deuterium, oxo (=O), —CF$_3$, methyl, ethyl, phenyl, benzyl, F, Cl, Br or I;
each R[6a] is independently H, deuterium, oxo (=O), hydroxy, amino, F, Cl, Br, I, cyano, methyl, ethyl, i-propyl, cyclohexyl, phenyl, benzyl, —CF$_3$, —OCF$_3$, mercapto, nitro, C$_{1-3}$ alkylamino or C$_{3-8}$ cycloalkyl;
each of R[8] and R[8a] is independently H, deuterium, methyl, ethyl, phenyl, cyclohexyl, 1-methylpropyl, i-propyl or t-butyl;
each of R[9] and R[9a] is independently H, deuterium, methyl, ethyl, 1-methylpropyl, phenyl, i-propyl, tetrahydropyranyl, or t-butyl;
each R[15] is independently H, deuterium, F, Cl, Br, I, cyano, hydroxy, methyl, ethyl, methoxylmethyl, i-propyl, i-butyl or phenyl;
n$_1$ is 1, 2, 3 or 4; and
f is 0, 1, 2, 3 or 4.

5. The compound according to claim 1 having one of the following formulae:

(1)

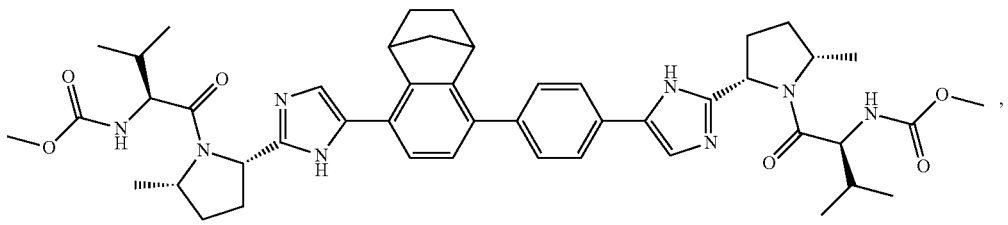

(2)

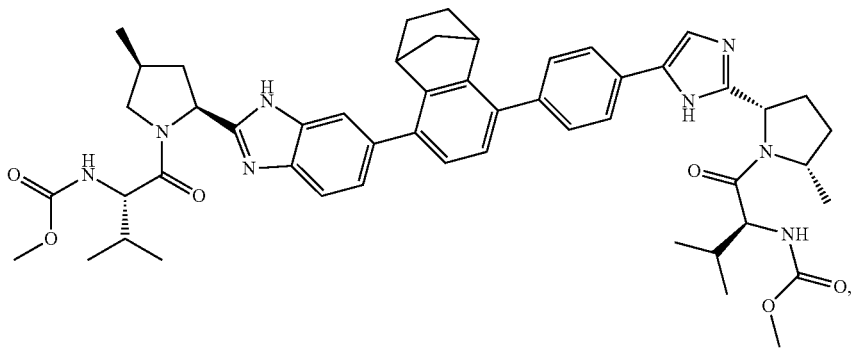

(3)

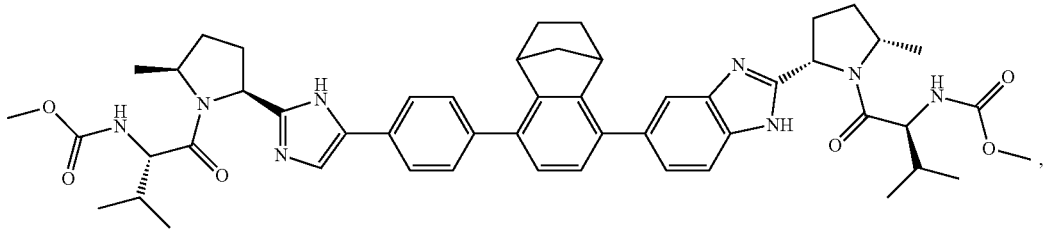

(4)

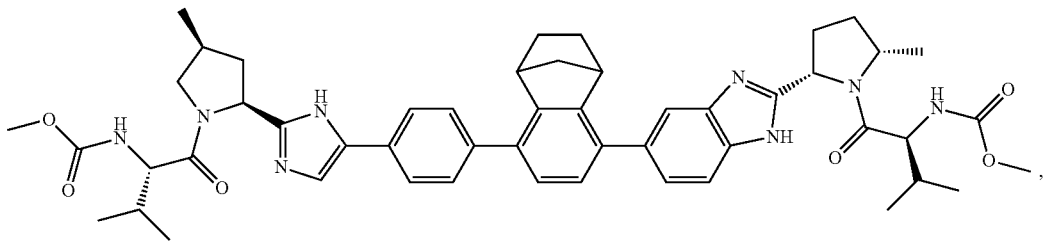

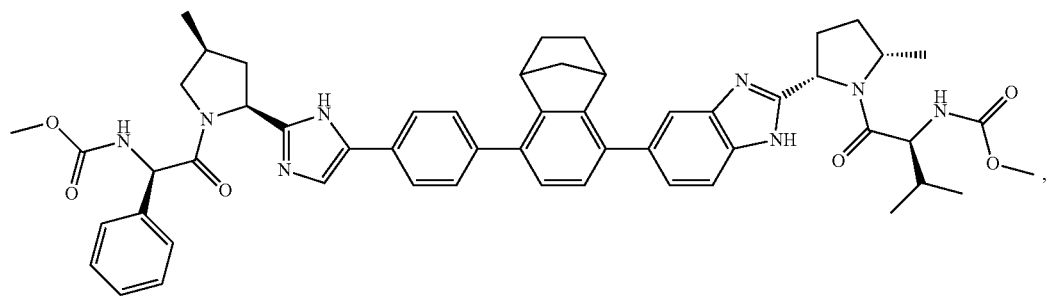
(5)
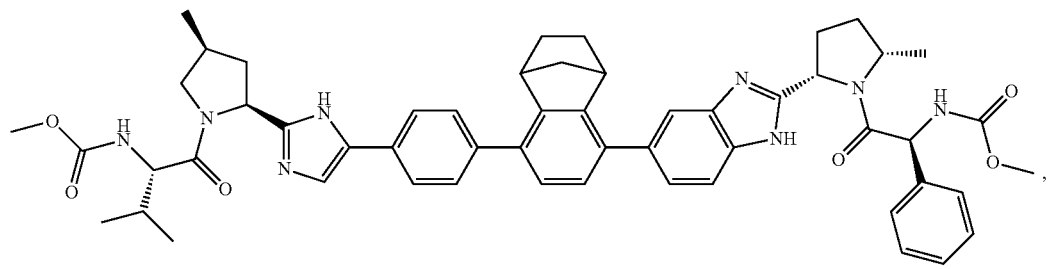
(6)
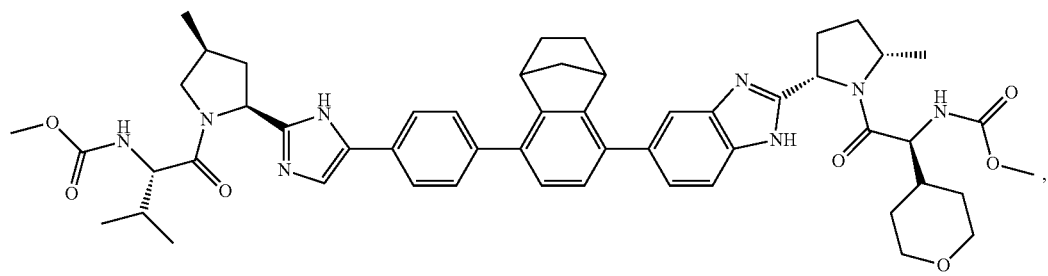
(7)
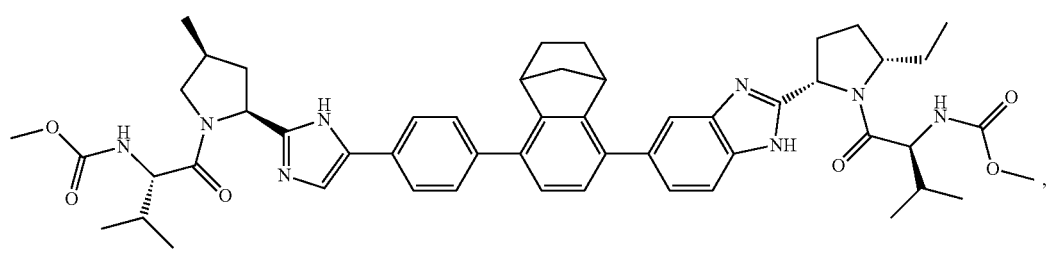
(8)
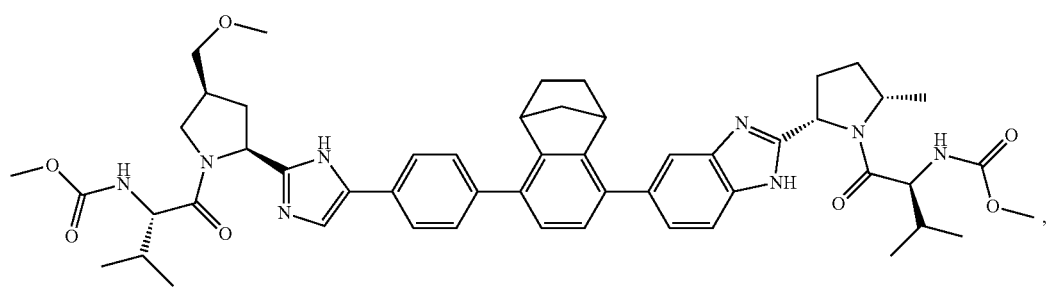
(9)

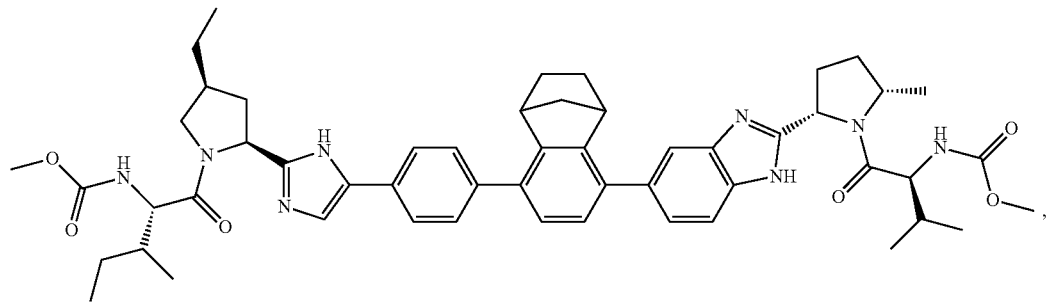
(10)
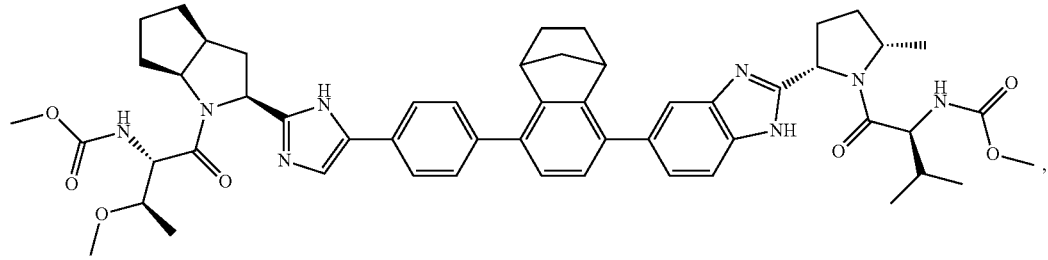
(11)
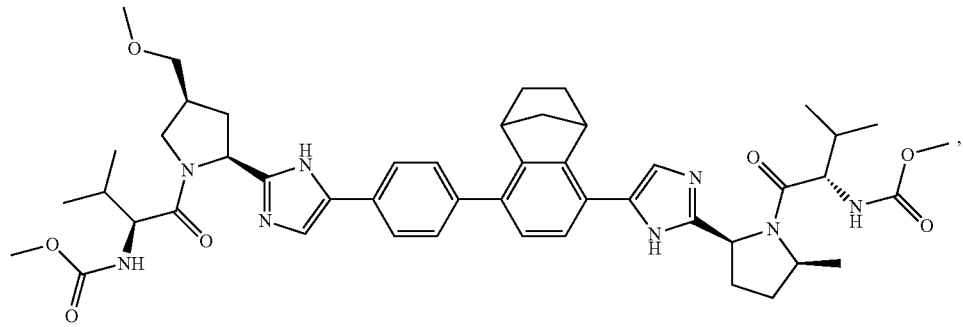
(12)
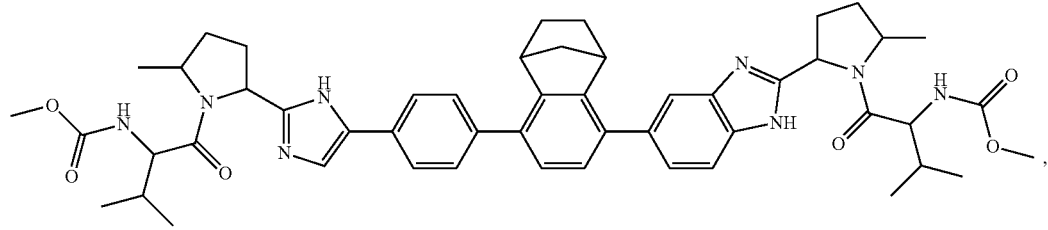
(13)
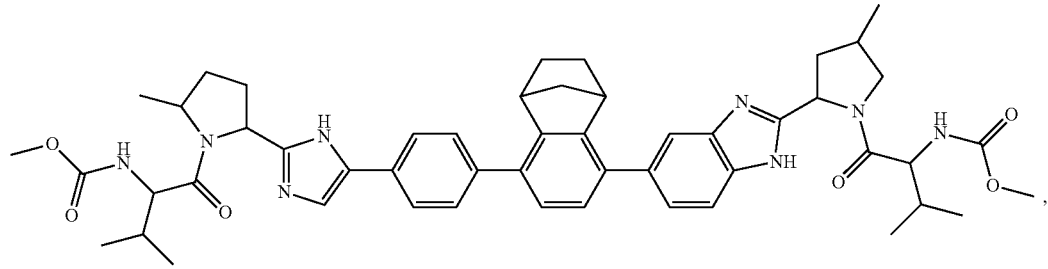
(14)

(15)

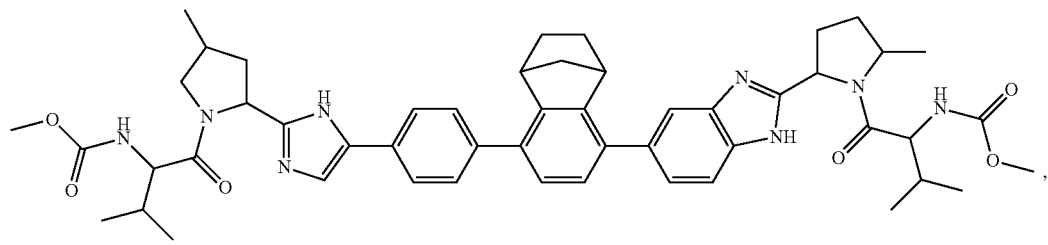

(16)

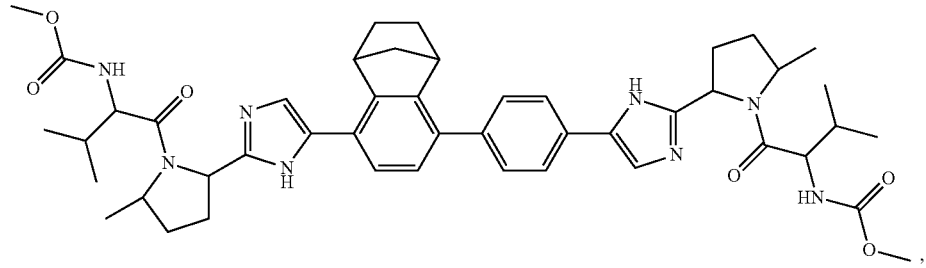

(17)

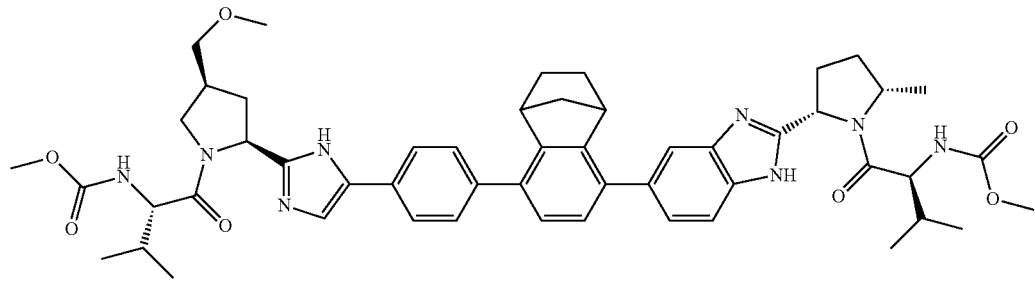

or a stereoisomer, a tautomer, an N-oxide, a hydrate, a solvate, or a pharmaceutically acceptable salt thereof.

6. A pharmaceutical composition comprising the compound according to claim 1; and a pharmaceutically acceptable carrier, excipient, diluent, adjuvant, vehicle or a combination thereof.

7. The pharmaceutical composition according to claim 6 further comprising an anti-HCV agent; wherein the anti-HCV agent is interferon, ribavirin, IL-2, IL-6, IL-12, a compound that enhances the development of a type 1 helper T cell response, interfering RNA, anti-sense RNA, imiquimod, an inosine5'-monophosphate dehydrogenase inhibitor, amantadine, rimantadine, bavituximab, a HCV neutralizing polyclonal antibody (CIVACIR®), boceprevir, telaprevir, erlotinib, daclatasvir, simeprevir, asunaprevir, vaniprevir, faldaprevir, paritaprevir, danoprevir, sovaprevir, grazoprevir, vedroprevir, BZF-961, GS-9256, narlaprevir, ANA-975, ombitasvir, EDP-239, PPI-668, velpatasvir, samatasvir, elbasvir, MK-8325, GSK-2336805, PPI-461, BI-2013335, ciluprevir, ACH-1095, VX-985, IDX-375, VX-500, VX-813, PHX-1766, PHX-2054, IDX-136, IDX-316, modithromycin, VBY-376, TMC-649128, mericitabine, sofosbuvir, INX-189, IDX-184, IDX102, R-1479, UNX-08189, PSI-6130, PSI-938, PSI-879, nesbuvir, HCV-371, VCH-916, lomibuvir, MK-3281, dasabuvir, ABT-072, filibuvir, deleobuvir, tegobuvir, A-837093, JKT-109, G1-59728, GL-60667, AZD-2795, TMC647055, MK-3682, GS-9669, odalasvir, furaprevir, setrobuvir, alisporivir, BIT-225, AV-4025, ACH-3422, MK-2748, MK-8325, JNJ-47910382, ABP-560, TD-6450, TVB-2640, ID-12, PPI-383, A-848837, RG-7795, BC-2125 or a combination thereof; and wherein the interferon is interferon α-2b, pegylated interferon α, interferon α-2a, pegylated interferon α-2a, consensus interferon-α, interferon γ or a combination thereof.

8. A method of inhibiting hepatitis C virus (HCV) replication comprising administering the compound according to claim 1.

9. A method of treating hepatitis C virus (HCV) infection or disorder in a patient in need of a treatment for HCV infection or disorder, wherein the method comprises administering a therapeutically effective amount of the compound according to claim 1 to the patient.

10. A method of inhibiting hepatitis C virus (HCV) replication comprising administering the pharmaceutical composition according claim 6.

11. A method of treating hepatitis C virus (HCV) infection or disorder in a patient in need of a treatment for HCV infection or disorder, wherein the method comprises administering a therapeutically effective amount of the pharmaceutical composition according claim 6 to the patient.

* * * * *